(12) United States Patent
Koronyo et al.

(10) Patent No.: US 12,306,192 B2
(45) Date of Patent: May 20, 2025

(54) METHOD OF DETECTING COGNITIVE IMPAIRMENT

(71) Applicant: CEDARS-SINAI MEDICAL CENTER, Los Angeles, CA (US)

(72) Inventors: Maya Koronyo, Los Angeles, CA (US);
Haoshen Shi, Los Angeles, CA (US);
Yosef Koronyo, Los Angeles, CA (US);
Keith L. Black, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 426 days.

(21) Appl. No.: 17/592,433

(22) Filed: Feb. 3, 2022

(65) Prior Publication Data
US 2022/0260591 A1   Aug. 18, 2022

Related U.S. Application Data

(60) Provisional application No. 63/146,878, filed on Feb. 8, 2021.

(51) Int. Cl.
| | |
|---|---|
| *G06K 9/00* | (2022.01) |
| *A61B 3/00* | (2006.01) |
| *A61B 3/10* | (2006.01) |
| *A61B 3/12* | (2006.01) |
| *G01N 33/68* | (2006.01) |

(52) U.S. Cl.
CPC ....... *G01N 33/6896* (2013.01); *A61B 3/0025* (2013.01); *A61B 3/102* (2013.01); *A61B 3/12* (2013.01); *G01N 2800/2821* (2013.01)

(58) Field of Classification Search
CPC ............................................ G06T 2207/30041
See application file for complete search history.

(56) References Cited

U.S. PATENT DOCUMENTS

| | | | |
|---|---|---|---|
| 6,687,007 B1 | 2/2004 | Meigs | |
| 9,839,699 B2 | 12/2017 | Koronyo et al. | |
| 10,413,522 B2 * | 9/2019 | Massague | ............... A61P 35/00 |
| 10,512,699 B2 | 12/2019 | Koronyo et al. | |

(Continued)

FOREIGN PATENT DOCUMENTS

| | | |
|---|---|---|
| WO | 2015188142 A1 | 12/2015 |
| WO | 2019100169 A1 | 5/2019 |

(Continued)

OTHER PUBLICATIONS

Shi, Haoshen, et al. "Retinal capillary degeneration and blood-retinal barrier disruption in murine models of Alzheimer's disease." Acta Neuropathologica Communications 8 (2020): 1-20. (Year: 2020).*

(Continued)

*Primary Examiner* — Hadi Akhavannik
(74) *Attorney, Agent, or Firm* — Nixon Peabody LLP

(57) ABSTRACT

The present invention describes a method for the detection, diagnosis and monitoring of cognitive impairment and Alzheimer's disease. The method involves the detection of pericyte loss and deficiency in PDGFRβ, alone or in combination with retinal vascular Aβ deposits. The method also involves detecting an alteration in blood-retinal barrier (BRB) cell tight junction.

19 Claims, 37 Drawing Sheets
(37 of 37 Drawing Sheet(s) Filed in Color)

(56) References Cited

U.S. PATENT DOCUMENTS

| | | | |
|---|---|---|---|
| 2009/0021724 A1 | 1/2009 | Mahadevan-Jansen et al. | |
| 2011/0286932 A1 | 11/2011 | Koronyo et al. | |
| 2012/0101371 A1 | 4/2012 | Verdooner | |
| 2015/0366450 A1 | 12/2015 | Ren et al. | |
| 2016/0213242 A1* | 7/2016 | Trese | A61B 5/0022 |
| 2018/0242844 A1* | 8/2018 | Liu | A61B 5/0066 |
| 2018/0344806 A1* | 12/2018 | Borodic | A61P 27/02 |
| 2019/0022255 A1 | 1/2019 | Koronyo et al. | |
| 2019/0347796 A1* | 11/2019 | Huang | A61B 3/102 |
| 2020/0221991 A9 | 7/2020 | Wang et al. | |
| 2020/0241012 A1 | 7/2020 | Barghorn et al. | |
| 2022/0285995 A1 | 9/2022 | Alam et al. | |

FOREIGN PATENT DOCUMENTS

| | | | |
|---|---|---|---|
| WO | 2023004436 A1 | 1/2023 | |
| WO | 2023283637 A2 | 2/2023 | |

OTHER PUBLICATIONS

Shi, Haoshen, et al. "Identification of early pericyte loss and vascular amyloidosis in Alzheimer's disease retina." Acta neuropathologica 139 (2020): 813-836. (Year: 2020).*

Shi1 (Year: 2020).*

Shi2 (Year: 2020).*

Shi H, Koronyo Y, Rentsendorj A, Regis GC, etc. Identification of early pericyte loss and vascular amyloidosis in Alzheimer's disease retina. Acta Neuropathol. May 2020; 139(5):813-836. doi: 10.1007/s00401-020-02134-w. Epub Feb. 10, 2020. PMID: 32043162; PMCID: PMC7181564. (Year: 2020).*

International Search Report and Written Opinion for PCT/US2022073558 mailed Dec. 13, 2022, 12 pages.

International Search Report and Written Opinion for PCT/US2022/074083 mailed Oct. 31, 2022, 11 pages.

Koronyo et al., Retinal amyloid pathology and proof-of-concept imaging trial in Alzheimer's disease, Clinical Medicine, 2017, 20 Pages.

Querques et al., Functional and morphological changes of the retinal vessels in Alzheimer's disease and mild cognitive impairment, Scientific Reports, 2019, 9:63, 9 pages.

Ishibazawa et al., Accuracy and reliability in differentiating retinal arteries and veins using widefield en face OCT angiography, Translational Vision Science & Technology, 2019, 8:3, 13 pages.

Hatami et al., Automatic identification of retinal arteries and veins in fundus images using local binary patterns, Elsevier, 2015, 23 pages.

Xiang et al., Physiological amyloid beta clearance in the periphery and its therapeutic potential for Alzheimer's, Acta Neuropathology, 2015, 130:487-499.

* cited by examiner

FIG. 26
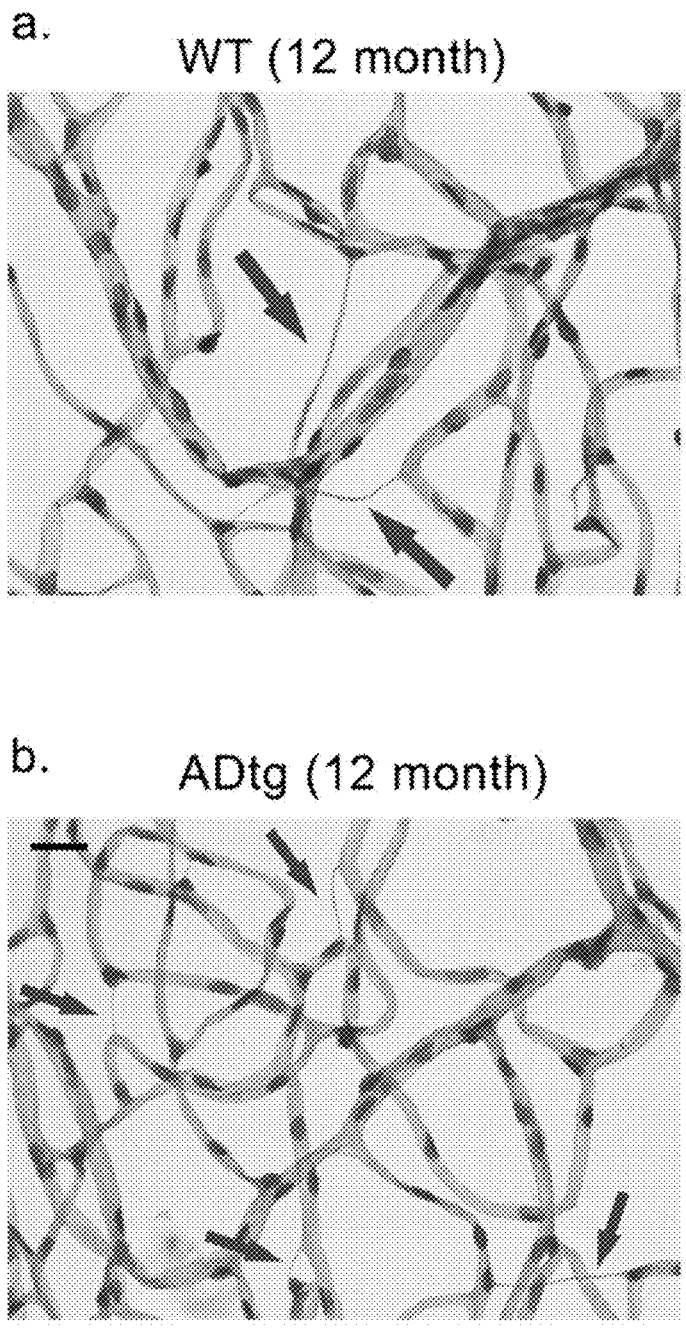
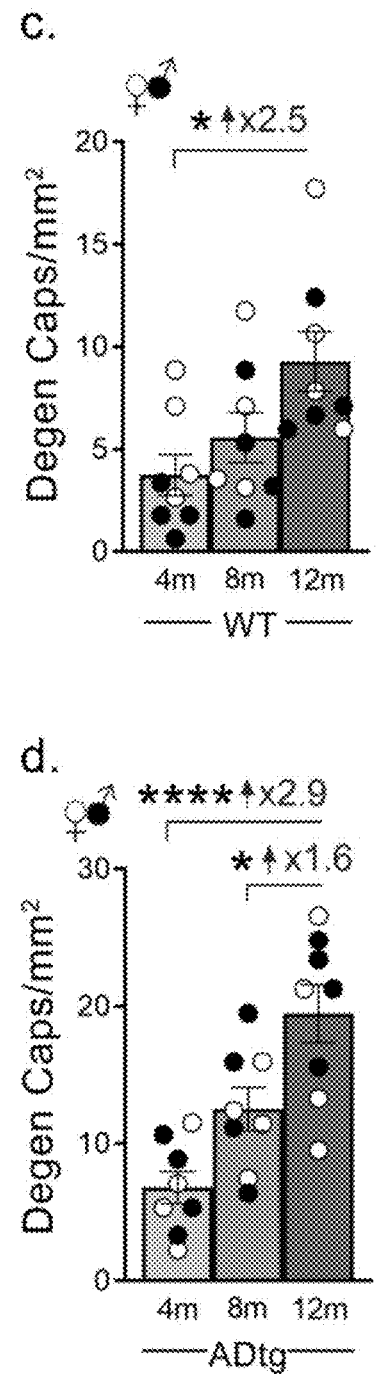

FIG. 30
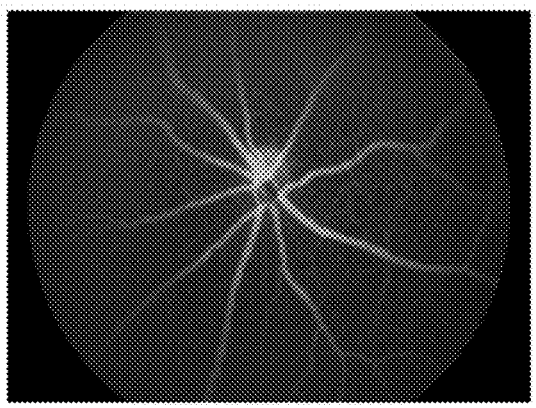
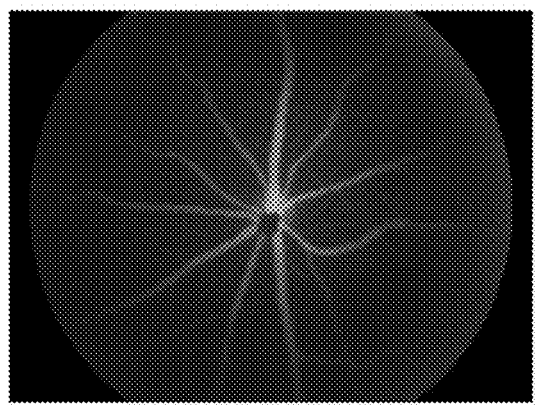

METHOD OF DETECTING COGNITIVE IMPAIRMENT

CROSS-REFERENCE TO RELATED APPLICATIONS

This application includes a claim of priority under 35 U.S.C. § 119(e) to U.S. provisional patent application No. 63/146,878, filed Feb. 8, 2021, the entirety of which is hereby incorporated by reference.

STATEMENT REGARDING FEDERALLY SPONSORED RESEARCH OR DEVELOPMENT

This invention was made with Government support under Grant Nos. AG055865 and AG056478 awarded by National Institutes of Health. The Government has certain rights in the invention.

FIELD OF INVENTION

This invention relates to the detection of and monitoring of cognitive impairment; for example, related with Alzheimer's disease.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cerebral amyloid angiopathy (CAA) is a complex pathological feature found in over 85% of Alzheimer's disease (AD) patients involving deposition of amyloid β-protein (Aβ) in blood vessels and other vascular abnormalities. Recent reports implicate cerebral vascular dysfunctions as early and pivotal contributors to the development of AD and CAA as a reliable predictor of cognitive decline. Moreover, studies of brains from AD patients and animal models have described an accelerated degeneration of pericytes, vascular cells that regulate blood flow in capillaries, and permeability of the blood-brain barrier (BBB), which affected cerebral Aβ accumulation. In addition, brain vascular and perivascular Aβ deposits have also been associated with reduced blood and lymphatic flow, impaired gliovascular unit, as well as altered vessel diameter and accessibility of peripheral immune cells. These combined processes may lead to reduced Aβ clearance rate, heightened inflammation, and eventually neurodegeneration.

Amyloidosis in cerebral vessel walls predominately consists of $A\beta_{40}$ alloforms, which have been implicated in vascular cell toxicity. Along with $A\beta_{40}$, $A\beta_{42}$ alloforms exist in cerebrovascular amyloid deposits of AD patients and in pericytes, presumably triggering pericyte loss and thereby affecting these key components of the neurovascular unit. In addition, drainage of $A\beta_{40}$ and $A\beta_{42}$ through the BBB was demonstrated to be one of the primary clearance mechanisms of cerebral Aβ. Removal of $A\beta_{40}$ via the BBB was shown to be mediated by a scavenger receptor LDL receptor-related protein-1 (LRP-1) in mouse models. Importantly, pericyte degeneration as well as LRP-1 downregulation were collectively identified as predominant mechanisms compromising the BBB in AD patients and AD animal models. In fact, pericyte loss, as assessed by pericyte marker platelet-derived growth factor receptor-β (PDGFRβ) in BBB, was tightly associated with functional breakdown of this barrier. This cell surface receptor is also expressed by vascular smooth muscle cells (vSMCs), which are present in all types of blood vessels except for capillaries and pericytic venules. Further, studies in rodents have shown that the loss of PDGFRβ expression alone leads to a decrease in pericyte and vSMC numbers and damaged brain vasculature.

As such, there remains a need to detect cognitive impairment, for example, related to Alzheimer's disease, and monitor disease progression.

SUMMARY OF THE INVENTION

The following embodiments and aspects thereof are described and illustrated in conjunction with compositions and methods which are meant to be exemplary and illustrative, not limiting in scope.

Described herein is a method of detecting pericytes, platelet-derived growth factor receptor-β (PDGFR-β), low-density lipoprotein (LDL) receptor-related protein-1 (LRP-1), or combinations thereof in a subject in need thereof. In various embodiments of the present disclosure, the method includes obtaining a retinal image of the subject and detecting a decrease in the amount of pericytes, platelet-derived growth factor receptor-β (PDGFR-β), LDL receptor-related protein-1 (LRP-1), or combinations thereof present in a retina of the subject, the decrease detected by comparing the obtained retinal image to a control retinal image or the subject's previous retinal image.

In some embodiments, the subject exhibits one or more symptoms of cognitive impairment and/or the subject has or is suspected of having mild cognitive impairment (MCI) and/or Alzheimer's disease.

In some embodiments, the method further includes diagnosing cognitive impairment or Alzheimer's disease in the subject based on the detection of the decrease in the amount of pericytes, PDGFR-β, LRP-1, or combinations thereof present in the retina of the subject.

In some embodiments, the subject desires a screening regarding mild cognitive impairment (MCI) or Alzheimer's disease.

In some embodiments, detecting the decrease in the amount of pericytes, PDGFR-β, LRP-1 or combinations thereof present in the retina of the subject includes using a live retina imaging technique. In some embodiments, detecting the decrease in the amount of pericytes present in the retina of the subject includes an advanced ophthalmic imaging technique; for example, adaptive optics. In some embodiments, the detecting the decrease in the amount of pericytes, PDGFR-β, LRP-1 or combinations thereof present in the retina of the subject includes using adaptive optics, optical coherence tomography angiography, color fundus photography, fluorescein fundus imaging, fluorescein angiography, indocyanine green angiography, scanning laser ophthalmoscopy, optical coherence tomography, confocal microscopy, retinal hyperspectral imaging, and/or optical coherence tomography angiography (OCTA).

In some embodiments, the detecting the decrease in the amount of PDGFR-β present in the retina of the subject includes administering a contrast agent to the subject and using optical imaging to detect the amount of PDGFR-β present in the retina. In some embodiments, the contrast agent is prednisolone acetate (PA), triamcinolone acetonide (TA), lipid-based artificial tears (LBAT), sodium fluorescein, fluorescein, or indocyanine.

In some embodiments, detecting the decrease in the amount of LRP-1 present in the retina of the subject includes administering a labelled anti-PDGFR-β antibody and using optical imaging to detect the amount of PDGFR-β present in the retina.

In some embodiments, detecting an increase in vascular Aβ deposition in the retina of the subject includes administering a labelled anti-LRP-1 antibody and using optical imaging to detect the amount of LRP-1 present in the retina. In some embodiments, the anti-Aβ compound is anti-Aβ antibody or curcumin.

In some embodiments, the method further includes detecting an increase in vascular Aβ deposition in the retina of the subject. In some embodiments, detecting an increase in vascular Aβ deposition in the retina of the subject includes administering an anti-Aβ compound and using optical imaging to detect the amount of Aβ deposition in the retina, the anti-Aβ compound being anti-Aβ antibody or curcumin.

In some embodiments, the method further includes predicting cognitive decline in the subject based on the detection of the decrease in the amount of pericytes, PDGFR-β, LRP-1, or combinations thereof present in the retina.

In some embodiments, the method further includes monitoring the subject by repeating the method.

Also described herein is a method of monitoring cognitive status of a subject in need thereof. In various embodiments of the present disclosure, the method includes obtaining first retinal image of the subject; detecting, in the first retinal image, an amount of pericytes, platelet-derived growth factor receptor-β (PDGFR-β), LDL receptor-related protein-1 (LRP-1), or combinations thereof present in a retina of the subject; obtaining a second retinal image of the subject subsequent to the first retinal image; detecting, in the second retinal image, an amount of pericytes, PDGFR-β, LRP-1, or combinations thereof present in the retina of the subject; comparing the amount of pericytes, PDGFR-β, LRP-1, or combinations thereof present in the first retinal image and the second retinal image; and detecting whether there is a change in the amount of pericytes, PDGFR-β, LRP-1, or combinations thereof present in the retina.

In some embodiments, the method further includes detecting a decrease in the amount of pericytes, PDGFR-β, LRP-1, or combinations thereof present in the retina and administering a mild cognitive impairment (MCI) or Alzheimer's disease therapy.

In some embodiments, the subject exhibits one or more symptoms of cognitive impairment and/or the subject has or is suspected of having mild cognitive impairment (MCI) and/or Alzheimer's disease. In some embodiments, the subject desires a screening regarding mild cognitive impairment (MCI) or Alzheimer's disease.

In some embodiments, the amount of pericytes, PDGFR-β, LRP-1 or combinations thereof present in the retina of the subject is detected using a live retina imaging technique, an advanced ophthalmic imaging technique, adaptive optics, optical coherence tomography angiography, color fundus photography, fluorescein fundus imaging, fluorescein angiography, indocyanine green angiography, scanning laser ophthalmoscopy, optical coherence tomography, confocal microscopy, retinal hyperspectral imaging, and/or optical coherence tomography angiography (OCTA).

Also described herein is a method of detecting an alteration in blood-retinal barrier (BRB) cell tight junction in a subject in need thereof. In various embodiments of the present disclosure, the method includes assaying a biological sample from the subject and detecting a decrease in claudin-1, in the biological sample, wherein the decrease is compared to a control claudin-1 level or compared to the subject's previous claudin-1 level; or assaying a biological sample from the subject and detecting an increase in NF-κB phosphorylation levels, wherein the increase is compared to a control NF-κB phosphorylation level or compared to the subject's previous NF-κB phosphorylation level; or detecting an increase in retinal vascular leakage level compared to a control level, or compared to the subject's previous retinal vascular leakage level. In various embodiments of the present disclosure, the subject in need thereof exhibits one or more symptoms of cognitive impairment, is a subject having or suspected of having mild cognitive impairment (MCI), or a subject having or suspected of having Alzheimer's disease.

In some embodiments, NF-κB phosphorylation is NF-κB p65 phosphorylation.

In some embodiments, detecting the increase in the retinal vascular leakage level includes administering a fluorophore to the subject; imaging a retina of the subject; and detecting a level of fluorophore leakage from an image of the retina. In some embodiments, the fluorophore is fluorescein, FITC-dextran (2000 kD), Texas Red-dextran (3 kD), or combinations thereof.

In some embodiments, at least one of the decrease in claudin-1, the increase in NF-κB phosphorylation levels, or the increase in retinal vascular leakage level indicates an alteration in BRB cell tight junction.

In some embodiments, the detected alteration in BRB cell tight junction indicates cognitive impairment and/or cognitive decline in the subject.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

Exemplary embodiments are illustrated in referenced figures. It is intended that the embodiments and figures disclosed herein are to be considered illustrative rather than restrictive.

**p<0.01, by two-way ANOVA with Tukey's post-hoc multiple comparison test or by an unpaired 2-tailed Student t-test. P and F values refer to comparisons of age groups ($P_A$, $F_A$), ADtg vs WT genotype groups ($P_G$, $F_G$), and interactions ($P_1$, $F_1$).

Figure 24:
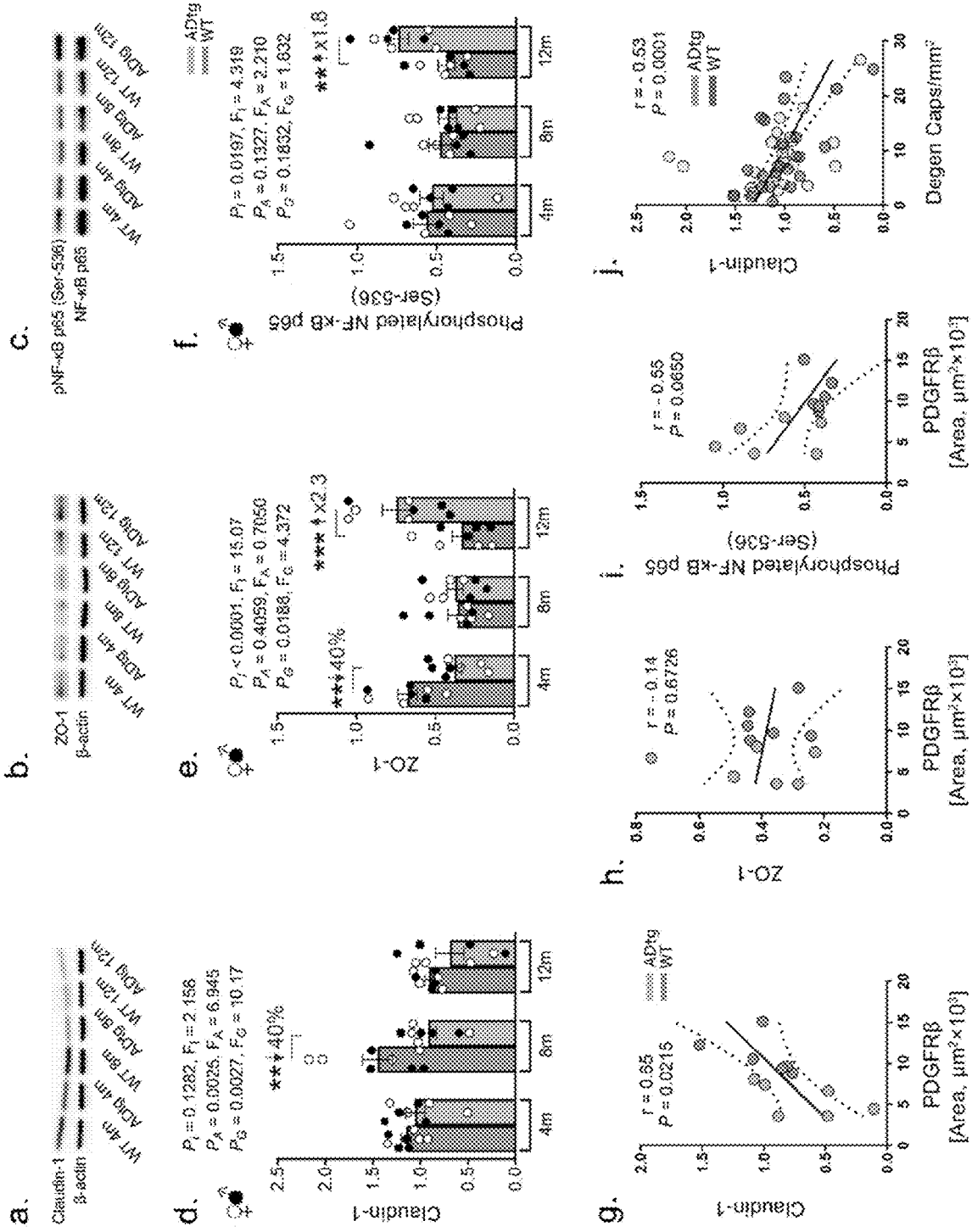

FIG. 24 (panels a-j) shows altered expression of endothelial cell junction molecules and increased NF-κB phosphorylation in the retinas of $APP_{SWF}/PS1_{\Delta E9}$ (ADtg) mice. a-c. Representative Tris-glycine gel images showing western blot protein bands of claudin-1, zonula occludin-1 (ZO-1), phosphorylated NF-κB p65 subunit (pNF-κB p65) at serine-536, and total NF-κB p65 subunit as well as β-actin controls from retinal lysates of ADtg mice and age- and sex-matched wild type (WT) littermates (n=8 for each age and genotype). d-f. Densitometric analyses of western blot protein bands of d. claudin-1, e. ZO-1 and f. pNF-κB p65, normalized by d-e. β-actin control or f. total NF-κB p65 in the same mice cohort. g-i. Pearson's coefficient (r) correlation between retinal PDGFRβ immunoreactivity and the densitometric analysis of western blot protein bands of g. claudin-1, h. ZO-1, or i. pNF-κB p65 in a subset of this mice cohort (n=12). j. Pearson's coefficient (r) correlation between degenerated retinal capillary count and the densitometric analysis of western blot protein bands of claudin-1. Data from individual mice (circles) as well as group means±SEMs are shown. Black-filled circles represent males and clear circles represent females. Fold or percentage changes are shown in red. p<0.01, *p<0.001, by two-way ANOVA with Tukey's post-hoc multiple comparison test. P and F values of two-way ANOVA refer to comparisons of age groups ($P_A$, $F_A$), ADtg vs WT genotype groups ($P_G$, $F_G$), interactions ($P_1$, $F_1$).

Figure 25:
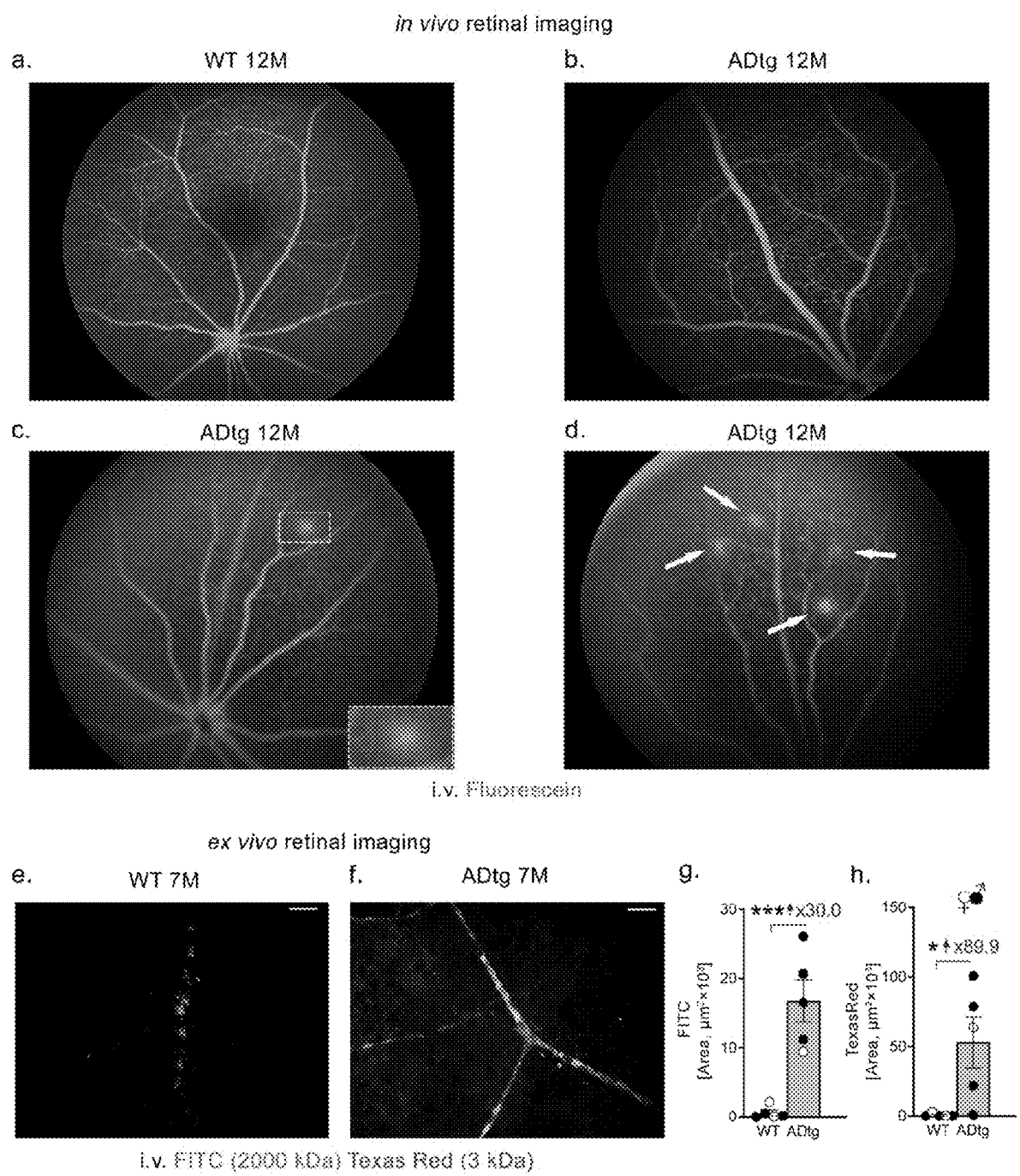

FIG. 25 (panels a-h) shows retinal microvascular leakage in $APP_{SWF}/PS1_{\Delta E9}$ (ADtg) mice. a-d. Representative images of noninvasive retinal microvascular imaging after intraperitoneal fluorescein injection in 12-month-old a. wild type (WT) and b-d. ADtg mice. Note. images in b. showing intact retinal microvasculature and in c-d. showing leaked retinal microvasculature. e-f. Representative images of retinal flatmount obtained from 7-month-old WT and ADtg mice (cohort average age is 6 month) that received intravenous tail injections of FITC-dextran and Texas Red-dextran. g-h. Quantitative analysis of the FITC or Texas Red-stained area in each microscopic field of retinal flat-mounts from WT (n=5) or ADtg (n=5) mice. Black-filled circles represent males and clear circles represent females. *p<0.05, ***p<0.001, by an unpaired 2-tailed Student t-test. Fold changes are shown in red.

Figure 1:
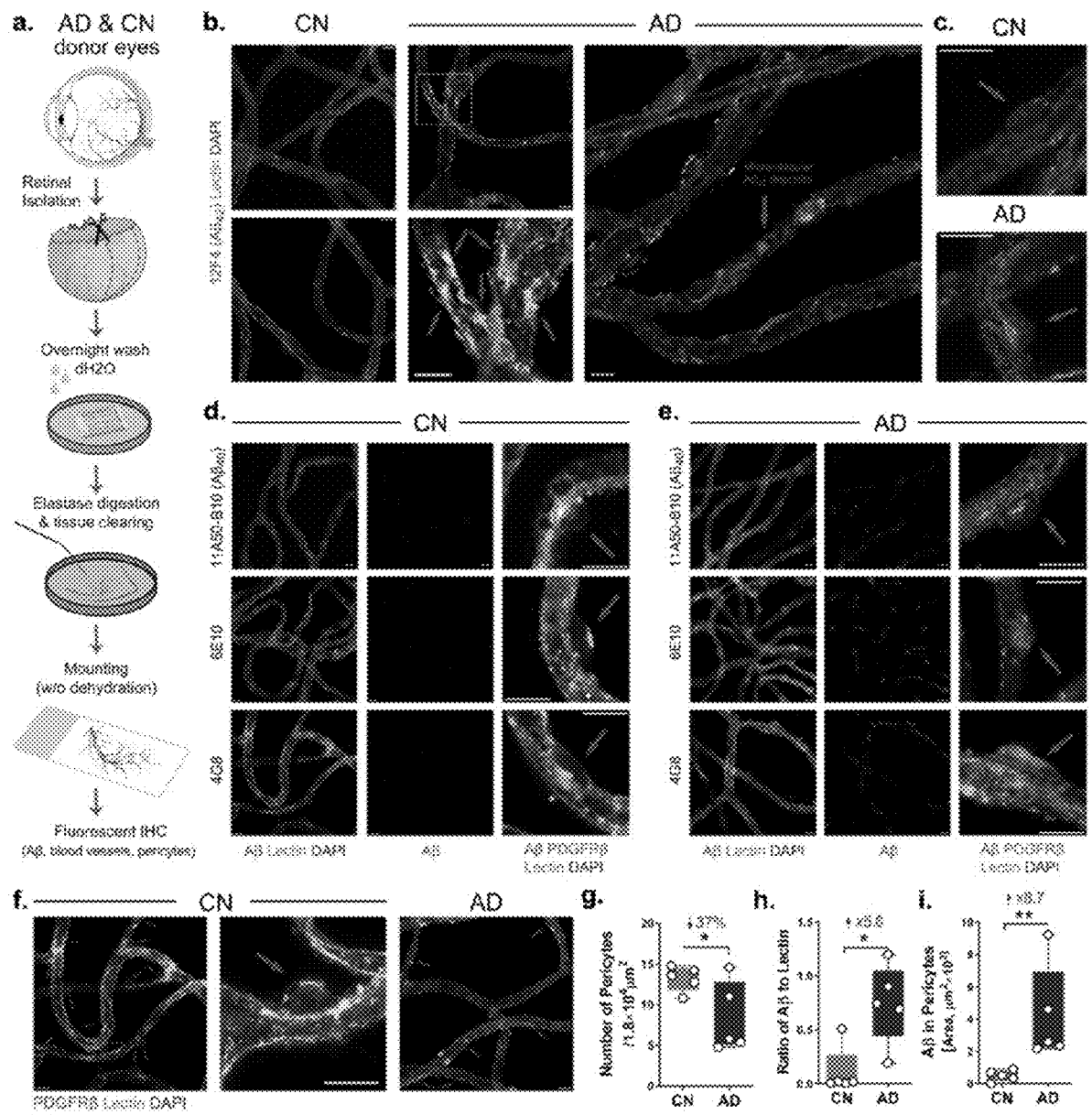
FIG. 1 (panels a-i) shows that microvascular network from postmortem retinas of AD patients exhibit pericyte loss along with Aβ accumulation in blood vessels and pericytes. a. Schema of modified retinal vascular network isolation and immunofluorescent staining. Whole retinas were isolated from donor eyes and 7 mm wide strips were prepared from the temporal retinal hemisphere spanning from the ora serrata to the optic disk. Following fixation, washing, and elastase digestion, vascular network is mounted onto slides without dehydration. Immunofluorescent staining was applied on isolated retinal vascular network to detect Aβ (6E10, 4G8, 12F4 and 11A50), pericytes (PDGFRβ), and blood vessels (lectin). b-c. Representative fluorescent images of isolated retinal microvasculature stained for Aβ$_{42}$ (12F4, red), blood vessels (lectin, green), and nuclei (DAPI, blue) in age- and sex-matched human donors with AD (n=5) and cognitively normal (CN, n=5). Arrows indicate microvascular Aβ$_{42}$ deposits in capillaries on panel b. [a zoomed-in image of AD donor retina (lower image) shows co-localization of Aβ$_{42}$ and retinal vascular wall; yellow spot], or pericytes on panel c.; d-e. Representative fluorescent images of isolated retinal microvasculature stained for Aβ (11A50-B10, 6E10 or 4G8, red), pericytes (PDGFRβ, white), blood vessels (lectin, green), and nuclei (DAPI, blue) in age- and sex-matched AD and CN human donors. Arrows indicate pericytes. f. Representative fluorescent images of isolated retinal microvasculature stained for pericytes (PDGFRβ, red), blood vessels (lectin, green), and nuclei (DAPI, blue). Arrows indicate pericytes. g-i. Quantitative analyses of g. mean number of retinal pericytes in each microscopic visual field ($1.8 \times 10^4$ μm$^2$ area), h. ratio of retinal vascular Aβ immunoreactive (IR) area to lectin IR area from each microscopic visual field ($1.8 \times 10^4$ μm$^2$ area), and i. Aβ IR area within pericytes, in the same cohort of AD (n=5) and CN (n=5) human donors. Scale bars=10 μm. Data from individual subjects as well as group mean±SEM are shown. Fold and percent changes are shown in red. *p<0.05, **p<0.01, determined by unpaired 2-tailed Student's t test.
Figure 2:
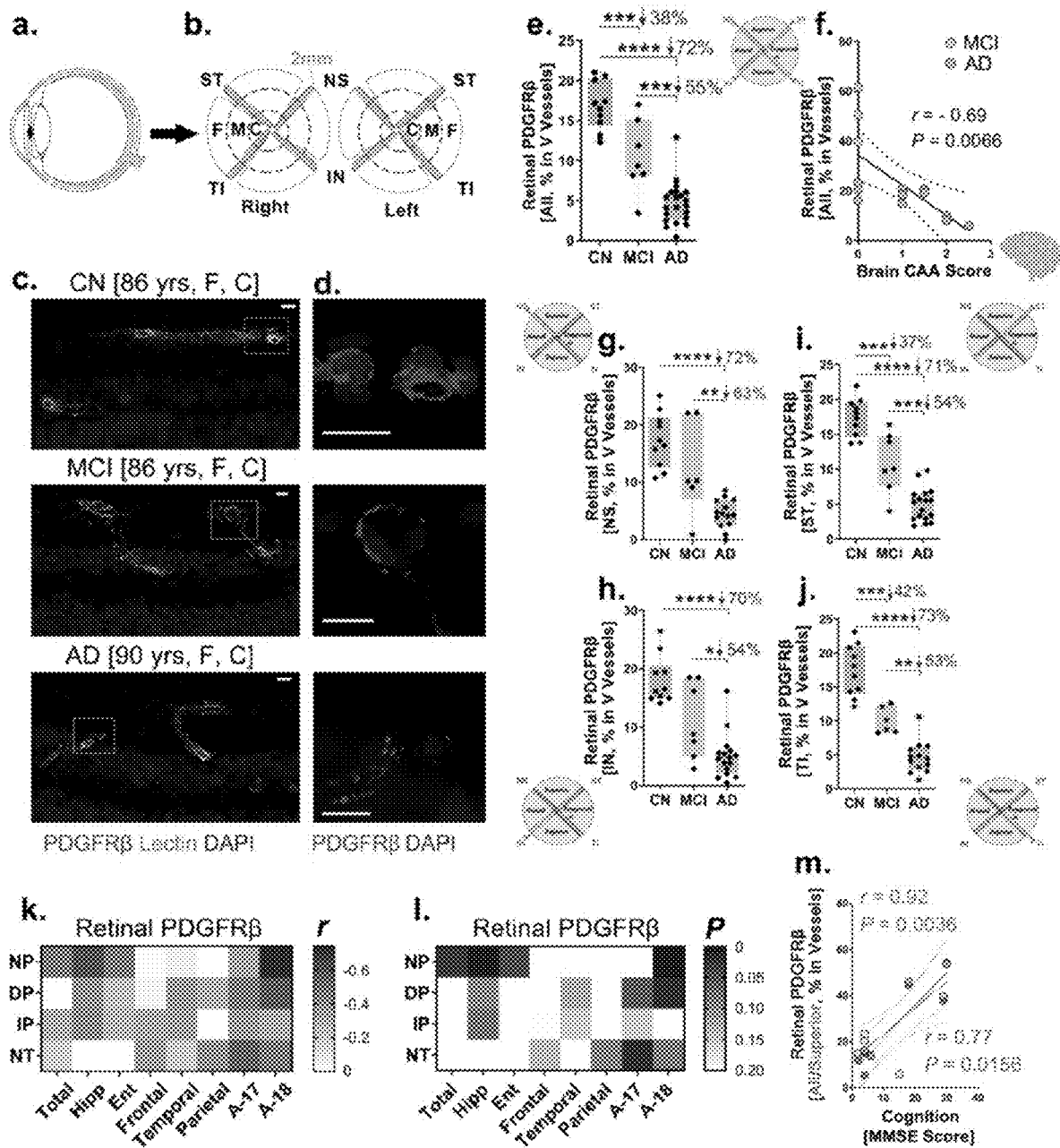
FIG. 2 (panels a-m) shows that early and progressive loss of retinal vascular PDGFRβ in mild cognitive impairment (MCI) and AD. a-b. Schematic diagram of donor eye dissection, isolation of neurosensory retina (yellow), and retinal processing for histological analysis. Anatomically defined strips from all four quadrants, superior-temporal—ST, temporal-inferior—TI, inferior-nasal—IN, and nasal-superior—NS, were prepared and analyzed in pre-determined geometrical regions: central (C), mid—(M) and far—(F) periphery. c-d. Representative fluorescent images of paraffin-embedded retinal cross-sections stained for PDGFRβ (red), with blood vessels (lectin, green) and nuclei (DAPI, blue) in age- and sex-matched human donors with AD, MCI, and cognitively normal (CN; yrs=years; F=female; C=Caucasian). c. Longitudinal (L) blood vessels (~10 μm in diameter); d. Zoomed-in PDGFRβ$^+$ vascular cells are shown from selected regions (dashed white rectangle in c.). Scale bars=10 m. e. Quantitative analysis of percent PDGFRβ IR area in vertical (V) blood vessels in the retinas of donors with AD (n=21), MCI (n=7), and CN (n=10). f. Pearson's coefficient (r) correlation between percent retinal PDGFRβ IR area in sum of V and L blood vessels against CAA scores in a subset of AD (n=11) and MCI (n=3) human donors. g-j. Quantitative analysis of percent PDGFRβ immunoreactive (IR) area in V vessels from each retinal quadrant separately: g. NS, h. IN, i. ST, j. TI, in the same human cohort as in e. k-l. Heat-map illustrating Pearson's correlations between percent retinal PDGFRβ IR area and brain pathology, including neuritic plaques (NP), diffuse plaques (DP), immature plaques (IP), and neuropil threads (NT), in AD (n=14), MCI (n=5) and CN (n=1) human subjects (n=20 total). Pseudo-color k. red for (r) values and l. blue for (P) values demonstrate the strength of each correlation parameter; Total—all brain regions averaged, Hipp—hippocampus, Ent—entorhinal cortex, Frontal—frontal cortex, Temporal—temporal cortex, Parietal—parietal cortex, A-17—primary visual cortex, and A-18—visual association cortex. m. Correlation between percent retinal PDGFRβ IR area of all (mean of four quadrants; grey dots) or superior retinal hemisphere (mean of ST and NS; red dots) against the mini-mental state examination (MMSE) cognitive scores (n=10). Data from individual subjects as well as group mean±SEM are shown. Percent changes are shown in red. *p<0.05, p<0.01, *p<0.001, ****p<0.0001, by one-way ANOVA with Sidak's post-hoc multiple comparison test.

FIG. 26 (panels a-d) shows additional representative images and quantifications for FIG. 1. a-b. Representative images of acellular, degenerated retinal capillaries from a. a 12-month-old wild type (WT) mouse or b. a 12-month-old APPswEIPS1 E9 (ADtg) mouse. Red arrows indicate the degenerated capillaries. Scale bar=20 μm. c-d. Numbers of degenerated retinal capillaries when mice are stratified by mouse age in c. WT or d. ADtg mice groups. Data from individual mice (circles) as well as group means±SEMs are shown. Fold changes are shown in red. Black-filled circles represent males and clear circles represent females. *p<0.05, ****p<0.0001, by one-way ANOVA with Tukey's post-hoc multiple comparison test.

Figure 27:
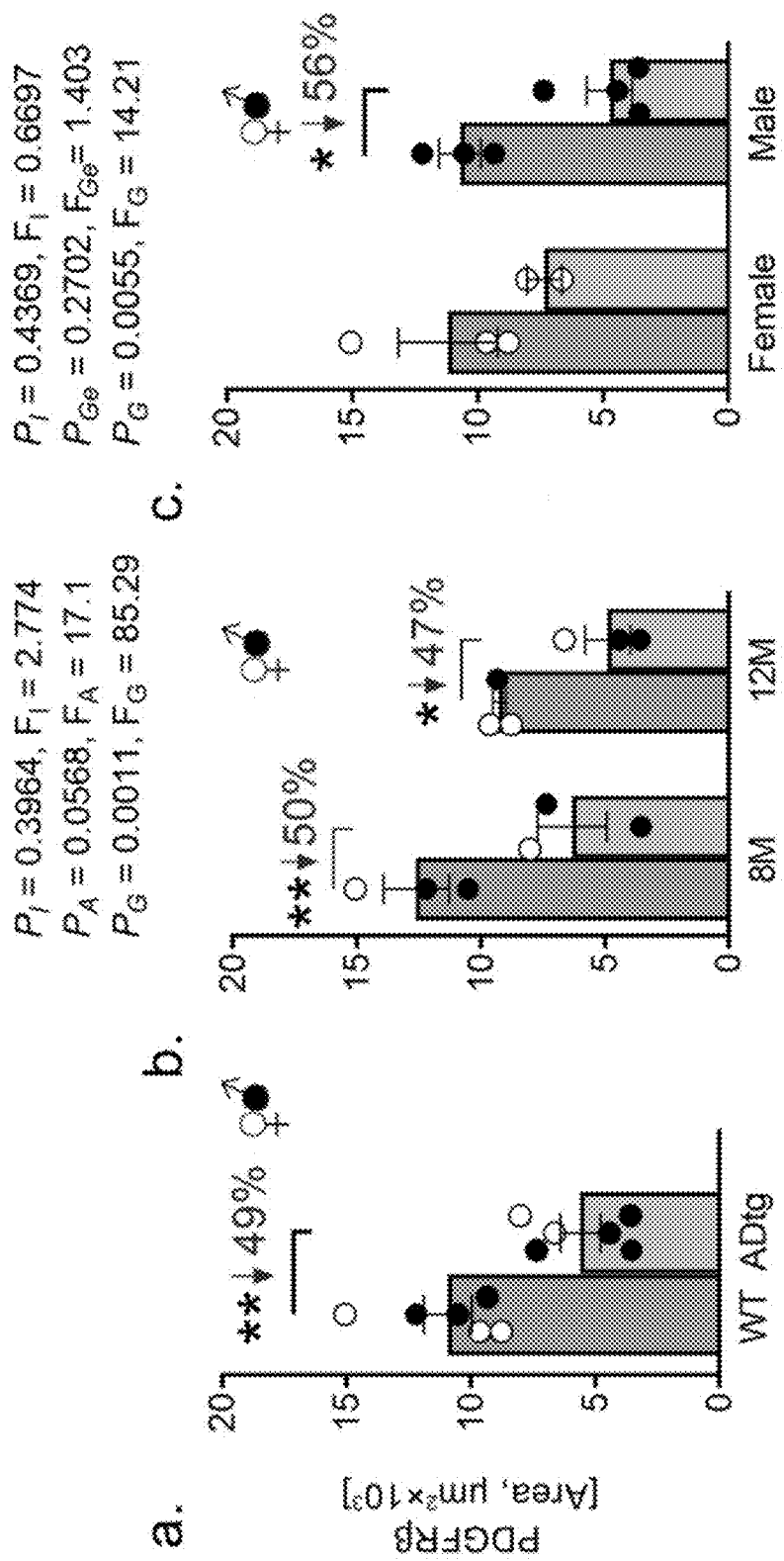

FIG. 27 (panels a-c) shows raw data of quantification of retinal vascular PDGFRr3. a. Quantitative analysis of raw PDGFRr3-immunoreactive (IR) area in each microscopic field of isolated retinal microvasculature from wild type (WT) (n=6) and APPswEIPS1 E9 ADtg (n=6) mice. b. Quantification of PDGFRr3-IR in the same mice cohort when mice are stratified by genotypes of WT and ADtg with b. age of mice by 8 month and 12 month or c. sex of mice. Data from individual mice (circles) as well as from groups are shown with means±SEMs. Black-filled circles represent males and empty circles represent females; *p<0.05, **p<0.01, by two-way ANOVA with Tukey's post-hoc multiple comparison test. Two group statistical analysis was performed using an unpaired 2-tailed Student t-test. Percentage changes are shown in red.

Figure 3:
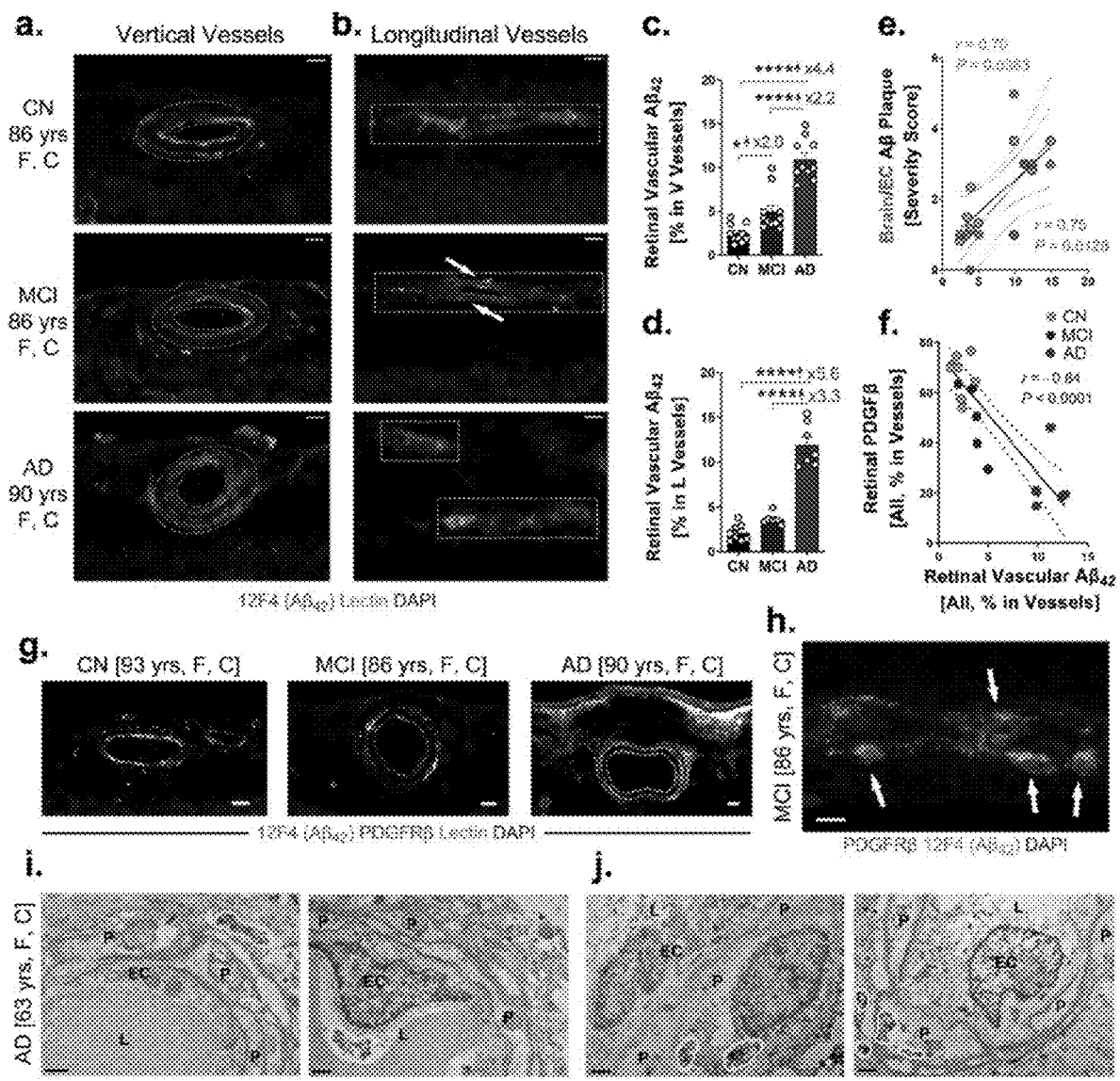
FIG. 3 (panels a-j) shows that increased vascular Aβ$_{42}$ included in pericytes is tightly associated with PDGFRβ loss in postmortem retinas of MCI and AD patients. a-b. Representative fluorescent images of paraffin-embedded retinal cross-sections isolated from human donors with AD, MCI, or cognitively normal (CN) stained for Aβ$_{42}$ (12F4, red), blood vessels (lectin, green), and nuclei (DAPI, blue). a. Vertical (V) and b. longitudinal (L) vessels are shown (yrs=years; F=female; C=Caucasian); geometric shapes in white dashed lines indicate pre-defined areas of analysis. Scale bars=10 μm. c-d. Quantitative analysis of percent 12F4 immunoreactive (IR) area in retinal c. V or d. L blood vessels in age- and sex-matched human donors with AD (n=10), MCI (n=11) and CN (n=10). e-f. Pearson's coefficient (r) correlation between retinal 12F4+Aβ$_{42}$ burden in average of V and L blood vessels against e. neuritic Aβ plaques either in whole brain (grey dots) or entorhinal cortex (EC; red dots) and f. percent retinal vascular PDGFRβ IR area within a subset of human donors with AD, MCI and CN (n=8, n=10, and n=18, respectively). g. Representative fluorescent images of retinal vertical vessels from human eye donors with AD, MCI, or CN, stained for Aβ$_{42}$ (12F4, white), PDGFRβ (red), blood vessels (lectin, green), and DAPI for nuclei (blue). Scale bars=10 μm. h. A microscopic image of longitudinal vessel from MCI retina showing vascular Aβ$_{42}$ immunoreactivity (green) co-localized with PDGFRβ$^+$ cells (red, arrows). Scale bars=10 μm. i-j. Transmission electron microscopy (TEM) images of retinal vertical-sections from an AD human donor; retina was pre-stained with anti-Aβ$_{42}$ mAb (12F4) and an immunoperoxidase-based DAB. TEM analysis reveals the location and ultrastructure of retinal vascular-associated Aβ deposits (demarcated by yellow shapes). i. Left, retinal Aβ$_{42}$ deposit in the outer vascular surface adjacent to pericytes (P, green), with a clean blood vessel lumen (L). Right, retinal Aβ$_{42}$ deposited inside a blood vessel lumen attached to an endothelial cell (EC, pink) surface. j. Retinal Aβ$_{42}$ deposits within pericytes, detected in the cytoplasm and adjacent to mitochondria, as well as on vessel outer surface external to the pericytes. Scale bars=0.5 μm. Data from individual human donors as well as group mean±SEM are shown. Fold changes are shown in red. *p<0.05, p<0.01, *p<0.001, ****p<0.0001, by one-way ANOVA with Sidak's post-hoc multiple comparison test.
Figure 28:
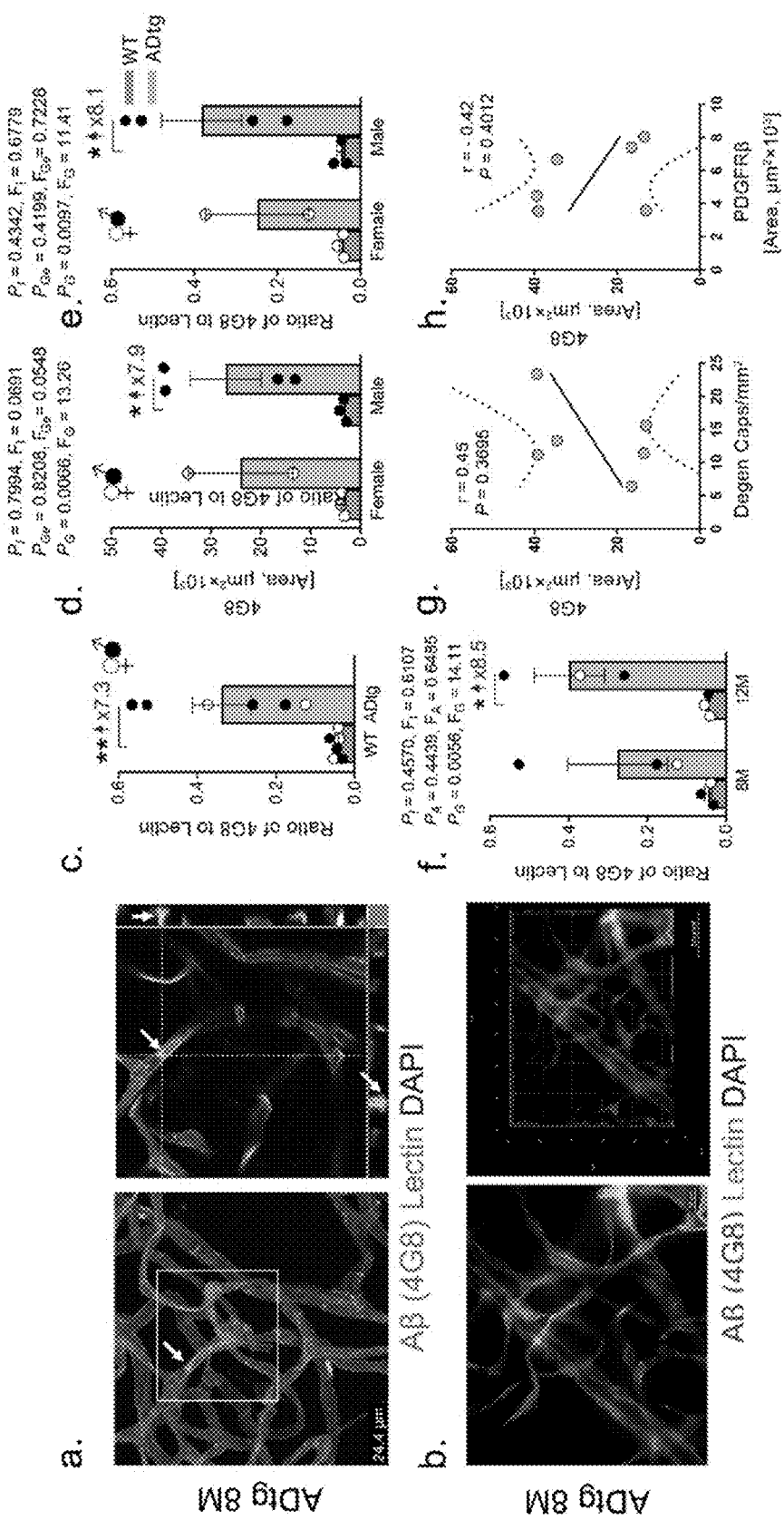
Figure 28:
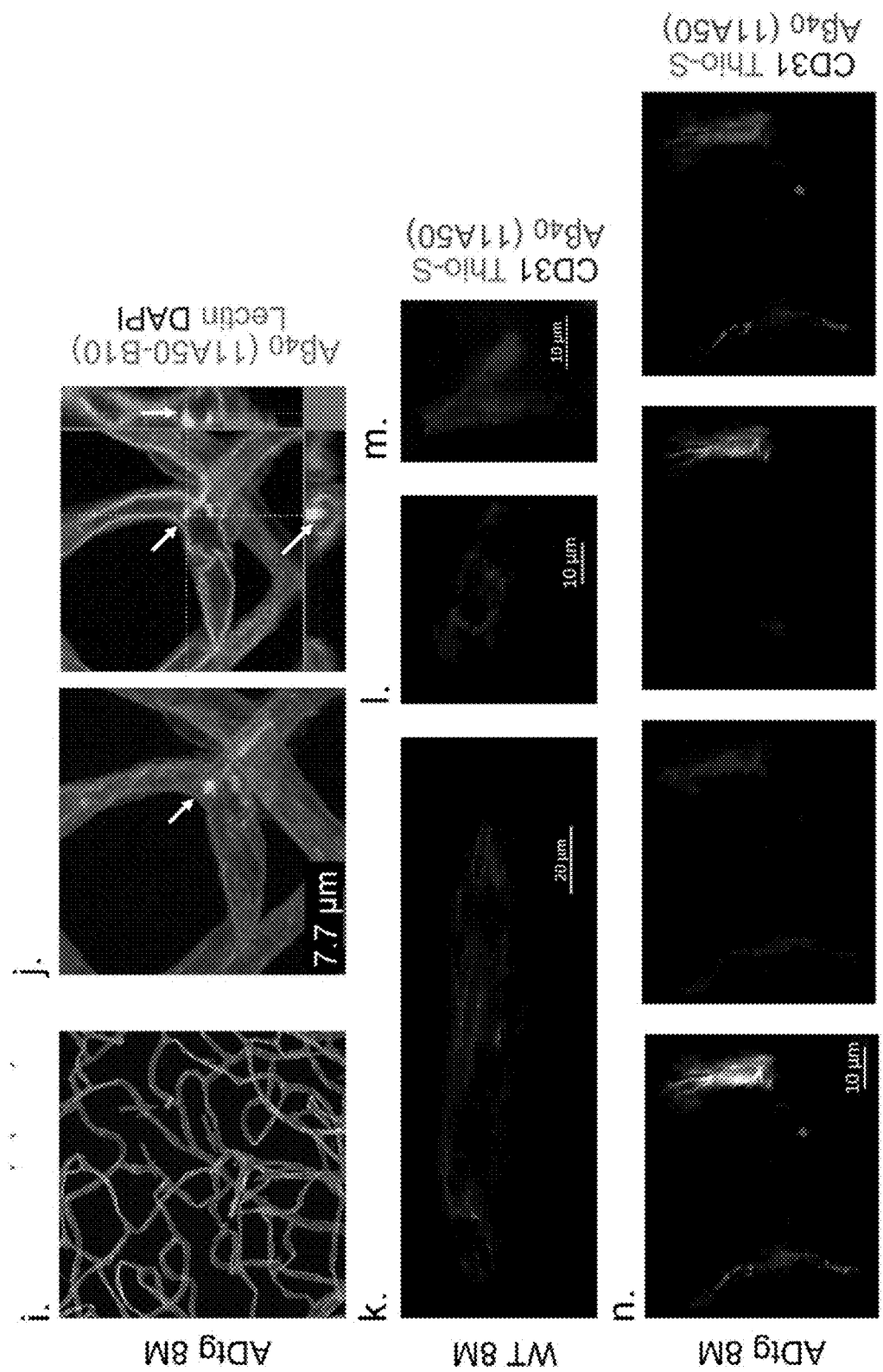

FIG. 28 (panels a-n) shows supplementary images, quantifications and correlations for FIG. 3. a-b. Representative fluorescence images of isolated retinal microvasculature stained for A (4 GB, magenta or red, as indicated under the images), blood vessels (lectin, green), and nuclei (DAPI, blue) in a perfused 8-month-old APPswE/PS1 t, E9 (ADtg) mice. Arrows indicate vascular A. c. Quantitative analysis of the A (4G8)-immunoreactive (IR) area normalized by lectin area in each microscopic field of isolated retinal microvasculature from wild type (WT) (n=6) or ADtg (n=6) mice. d-e. Quantitative analysis of the d. A (4G8)-IR area or e. A (4G8)-IR area normalized by lectin area in each microscopic field of isolated retinal microvasculature from the same cohort separated by different sex of mice. f. Quantitative analysis of the A (4G8)-IR area normalized by lectin area separated by different mice age groups (8 months and 12 months) and genotypes (WT and ADtg) in the same cohort. n=3 for each group. g-h. Pearson's coefficient (r) correlation between the retinal A (4G8)-IR area against g. degenerated capillaries or h. PDGFR-IR area in ADtg mice (n=6) of this cohort. i-j. Representative fluorescence images of isolated retinal microvasculature stained for A 40 (11A50-B10, magenta), blood vessels (lectin, green), and nuclei (DAPI, blue) in a perfused 8-month-old ADtg mice. Arrows indicate vascular A. k-n. Representative fluorescence images of retinal cross-section for thioflavin-S (Thio-S, green), A 40 (11A50-B10, red) and blood vessels (CD31, blue) in a perfused 8-month-old k-m. WT or n. ADtg mice. Data from individual mice (circles) as well as from groups are shown with means±SEMs. Black-filled circles represent males and empty circles represent females; *p<0.05, **p<0.01, by two-way ANOVA with Tukey's post-hoc multiple comparison test. Two group statistical analysis was performed using an unpaired 2-tailed Student t-test. Fold changes are shown in red.

Figure 4:
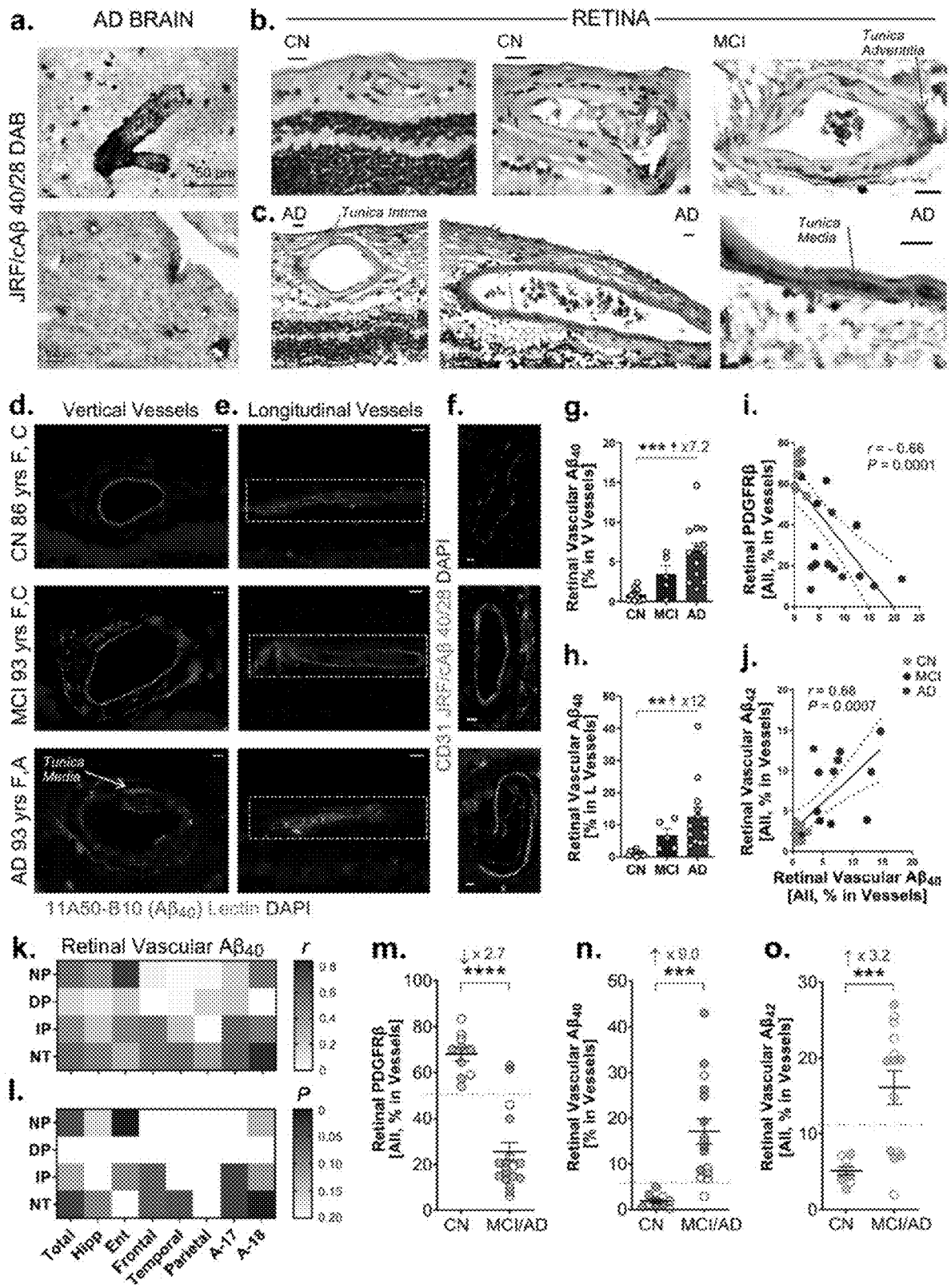
FIG. 4 (panel a-o) shows that retinal vascular Aβ$_{40}$ burden in AD retina correlates with both retinal vascular Aβ$_{42}$ deposits and PDGFRβ loss and can predict disease status. a-c. Representative images of retinal and brain sections immunostained against Aβ$_{40}$ (JRF/cAβ$_{40/28}$; #8152) with DAB labeling and hematoxylin counterstain in cohorts of AD, MCI, and cognitively normal (CN) controls. c. Arrows indicate vascular Aβ$_{40}$ staining in tunica media, adventitia, or intima; right image is an enlargement of area indicated by arrow from the middle image. Scale bars=20 μm. d-e. Representative fluorescent images of paraffin-embedded retinal cross-sections isolated from human donors with AD, MCI, or CN (yrs=years old; F=female; C=Caucasian; A=Asian) and stained for Aβ$_{40}$ (11A50-B10, red), blood vessels (lectin, green), and nuclei (DAPI, blue) in d. vertical (V) and e. longitudinal (L) retinal blood vessels. Dashed geometric white shapes indicate pre-defined areas of analysis. Scale bars=10 μm. f. Representative microscopic images showing V vessels labeled against endothelial cells (CD31, red), Aβ$_{40}$ (JRF/cAβ$_{40/28}$, green), and nuclei (DAPI, blue) in retinas from AD, MCI, and CN human donors. Scale bars=10 μm. g-h. Quantitative analysis of percent 11A50-B10+Aβ$_{40}$ immunoreactive (IR) area in retinal g. V and h. L blood vessels from AD (n=13), MCI (n=5) and CN controls (n=10). i-j. Pearson's coefficient (r) correlation between retinal Aβ$_{40}$ burden (mean of both V and L vessels) against i. percent retinal PDGFRβ IR area (n=24 human donors) or j. percent retinal vascular 12F4+Aβ$_{42}$ burden (n=20 human donors). k-l. Heat-map illustrating correlations between percent retinal vascular Aβ$_{40}$ IR area (average of V and L blood vessels) against brain pathology, including neuritic plaques (NP), diffuse plaques (DP), immature plaques (IP), and neuropil threads (NT), in AD (n=8), MCI (n=3), and CN (n=1) human donors (n=12 total). Pseudo-color k. red (r) values and l. blue (P) values demonstrate the strength of each correlation parameter; total—average of all brain regions, Hipp—hippocampus, Ent—entorhinal cortex, Frontal—frontal cortex, Temporal—temporal cortex, Parietal—parietal cortex, A-17—primary visual cortex, and A-18—visual association cortex. m-o. Analysis of retinal parameters when samples are stratified per two diagnostic groups, MCI/AD and CN. m. Retinal vascular PDGFRβ (n=20 MCI/AD and n=10 CN). n. Retinal vascular Aβ$_{40}$ (n=16 MCI/AD and n=10 CN). o. Retinal vascular Aβ$_{42}$ (n=14 MCI/AD and n=9 CN). Dotted lines display the suggested values to separate between control and disease groups. Males in filled circles and Females in clear circles. Data from individual human subjects as well as group mean±SEM are shown. Fold and percent changes are shown in red. $p<0.01$, *$p<0.001$, ****$p<0.0001$, by one-way ANOVA with Sidak's post-hoc multiple comparison test.
Figure 29:
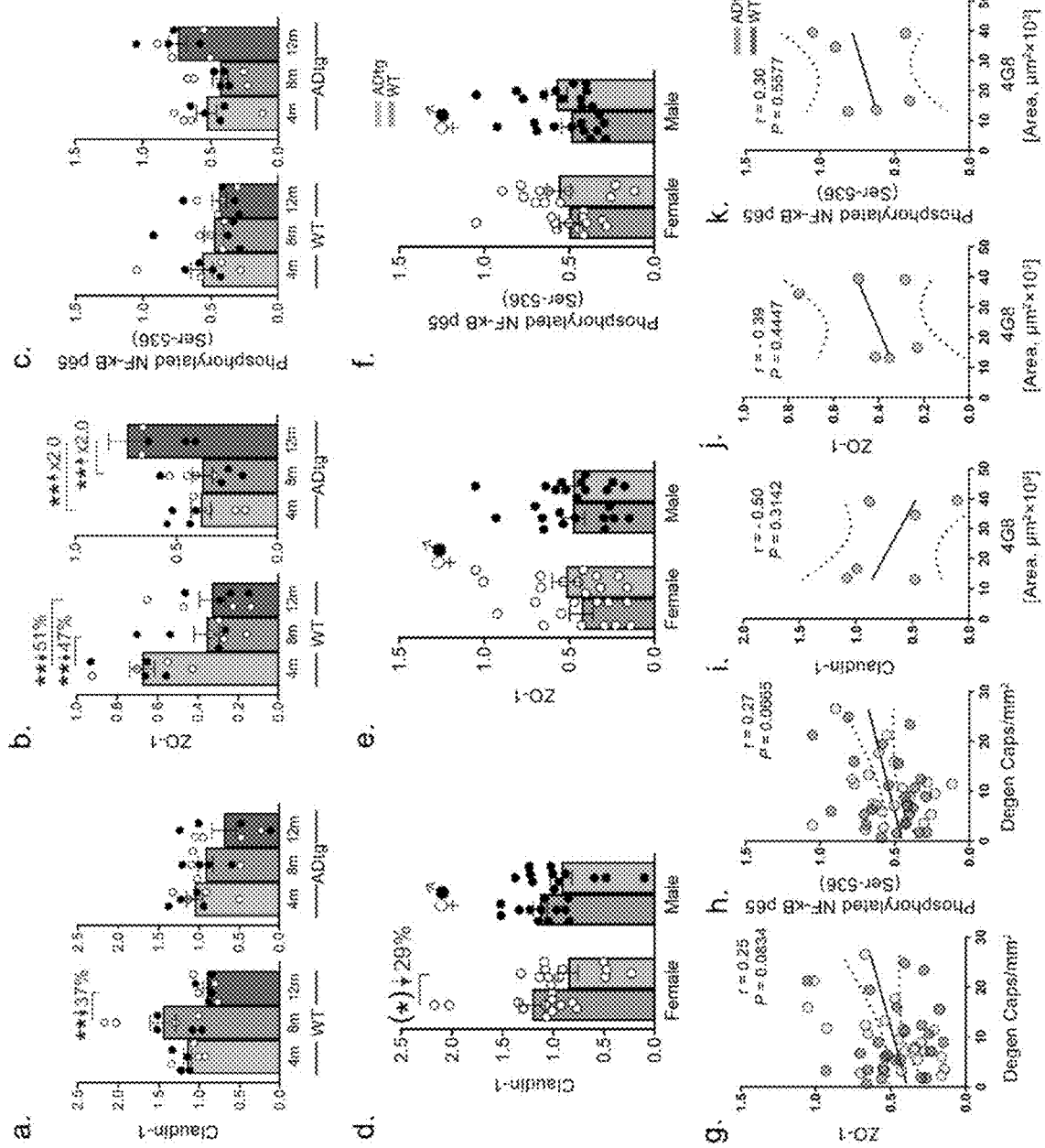

FIG. 29 (panels a-k) shows additional data for FIG. 4. a-c. Densitometric analysis of western blot protein bands of a. claudin-1, b. ZO-1, and c. pNF-κB p65 with normalization, separated by mice age (4, 8, and 12 months) and genotype (WT and ADtg) in the same mice cohort as FIG. 4. n=8 for each group. d-f. Densitometric analysis of western blot protein bands of d. Claudin-1, e. ZO-1 and f. pNF-κB p65 in the same mice cohort (n=12 for each group) separated by sex. Data from individual mouse (circles) as well as groups are shown as means±SEMs. Black circles represent males and clear circles represent females. *p<0.05, **p<0.01, by one-way or two-way ANOVA with Tukey's post-hoc multiple comparison test. Two group statistical analysis was done by an unpaired 2-tailed Student t-test, and is shown in parenthesis. Percentage and fold changes are shown in red. g-h. Pearson's coefficient (r) correlation between retinal degenerated capillaries (Degen Caps) and the densitometric analysis of western blot protein bands of g. ZO-1, or h. pNF-κB p65 in the same mice cohort of FIG. 4 (n=48). i-k. Pearson's coefficient (r) correlation between retinal 4G8-immunoreactive area and the densitometric analysis of western blot protein bands of i. claudin-1, j. ZO-1, or k. pNF-κB p65 in a subset of the APPswEIPS1 E9 (ADtg) mice cohort in FIG. 4 (n=6).

Figure 5:
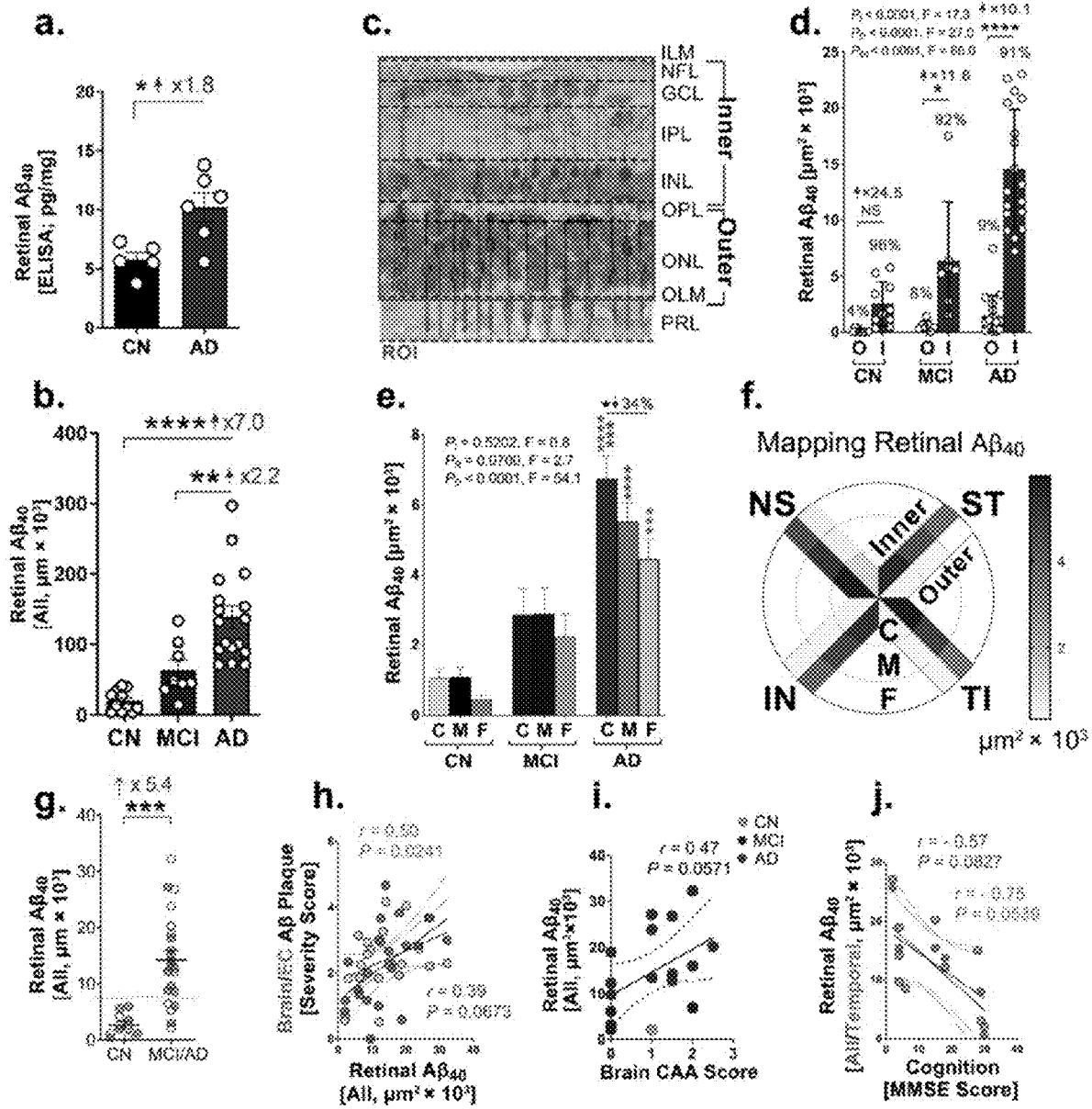
FIG. 5 (panels a-j) shows mapping of retinal Aβ$_{40}$ burden and distribution in predefined geometrical regions and layers. a. Retinal Aβ$_{1-40}$ concentrations determined by ELISA assay in protein homogenates from postmortem retinas freshly collected from AD patients (n=6) and cognitively normal controls (CN, n=5). b. Quantitative analysis of 11A50-B10+Aβ$_{40}$ immunoreactive (IR) area normalized to retinal thickness in cross-sections from a cohort of AD (n=17), MCI (n=8), and CN controls (n=11). c. Schematic diagram for the region of interest (ROI) analyzed with separate assessments for inner (from inner limiting membrane=ILM to inner nuclear layer=INL) and outer neural retina (from outer plexiform layer=OPL to outer limiting membrane=OLM). d. Quantitative analysis of Aβ$_{40}$ IR area in outer (O) vs. inner (I) retina of AD (n=17), MCI (n=8), and CN (n=11) human donors. e. Quantitative analysis of Aβ$_{40}$ IR area in central (C), mid-peripheral (M), and far-peripheral (F) retina from the same human cohort. f. Mapping of Aβ$_{40}$ in four quadrants, C/M/F, and inner vs. outer retina. Strength of magenta pseudo-color represents the density of retinal Aβ$_{40}$ burden in each geographic region. g. Analysis of retinal parameters when samples are stratified per two diagnostic groups, MCI/AD and CN for total retinal Aβ$_{40}$ (n=22 MCI/AD and n=10 CN). Dotted lines display the suggested values to separate between control and disease groups. Males in filled circles and Females in clear circles. h-j. Pearson's coefficient (r) correlation between retinal Aβ$_{40}$ IR area against h. neuritic Aβ plaques in whole brain (grey dots) and entorhinal cortex (EC, red dots), i. CAA scores, and j. mini-mental state examination (MMSE) cognitive scores (grey dots—all retina, red dots—temporal retina=mean of ST and TI quadrants) in different subsets of AD, MCI, and CN human donors (n=20, n=17 or n=10, respectively). Data from individual human subjects as well as group mean±SEM are shown. Fold and percent changes are shown in red. *$p<0.05$, $p<0.01$, *$p<0.001$, ****$p<0.0001$, by one-way or two-way ANOVA with Sidak's post-hoc multiple comparison test (Red * in e indicates AD vs. CN group, blue * in e indicates AD vs. MCI group). Two group statistical analysis of ELISA was done by unpaired 2-tailed Student's t test.
Figure 6:
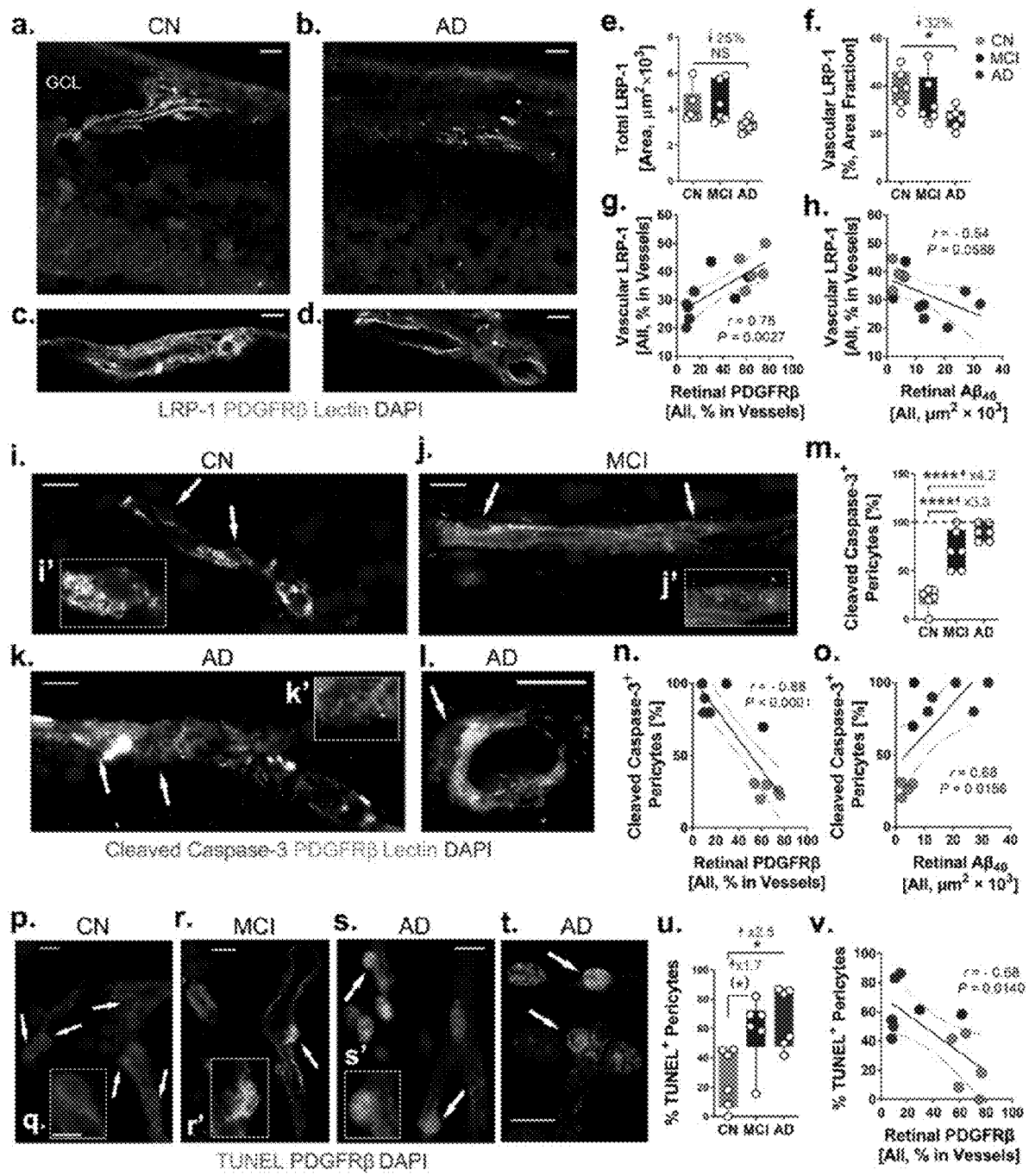
FIG. 6 (panels a-v) shows decreased retinal LRP-1 in AD and increased apoptotic pericytes in MCI and AD retina. a-b. Representative fluorescent images of paraffin-embedded retinal cross-sections isolated from a. cognitively normal (CN) and b. AD subjects, stained for LRP-1 (red), PDGFRβ (green), blood vessels (lectin, white), and nuclei (DAPI, blue). c-d. Representative fluorescent images from AD and CN subjects focusing on retinal vascular LRP-1 region. e. Quantitative analysis of total LRP-1 immunoreactive (IR) area in postmortem retinas from patients with AD (n=6), MCI (n=6), and from CN controls (n=6). f. Quantitative analysis of percent LRP-1 IR area in retinal blood vessels from the same cohort. g-h. Pearson's coefficient (r) correlation between percent retinal LRP-1 IR area in the vasculature against g. percent retinal vascular PDGFRβ IR area, and h. total retinal 11A50-B10+ Aβ$_{40}$ area in a subset of human cohorts (n=13 and n=12, respectively). i-l. Representative fluorescent images of paraffin-embedded retinal cross-sections isolated from i. CN, j. MCI, or k-l. AD human eye donors, stained for cleaved caspase-3 (red), PDGFRβ (green), blood vessels (lectin, white), and nuclei (DAPI, blue). Arrows indicate positive signal of cleaved caspase-3 in pericytes. i'-k' show zoomed-in pericytes from the original image. m. Quantitative analysis of percent cleaved caspase-3+ pericyte number out of 10-15 pericytes counted from each human donor: AD (n=6), MCI (n=6), and CN (n=6). Dashed line represents 100% reference point. n-o. Pearson's coefficient (r) correlation between percent cleaved caspase-3+ pericytes against n. retinal vascular percent PDGFRβ IR area or o. total retinal 11A50-B10+ Aβ$_{40}$ IR area in a subset of human donors (n=11). p-t. Representative fluorescent images of paraffin-embedded retinal cross-sections isolated from human donors either p-q. CN, r. MCI, or s-t. AD, stained for PDGFRβ (red), TUNEL (green) and nuclei (DAPI, blue). r'-s' show zoomed-in retinal TUNEL+ pericytes from the original images of MCI and AD donors. u. Quantitative analysis of percent retinal TUNEL+ pericytes in 10-15 pericytes counted from each donor from the same human cohort. v. Pearson's coefficient (r) correlation between percent TUNEL+ pericytes and percent vascular PDGFRβ IR area in postmortem retinas from a subset of human donors (n=12). All scale bars=10 μm. Data from individual human donors as well as group mean±SEM are shown. Fold and percentage changes are shown in red. *$p<0.05$, ****$p<0.0001$, NS=not significant, by one-way ANOVA with Sidak's post-hoc multiple comparison test. *$p<0.05$ in parenthesis=unpaired 2-tailed Student's t test.

FIG. 30 (panels a-b) shows additional representative images for FIG. 5. a-b. Representative images of noninvasive retinal microvascular imaging after intraperitoneal fluorescein injection in a. 16-month-old APPswEIPS 1b.E9 (ADtg) and b. 8-month-old ADtg mice.

Figure 31:
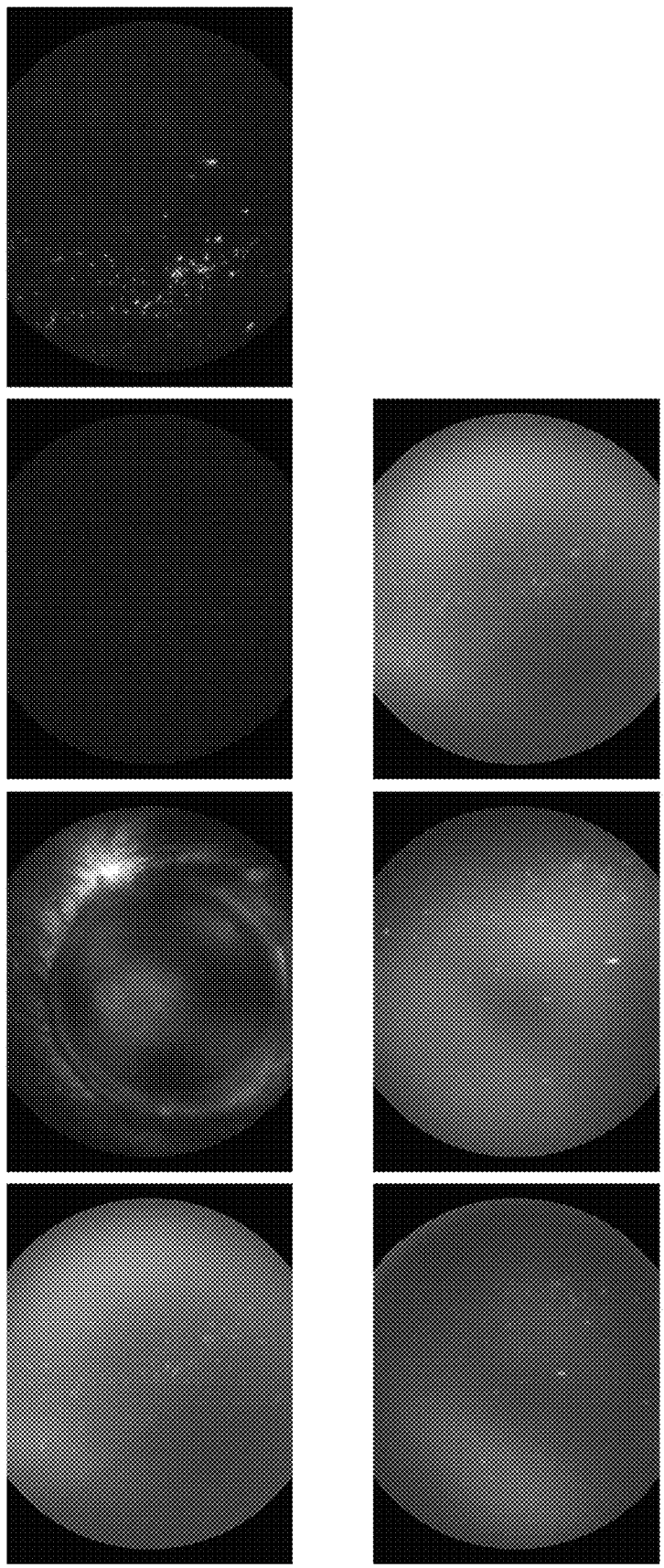

FIG. 31 shows images of pericytes taken by using a noninvasive Micron-III retinal rodent imaging microscope, 5 minutes after injection of Green Fluorescent Nissl Stain into a wild type mouse for imaging vascular pericytes.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., Revised, J. Wiley & Sons (New York, NY 2006); March, *Advanced Organic Chemistry Reactions, Mechanisms and Structure* $7^{th}$ ed, J. Wiley & Sons (New York, NY 2013); and Sambrook and Russel, *Molecular Cloning: A Laboratory Manual* $4^{th}$ ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein the term "about" when used in connection with a referenced numeric indication means the referenced numeric indication plus or minus up to 5% of that referenced numeric indication, unless otherwise specifically provided for herein. For example, the language "about 50%" covers the range of 45% to 55%. In various embodiments, the term "about" when used in connection with a referenced numeric indication can mean the referenced numeric indication plus or minus up to 4%, 3%, 2%, 1%, 0.5%, or 0.25% of that referenced numeric indication, if specifically provided for in the claims.

Described herein, we combined fluorescent immunostaining of isolated human retinal vasculature after elastase-based enzymatic digestion of non-vascular tissue to evaluate retinal vascular Aβ deposition and pericyte loss in AD as compared to cognitively normal (CN) controls. We further analyzed a larger cohort (n=56) of postmortem retinal cross-sections and freshly collected retinas from patients with MCI and AD, and compared with age- and sex-matched CN controls. We assessed AD-related pathology in blood vessels across central and peripheral geometrical subregions and layers in pre-defined retinal quadrants. Quantitative analyses were conducted for retinal vascular PDGFRβ expression in pericytes/vSMCs, vascular $A\beta_{42}$ burden, abluminal and vascular $A\beta_{40}$ burden, apoptotic cell markers in pericytes, and retinal LRP-1 expression. Importantly, we compared these retinal parameters with the respective brain pathology and cognitive status. Our findings indicate that along with the substantial increase in retinal vascular amyloidosis in postmortem retinas from AD patients, there was an early and progressive loss of retinal vascular PDGFRβ in pericytes and vSMCs that associated with AD pathology in the brain.

Described herein, we identified cellular and molecular changes involved in retinal vascular pathology in AD. Elastase-based enzymatic digestion, isolation, and clearance of retinal vascular network was applied to prevent possible interference of abluminal retinal tissue. This approach revealed the localization of retinal Aβ deposits within blood vessels, measured their accumulation including within pericytes, and established retinal pericyte loss in postmortem retinas of AD patients. Using murine models of AD and comparing between isolated retinal blood vessels from perfused and non-perfused animals, we demonstrated accumulation of Aβ in blood vessels, regardless of circulating Aβ in the blood. In a larger cohort of human eye donors, we mapped and quantitatively assessed various AD-related vascular parameters, such as PDGFRβ expression and Aβ burden, in anatomically pre-defined retinal subregions and layers. In the analysis of vertical blood vessels, by avoiding Aβ signal in the lumen, which may have originated from blood circulation, we were able to detect increased retinal vascular $A\beta_{40}$ and $A\beta_{42}$ burdens in AD. We also demonstrated the existence of retinal Aβ accumulation in three layers of blood vessel walls.

We also identified early and progressive loss of pericytes and vascular PDGFRβ expression in postmortem retinas from MCI and AD patients. Deficient PDGFRβ expression in the AD retina was tightly linked with increased retinal vascular $A\beta_{40}$ and $A\beta_{42}$ burden, and, importantly, was associated with CAA severity scores, brain Aβ plaques, and cognitive status. Along with elevated vascular amyloid deposits, retinal blood vessel cells had reduced LRP-1 expression and retinal pericytes showed elevated apoptotic biomarkers (cleaved caspase-3 and TUNEL), suggesting that vascular retinal pericytes undergo apoptosis and may have impaired LRP-1-mediated A clearance in the AD retina. Our findings of early and extensive Aβ-associated retinal vascular PDGFRβ pericyte degeneration in MCI and AD mirrors a prominent feature of brain AD pathology. This feature was implicated in progressive BBB abnormalities, including insufficient Aβ clearance and neuronal damage. Together with previous identification of Aβ deposits and p-tau in the retina of AD patients, these novel retinal vascular findings further establish the retina as a tissue affected by AD. Given that the neurosensory retina is an extension of the brain and far more accessible for visualization via noninvasive imaging at sub-cellular resolution, the current study and finding described herein contribute to the understanding of retinal vascular pathophysiology of AD and provide for next-generation retinal biomarker imaging for AD.

In our cohort, an early increase of retinal $A\beta_{42}$ deposits in vertical vessel walls (with lumen exclusion) was detected in MCI as compared to CN controls. This result, together with vascular $A\beta_{42}$ levels already notable in CN individuals, suggest early retinal vascular $A\beta_{42}$ deposits in the AD continuum and perhaps less efficient clearance compared to retinal Aβ 40. Although both Aβ alloforms exhibit increased trends in retinal blood vessels of MCI when compared to CN, the fold changes in vascular $A\beta_{40}$ between AD vs. CN controls were substantially higher than the respective increases for vascular $A\beta_{42}$. These data indicate that during AD pathogenesis, $A\beta_{40}$ is more prominently elevated in retinal blood vessels than $A\beta_{42}$. Future studies should evaluate which alloform, $A\beta_{40}$ or $A\beta_{42}$ in blood vessels, accumulates earlier in the retina and may affect vascular abnormalities related to AD.

Importantly, the correlations between both vascular Aβ alloforms and PDGFRβ loss were significant, with a stronger correlation to $A\beta_{42}$, possibly due to increased $A\beta_{42}$ toxicity to pericytes. In murine models of AD, brain $A\beta_{42}$ was detected within pericytes and was associated with pericyte loss. Further supporting this idea is our observation that retinal $A\beta_{42}$ in MCI and AD is found inside residual punctate-stained PDGFRβ$^+$ pericytes. A similar phenomenon was described in cerebral pericytes which were involved in $A\beta_{42}$ clearance. Other evidence for deposition of $A\beta$ in retinal pericytes was provided in this study from quantification of $A\beta$ in pericytes of isolated retinal blood vessels, and by utilizing TEM analysis on retinal vertical section. These findings suggest that similar to the brain, retinal pericytes may be susceptible to $A\beta_{42}$ toxicity and play a role in its clearance in the retina. Nonetheless, these phenomena with possible implications to retinal $A\beta_{40}$ and $A\beta_{42}$ clearance mechanisms are poorly understood and warrant future investigations.

Our results have shown early and intense apoptosis of pericytes, as well as a decrease in PDGFR expression in pericytes and vSMCs. Brain pericytes and vSMCs are critical in regulating blood flow and BBB integrity. Since PDGFRβ is expressed by both pericytes and vSMCs and its signaling pathway is crucial for regulating pericyte recruitment, our results of PDGFRβ loss in postmortem retina from MCI patients suggest an early compromised vascular integrity during the AD continuum, similar to that found in the brain. Previously, brain pericyte loss and BBB breakdown were reported in AD patients. Additionally, in PDGFRβ$^{F7/F7}$ mice, PDGFRβ deficiency led to brain pericyte reduction, resulting in both microvascular disruption and loss. While vSMC actin was found to be reduced in AD brains, another report demonstrated disrupted PDGFRβ signaling and pericyte loss in PDGFRβ$^{F7/F7}$ mice with no vSMC loss. In the current study, we noted loss of retinal PDGFRβ staining in both vertical and longitudinal blood vessels, suggesting that both pericytes and vSMCs are affected in AD. Based on the separate analysis of small-size longitudinal capillaries and post-capillary venules, our data indicate substantial retinal PDGFRβ losses in pericytes from MCI and AD. The analysis of vertical vessels suggested significant retinal PDGFRβ losses in both pericytes and vSMCs.

Previous studies identified a LRP-1-dependent mechanism of cerebral $A\beta_{42}$ clearance in both brain vSMCs and pericytes. Cerebral LRP-1-mediated $A\beta_{40}$ and $A\beta_{42}$ clearance through apolipoprotein E isoforms-specific mechanism was further identified for PDGFRβ$^+$ pericytes. In addition, a reduction in LRP-1 levels was reported in AD brains along with significant decreases in cortical neurons and vascular structures. In our study described herein, a significant decrease (32%) of vascular LRP-1 expression was detected in postmortem retinas from AD patients. Together with this significant decrease, the trend of correlation between retinal vascular LRP-1 reduction and retinal $A\beta_{40}$ accumulation may implicate a compromised retinal LRP-1-mediated $A\beta_{40}$ clearance. These findings warrant future exploration of whether LRP-1 loss occurs later in disease progression, as a result of $A\beta$ deposition, pericyte degeneration, or other earlier vascular abnormalities in the AD retina.

We found that retinal vascular amyloid burden consists of $A\beta_{42}$ and $A\beta_{40}$ alloforms, which is comparable to CAA composition in AD and MCI patients. Although both $A\beta_{42}$ and $A\beta_{40}$ are involved in CAA development, $A\beta_{40}$ has long been known to be the main alloform, and its accumulation associates with CAA progression. Hence, due to its primary involvement in vascular amyloidosis and its distribution in various retinal layers, we quantified and mapped the spatial and layer distribution of total retinal $A\beta_{40}$ burden. Importantly, the existence of retinal $A\beta_{1-40}$ peptide was validated by a highly sensitive and specific sandwich ELISA and its significant accumulation in the temporal hemiretina of AD versus CN controls was demonstrated. Moreover, elevated $A\beta_{40}$ burden in blood vessels from AD donors was further confirmed by commercial and proprietary (JRF/cA$\beta_{40/28}$) monoclonal antibodies specific to the C-terminal amino acid sequence of $A\beta_{40}$ peptides, detected by both fluorescent and non-fluorescent labeling methods. Our results in postmortem retinas from MCI and AD patients show that $A\beta_{40}$ deposition is detected in three layers of the vessel wall: tunica intima, media, and adventitia. Overall, the increased retinal $A\beta_{40}$ burden may suggest $A\beta$-mediated toxicity to vascular cells that could lead to complications similar to CAA, including vessel wall fragmentation and blood leakage. Future studies should address this possibility.

Here, we observed a 7-fold increase in total $A\beta_{40}$ burden in postmortem retinas of AD patients as compared to CN individuals, which was comparable with the increase in vascular $A\beta_{40}$ burden. The significant correlation between the two parameters suggests that retinal vascular $A\beta_{40}$ burden may be an outcome of total retinal $A\beta_{40}$ accumulation. The abundance of apoptotic cell markers, TUNEL and cleaved caspase-3, in the nuclei of retinal pericytes of both MCI and AD, and the correlations with PDGFRβ loss and $A\beta_{40}$ burden, may indicate that some aspects of retinal vascular abnormality are linked with increased total $A\beta_{40}$ burden in the retina. All four retinal quadrants exhibited significantly higher total retinal $A\beta_{40}$ burden in the AD group compared to both MCI and CN groups, with the highest 9.7-fold increase observed in the TI quadrant. Further, levels of $A\beta_{40}$ in central retinal subregions were significantly higher compared to those measured in retinal far-periphery of AD. Importantly, over 90% of $A\beta_{40}$ burden was concentrated in the inner retina compared to the outer retina, with signs of propagation from inner to outer retina during disease progression. These data corroborate previous observations of frequent $A\beta$ deposits in inner retinal layers of AD and may explain excessive degeneration seen in RGCs and RNFL, as detected by histology and OCT. The buildup of $A\beta_{40}$ in the central and inner retinal layers follows the pattern of highly dense retinal blood vessels in these regions and strengthens the possible link between $A\beta$ accumulation, toxicity, and blood vessel disruptions. In addition, the substantial loss of PDGFRβ, especially in the ST and TI quadrants, that colocalized with retinal vascular amyloidosis, and previous corroborating data indicating significant abnormalities in the ST and TI regions, imply that inner cellular layers in the central temporal hemiretina are more susceptible to AD pathological processes.

Retinal vascular $A\beta$ 40, vascular $A\beta_{42}$, and total $A\beta_{40}$ parameters appeared to correlate significantly with retinal PDGFRβ loss, suggesting their independent role in pericyte/vSMC toxicity and that the loss of these vascular cells may have direct effects on $A\beta$ clearance and its vascular accumulation. Unexpectedly, retinal vascular $A\beta_{42}$ correlated significantly with CAA scores whereas retinal vascular and total $A\beta_{40}$ only showed trends of significance with CAA severity. The limitation of these correlations is that the neuropathological reports with CAA scores were available for a smaller subset of human donors. Nevertheless, these findings possibly point to shared mechanisms of retinal and cerebral vascular $A\beta_{42}$ accumulation, but independent mechanisms of vascular $A\beta_{40}$ accumulation in the retina. It is intriguing that both vascular alloforms significantly correlated with $A\beta$ plaque burden in the hippocampus, entorhinal cortex, and visual cortex—brain regions highly impacted by AD. Further, our data indicated retinal vascular PDGFRβ and Aβ$_{40}$ burden as leading parameters to distinguish between MCI/AD and CN diagnostic groups, suggesting they may predict AD status. Given the morphological and physiological similarities between the blood-retinal barrier (BRB) and BBB, the loss of PDGFRβ$^+$ pericytes along with Aβ deposits in retinal microvasculature and the associations with CAA and cognitive status point to the connection between retinal and brain pathology in AD.

To summarize, this study identifies early and progressive pericyte loss, compromised PDGFRβ expression, and vascular Aβ accumulation in postmortem retina of MCI and AD patients along with their significant correlation to cerebral pathology and cognitive decline. These results extensively impact our knowledge on early signs of retinal vascular AD pathology and the potential implications of disease progression. Damaged BRB-mediated ocular metabolism and subsequent vascular leakage are pivotal pathogenic activities implicated in multiple retinal microvascular diseases such as diabetic retinopathy and age-mediated macular degeneration. Our data suggest that traditional retinal vascular disease-related BRB pathologies may also be vastly involved in the AD retina. The discovery of pathogenic Aβ deposits and early pericyte loss in retinal blood vessels of MCI and AD could shed light onto the pathophysiological mechanisms of vascular disruption, increased BRB permeability, insufficient blood supply, disrupted immune responses, and neuronal degeneration. In light of the recent advances in live imaging of retinal blood microvessels (OCT angiography), pericyte imaging using adaptive optics, and retinal amyloid imaging, these results lead to noninvasive retinal vascular amyloid and pericyte imaging technologies as described by various embodiments of the present invention to facilitate early screening and monitoring of AD.

In the present study we provide the first evidence for age-dependent retinal capillary degeneration that strongly associated with PDGFRβ deficiency and co-occurred with Aβ deposits in retinal blood vessels of the double-transgenic APP$_{SWE}$/PS1$_{ΔE9}$ mouse model. Retinal vascular changes in murine AD models were apparent at younger ages of 4 and 8 months and tightly correlated with severity of retinal pericyte biomarker (PDGFRβ) deficiency, suggesting pericyte loss occurs early in the retina of amyloidosis-derived AD models. The prominent accumulation of vascular Aβ in the retina of this AD-model mice agrees with findings in a different mouse model of AD (Tg2576) and with our evidence of vascular amyloidosis in postmortem retinas of MCI and AD patients. Further assessment of tight junction-associated proteins from neural retinal lysates showed alterations in claudin-1, ZO-1, and inflammatory-related NF-κB p65 phosphorylation, which all point to an impaired BRB in Alzheimer's-like retina. Finally, peripheral injection of molecules of increased sizes, fluorescein (~0.3 kD), Texas Red-dextran (3 kD) and FITC-dextran (2000 kD), revealed in vivo and ex vivo microvascular leakage in ADtg mouse retina. Taken together, our results broaden the current understanding of retinal microvascular degeneration and BRB integrity in AD murine models, providing new potential targets for AD therapy and encouraging the use of noninvasive retinal vascular imaging for AD diagnosis.

In the Alzheimer's brain, endothelial cell death, tight junction damage, and pericyte and vascular smooth muscle cell (vSMC) degeneration were determined to lead to the disruption of neurovascular units (NVUs) and breakdown of the BBB. Our recent study investigated these pathologies in the retina, revealing early and substantial pericyte apoptotic cell death and PDGFRβ deficiency in postmortem retinas obtained from MCI and AD patients. Our results here demonstrated capillary degeneration along with PDGFRβ downregulation, overall indicating a microvascular damage in the AD retina. The findings of our current study support the coexistence of neuronal and vascular damage in the AD retina. Another result to note here is the significant correlation between PDGFRβ and degenerated capillaries. In fact, pericyte loss and the decreased ratio to retinal endothelial cells (1:4) is believed to foretell retinal capillary degeneration in diabetic retinopathy (DR). DR is a typical retinal vascular degenerative disease where early pathological signatures involving retinal pericyte loss and capillary degeneration are thought to lead to microaneurysm, progressive microvascular leakage, abnormal growth of blood vessels, neurodegeneration, and eventually vision loss. However, an increasing number of studies have provided evidence to support an earlier neuronal dysfunction in the DR retina, potentially indicative of ganglion cell function loss, which predicted subsequent local microvasculopathy and macular edema. According to these and other studies, it is suggested that DR primarily affects retinal neuronal function and neurodegeneration, which in turn induce vascular complications. Similarly, our results revealing early retinal microvasculopathy and tight-junction molecular changes in AD may indicate a retina-specific neurovascular consequence of age-dependent disturbances between interactions of multiple cell types, such as neuronal, vascular, and perivascular cells. Although the specific mediators of such crosstalk between vascular abnormalities and neurodegeneration have not yet been identified in the AD retina. In any case, our results show that retinal microvascular degenerative pathologies are extensively implicated in the AD retina. Along with previous data showing neuronal function and neurodegeneration in ADtg mouse retina, this study contributes to the current understanding of Alzheimer's-related retinal NVU manifestation. Future studies should aim to investigate the potential impact of neurodegeneration on vasculopathy and further identify specific mediators linking vascular abnormalities and neurodegeneration in the AD retina.

Although retinal Aβ deposition in the APP$_{SWE}$/PS1$_{ΔE9}$ (ADtg) mouse model has been extensively described by us and others, the only clear demonstration of vascular Aβ accumulation in the murine model so far was based on the Tg2576 mice model in 2009. In the same year, Dutescu et al. (Dutescu R M, Li Q X, Crowston J, Masters C L, Baird P N, Culvenor J G (2009) Amyloid precursor protein processing and retinal pathology in mouse models of Alzheimer's disease. Graefes Arch Clin Exp Ophthalmol 247:1213-1221. doi:10.1007/s00417-009-1060-3) published the first report of amyloid precursor protein overexpression in the ganglion cell layers and inner nuclear layers in retinas of APP$_{SWE}$/PS1$_{ΔE9}$ mice. Using a curcumin-based method and confirming ex vivo with various epitope-specific anti-Aβ antibodies, our group was the first to image Aβ plaques in the retina of the same model in vivo, which was recently corroborated by Sidiqi et al. (Sidiqi A, Wahl D, Lee S, Ma D, To E, Cui J, To E, Beg M F, Sarunic M, Matsubara J A (2020) In vivo Retinal Fluorescence Imaging With Curcumin in an Alzheimer Mouse Model. Front Neurosci 14:713. doi: 10.3389/fnins.2020.00713). In the current study, by using a modified retinal microvascular isolation technique and immunofluorescence staining also in retinal cross sections, we have now provided the first illustration and quantification of retinal vascular Aβ accumulation in the double-transgenic APP$_{SWE}$/PS1$_{ΔE9}$ mouse model. The patterns of retinal vascular Aβ deposits in this study—in blood vessel walls, inside vascular and perivascular cells and attached to endothelial cells from the lumen side—appears similar to the CAA patterns reported in AD brains. Interestingly, no significant correlation was found here between retinal capillary degeneration and vascular Aβ burden. It is possible that the extent of retinal capillary degeneration may not be directly connected to levels of vascular Aβ but rather is affected by loss of pericytes and neurons, PDGFRβ deficiency, toxicity of abluminal retinal Aβ deposits, detrimental inflammatory reaction, or other indirect consequences of the disease. Yet, since cerebral and retinal Aβ plaques were reported to accumulate in the $APP_{SWE}/PS1_{\Delta E9}$ transgenic mouse before 6-7 months of age, retinal vascular degeneration may be driven by this early Aβ pathology. It is important to note that our correlation analysis was limited by a smaller sample size; future studies should explore these correlations in a larger cohort as well as determine how early vascular degeneration is initiated in the AD retina.

Endothelial cell junctions are indispensable parts of the BBB and inner BRB (iBRB) in maintaining cerebral and retinal homeostasis. Particularly, CNS tissues possess an enriched expression of tight junctions due to the need for maintenance of the blood barriers. The claudins form the backbone of tight junction stands and are pivotal in their transmembrane section, while the zonula occludens are located in the cytoplasm and connect the transmembrane parts of tight junctions to the cytoskeletons. Previously, significant downregulation of ZO-1, claudin-5, and occludin were described in both postmortem human cerebral capillaries with CAA and in 5×FAD transgenic mice. Here, we found decreased levels of claudin-1 in ADtg mice at 4 and 8 months of age but increased levels of ZO-1 at 12 months of age compared to control mice. Our results revealed dysregulation of endothelial tight junctions in the iBRB of ADtg mice. Specifically, downregulation of claudin-1 can indicate damage to the transmembrane part of the retinal endothelial tight junction in mice as young as 8 months old. However, increased levels of ZO-1 in 12-month-old ADtg mice possibly represent a compensatory mechanism in the endothelial cytoplasm in response to tight junction alteration. Importantly, significant correlations were found between retinal claudin-1 and both retinal PDGFRβ and capillary degeneration. These results imply that claudin-1 may be the best biomarker for BRB breakdown in the AD retina. To date, this is the first evaluation of tight junction molecules in the double-transgenic $APP_{SWE}/PS1_{\Delta E9}$ mouse model.

The NF-κB protein complex plays a pivotal role in regulating host immune and inflammatory responses by regulating transcription of cytokines and other immune mediators. Of the five subunits in this complex, p65 is the best characterized subunit and is crucial in activating cytokine production. Phosphorylation of NF-κB p65 is a prerequisite for its translocation into the nucleus and binding to target genes. In the current study, we uncovered an increase in phosphorylation of NF-κB p65 in retinas from 12-month-old ADtg mice compared to healthy WT controls. This may indicate an upregulated inflammatory response in the diseased retina. It is important to note that an augmented NF-κB response is implicated in retinal degeneration, retinal inflammation, as well as in the AD brain. Here, our results provide the first evidence of upregulated NF-κB activity in the retina of the double-transgenic $APP_{SWE}/PS1_{\Delta E9}$ mouse model. Importantly, a previous study utilizing bovine retinal endothelial cells and rat retinas found that the tumor necrosis factor-α-activated NF-κB pathway led to downregulation of tight junction molecules and increased retinal endothelial permeability (Aveleira C A, Lin C M, Abcouwer S F, Ambrosio A F, Antonetti D A (2010) TNF-alpha signals through PKCzeta/NF-kappaB to alter the tight junction complex and increase retinal endothelial cell permeability. Diabetes 59:2872-2882. doi:10.2337/db09-1606). Thus, our results of upregulated retinal NF-κB phosphorylation may underlie the molecular mechanisms involved in increased retinal microvascular permeability and iBRB breakdown. We also observed a near significant correlation (P=0.0650, Pearson's r=−0.55) between increased NF-κB phosphorylation and retinal vascular PDGFR deficiency, suggesting a possible relationship between NF-κB activity and pericyte loss in the AD retina.

In the present study, we revealed substantial live fluorescein leakage in the 12-month-old ADtg mice, but not in any of the 8-month or 16-month-old ADtg mice or control animals. We postulate that ADtg mice may present retinal microvascular damage and leakage, specifically related to fluorescein's molecular structure and size, around 12 months of age. Further, these disruptions may transform into other type of BRB abnormality when animals become older.

Importantly, our examination of flat-mount retinas 30 minutes following intravenous injections of FITC-dextran (2000 kD) and Texas Red-dextran (3 kD) demonstrated dramatic increases of permeability signals in retinal microvascular walls in ADtg mice compared to WT controls at 6-7 months of age, both for the high molecular weight and the low molecular weight compounds. In comparison, our previous study showed that Texas Red-dextran, but not FITC-dextran, was upregulated in the cerebral vasculature of the same double-transgenic ADtg mice compared to WT controls. Therefore, our data here indicate that the retina in this model may be more susceptible to AD-induced microvascular leakage than the brain.

The $APP_{SWE}/PS1_{\Delta E9}$ transgenic mice are reported to develop cerebral Aβ deposits by the age of 5-6 months and CAA at 6 months, with abundant plaques in the hippocampus and cortex by 9 months, which continue to build up with age. This mouse model has been well-characterized for behavioral deficits across various cognitive domains, although the time of onset and degree of impairment depended on the specific behavioral tests applied. Typically, spatial memory and learning performance as measured by Morris water maze or Barnes maze is considered normal at seven months of age and comparable to the non-transgenic mice. The hippocampal-based memory and learning functions are substantially impaired by 12 months. Contextual memory, however, may be impaired as early as 6 months of age, as shown by freezing behavior in fear-conditioning tests. Our current data reveals early changes in the ADtg mouse retina between 4 to 8 months of age, including levels of ZO-1 expression, increased capillary degeneration, PDGFRβ deficiency, as well as vascular amyloidosis and leakage. These findings suggest that retinal vascular damage in ADtg mice may precede cognitive deficits. Importantly, a recent investigation in the cerebral cortex of this mice model demonstrated early pathological changes to capillaries at 4 to 5 months of age, prior to the appearance of CAA and cognitive impairment. Here, the lack of cognitive data or assessment of retinal vascular Aβ and vascular PDGFRβ in mice younger than 4 months limits our ability to determine how early vascular pathology occurs in the retina and its relationship to cognitive deficits. Future studies should explore if any of the biomarkers tested in this study manifest before cerebral pathology and cognitive impairment in this mouse model.

In summary, our study provides a quantitative evaluation of retinal microvascular and iBRB integrity in the double-transgenic APP$_{SWE}$/PS1$_{ΔE9}$ mouse model. We identified early and progressive degeneration of retinal capillaries, PDGFRβ loss, retinal microvascular Aβ accumulation, disrupted tight junctions, induced NF-κB inflammatory response, and retinal microvascular leakage. These results have extended our understanding of microvascular damage in the AD retina and have provided multiple new candidate retinal biomarkers. Together with the recent developments of optical coherence tomography angiography (OCTA), retinal amyloid imaging, and retinal hyperspectral imaging in AD models, this study introduces novel retinal vascular imaging biomarkers that could be detected via a combined noninvasive retinal imaging approach for AD screening and disease monitoring.

Various embodiments are based, at least in part, on the findings described herein.

Various embodiments of the present invention provide for a method of detecting pericytes, PDGFR-β, low-density lipoprotein (LDL) receptor-related protein-1 (LRP-1), or combinations thereof in a subject in need thereof, comprising obtaining a retinal image of the subject; and detecting a decrease in the amount of pericytes or platelet-derived growth factor receptor-β (PDGFR-β) present in the retinal of the subject, wherein the decrease is compared to a control retinal image or compared to the subject's previous retinal image.

In various embodiments, the subject exhibits one or more symptoms of cognitive impairment. In various embodiments, the subject in need thereof is a subject having or suspected of having mild cognitive impairment (MCI). In various embodiments, the subject in need thereof is a subject having or suspected of having Alzheimer's disease.

In various embodiments, detecting the decrease in the amount of pericytes, PDGFR-β, LRP-1 or combinations thereof present in the retinal of the subject comprising using a live retina imaging technique. In various embodiments, detecting the decrease in the amount of pericytes present in the retina of the subject comprises using an advanced ophthalmic imaging technique. In various embodiments, the advanced ophthalmic imaging technique is adaptive optics.

In various embodiments, detecting the decrease in the amount of pericytes, PDGFR-β, LRP-1 or combinations thereof present in the retina of the subject comprises using adaptive optics, optical coherence tomography angiography, color fundus photography, fluorescein angiography, indocyanine green angiography, scanning laser ophthalmoscopy, optical coherence tomography, confocal microscopy, retinal hyperspectral imaging or OCTA.

In various embodiments, detecting the decrease in the amount of PDGFR-β present in the retina of the subject comprises administering a contrast agent to the subject, and using optical imaging to detect the amount of PDGFR-β present in the retina. In various embodiments, the contrast agent is prednisolone acetate (PA), triamcinolone acetonide (TA), lipid-based artificial tears (LBAT), sodium fluorescein, fluorescein, or indocyanine.

In various embodiments, detecting the decrease in the amount of PDGFR-β present in the retina of the subject comprises administering a labelled anti-PDGFR-β antibody and using optical imaging to detect the amount of PDGFR-β present in the retina.

In various embodiments, detecting the decrease in the amount of PDGFR-β present in the retina of the subject comprises administering a labelled anti-PDGFR-β aptimer and using optical imaging to detect the amount of PDGFR-β present in the retina.

In various embodiments, detecting the decrease in the amount of LRP-1 present in the retina of the subject comprises administering a labelled anti-LRP-1 antibody and using optical imaging to detect the amount of anti-LRP-1 present in the retina.

In various embodiments, the method further comprises detecting an increase in vascular Aβ deposition in the retina of the subject.

In various embodiments, detecting an increase in vascular Aβ deposition in the retina of the subject comprises administering an anti-Aβ compound and using optical imaging to detect the amount of Aβ deposition in the retina. In various embodiments, the anti-Aβ compound is anti-Aβ antibody or curcumin. Methods of detecting Aβ deposition using curcumin are described in International Application No. PCT/US2009/057569 (Publication No. WO/2010/033861), entitled Optical Method for the Detection of Alzheimer's Disease, the entirety of which is incorporated herein by reference as though fully set forth.

In various embodiments, the method further comprising predicting cognitive decline in the subject; for example, based on the decrease in pericytes or PDGFR-0.

In various embodiments, the method further comprises monitoring the subject by repeating the method.

Various embodiments of the present invention provide for a method of detecting an alteration in blood-retinal barrier (BRB) cell tight junction in a subject in need thereof, comprising: assaying a biological sample from the subject and detecting a decrease in claudin-1, in the biological sample wherein the decrease is compared to a control claudin-1 level or compared to the subject's previous claudin-1 level; or assaying a biological sample from the subject and detecting an increase in NF-κB phosphorylation levels, wherein the increase is compared to a control NF-κB phosphorylation level or compared to the subject's previous NF-κB phosphorylation level; or detecting an increase in retinal vascular leakage level compared to a control level, or compared to the subject's previous level.

In various embodiments, the subject in need thereof exhibits one or more symptoms of cognitive impairment. In various embodiments, the subject in need thereof is a subject having or suspected of having mild cognitive impairment (MCI). In various embodiments, the subject in need thereof is a subject having or suspected of having Alzheimer's disease.

In various embodiments, the NF-κB phosphorylation is NF-κB p65 phosphorylation.

In various embodiments, detecting the increase in retinal vascular leakage level comprises: administering a fluorophore to the subject; imaging a retina; and detecting the level of fluorophore leakage.

In various embodiments, the fluorophore is fluorescein, FITC-dextran (2000 kD), Texas Red-dextran (3 kD), or combinations thereof. In various embodiments, the flurophore is any one of the flurophores as described herein.

In various embodiments, a decrease in claudin-1 indicates an alteration in blood-retinal barrier (BRB) cell tight junction. In various embodiments, an increase in NF-κB phosphorylation levels indicates an alteration in blood-retinal barrier (BRB) cell tight junction. In various embodiments, an increase in retinal vascular leakage level indicates an alteration in blood-retinal barrier (BRB) cell tight junction. An alteration in blood-retinal barrier (BRB) cell tight junction indicates conative impairment and/or cognitive decline in the subject.

Various embodiments of the present invention provide for a method of monitoring cognitive status of a subject in need thereof, comprising: obtaining an initial retinal image of the subject; detecting an amount of pericytes, platelet-derived growth factor receptor-β (PDGFR-β), LDL receptor-related protein-1 (LRP-1), or combinations thereof present in the retina of the subject in the initial retinal image; obtaining a subsequent retinal image of the subject; detecting an amount of pericytes, PDGFR-β, LDL receptor-related protein-1 (LRP-1), or combinations thereof present in the retina of the subject in the subsequent retinal image; comparing the amount of pericytes, PDGFR-β, LDL receptor-related protein-1 (LRP-1), or combinations thereof present in the first retinal image and the second retinal image; and detecting whether there is a change in the amount of pericytes, PDGFR-f, LRP-1, or combinations thereof present in the retina.

In various embodiments, the method further comprises administering a MCI or Alzheimer's disease therapy when a decrease in the amount of pericytes or PDGFR-β present in the retina is detected. Therapies to treat MCI or Alzheimer's disease include but are not limited to cholinesterase inhibitors such as donepezil (Aricept), galantamine (Razadyne) and rivastigmine (Exelon), and memantine.

In various embodiments, the subject exhibits one or more symptoms of cognitive impairment. In various embodiments, the subject in need thereof is a subject having or suspected of having mild cognitive impairment (MCI). In various embodiments, the subject in need thereof is a subject having or suspected of having Alzheimer's disease.

In various embodiments, detecting the amount of pericytes, PDGFR-β, LRP-1 or combinations thereof present in the retinal of the subject comprises using alive retina imaging technique. In various embodiments, the detecting the decrease in the amount of pericytes present in the retina of the subject comprises using an advanced ophthalmic imaging technique. In various embodiments, the advanced ophthalmic imaging technique is adaptive optics.

In various embodiments, detecting the amount of pericytes, PDGFR-β, LRP-1, or combinations thereof present in the retinal of the subject comprises using adaptive optics, optical coherence tomography angiography, color fundus photography, fluorescein fundus imaging, fluorescein angiography, indocyanine green angiography, scanning laser ophthalmoscopy, optical coherence tomography, confocal microscopy, retinal hyperspectral imaging or optical coherence tomography angiography (OCTA).

In various embodiments, the detecting the amount of PDGFR-β present in the retina of the subject comprises administering a contrast agent to the subject, and using optical imaging to the detect the amount of PDGFR-β present in the retina. In various embodiments, the contrast agent is prednisolone acetate (PA), triamcinolone acetonide (TA), lipid-based artificial tears (LBAT), sodium fluorescein, fluorescein, or indocyanine.

In various embodiments, detecting the amount of PDGFR-β present in the retina of the subject comprises administering a labelled anti-PDGFR-β antibody and using optical imaging to detect the amount of PDGFR-β present in the retina.

In various embodiments, detecting the amount of PDGFR-β present in the retina of the subject comprises administering a labelled anti-PDGFR-β aptimer and using optical imaging to detect the amount of PDGFR-β present in the retina.

In various embodiments, detecting the amount of LRP-1 present in the retina of the subject comprises administering a labelled anti-LRP-1 antibody and using optical imaging to detect the amount of anti-LRP-1 present in the retina.

In various embodiments, the method further comprises detecting an increase in vascular Aβ deposition in the retina of the subject.

In various embodiments, detecting an increase in vascular Aβ deposition in the retina of the subject comprises administering an anti-Aβ compound and using optical imaging to detect the amount of Aβ deposition in the retina. In various embodiments, the anti-Aβ compound is anti-Aβ antibody or curcumin. Methods of detecting Aβ deposition using curcumin are described in International Application No. PCT/US2009/057569, entitled Optical Method for the Detection of Alzheimer's Disease, the entirety of which is incorporated herein by reference as though fully set forth.

In various embodiments, the method further comprises detecting an alteration in blood-retinal barrier (BRB) cell tight junction in a subject in need thereof, comprising: assaying a biological sample from the subject and detecting a decrease in claudin-1, in the biological sample wherein the decrease is compared to a control claudin-1 level or compared to the subject's previous claudin-1 level; or assaying a biological sample from the subject and detecting an increase in NF-κB phosphorylation levels, wherein the increase is compared to a control NF-κB phosphorylation level or compared to the subject's previous NF-κB phosphorylation level; or detecting an increase in retinal vascular leakage level compared to a control level, or compared to the subject's previous level.

In various embodiments, the NF-κB phosphorylation is NF-κB p65 phosphorylation.

In various embodiments, detecting the increase retinal vascular leakage level comprises: administering a fluorophore to the subject; imaging a retina; and detecting the level of fluorophore leakage.

In various embodiments, the fluorophore is fluorescein, FITC-dextran (2000 kD), Texas Red-dextran (3 kD), or combinations thereof. In various embodiments, the flurophore is any one of the flurophores as described herein.

In various embodiments, a decrease in claudin-1 indicates an alteration in blood-retinal barrier (BRB) cell tight junction. In various embodiments, an increase in NF-κB phosphorylation levels indicates an alteration in blood-retinal barrier (BRB) cell tight junction. In various embodiments, an increase in retinal vascular leakage level indicates an alteration in blood-retinal barrier (BRB) cell tight junction. An alteration in blood-retinal barrier (BRB) cell tight junction indicates conative impairment and/or cognitive decline in the subject.

In various embodiments, the method further comprises predicting cognitive decline in the subject.

Various embodiments of the present invention provide for a method of diagnosing cognitive impairment in a subject, comprising obtaining a retinal image of the subject; detecting a decrease in the amount of pericytes, platelet-derived growth factor receptor-β (PDGFR-β), LDL receptor-related protein-1 (LRP-1), or combinations thereof present in the retinal of the subject, wherein the decrease is compared to a control retinal image or compared to the subject's previous retinal image; and diagnosing cognitive impairment or Alzheimer's disease based on the detection of the decrease in the amount of pericytes, platelet-derived growth factor receptor-β (PDGFR-β), LDL receptor-related protein-1 (LRP-1), or combinations thereof present in the retina of the subject.

In various embodiments, the method further comprises administering a mild cognitive impairment (MCI) or Alzheimer's disease therapy when cognitive impairment is diagnosed in the subject. Therapies to treat MCI or Alzheimer's disease include but are not limited to cholinesterase inhibitors such as donepezil (Aricept), galantamine (Razadyne) and rivastigmine (Exelon), and memantine.

In various embodiments, the subject exhibits one or more symptoms of cognitive impairment. In various embodiments, the subject in need thereof is a subject having or suspected of having mild cognitive impairment (MCI). In various embodiments, the subject in need thereof is a subject having or suspected of having Alzheimer's disease. In various embodiments, the cognitive impairment is Alzheimer's disease.

In various embodiments, detecting the decrease in the amount of pericytes or PDGFR-β present in the retinal of the subject comprises using a live retina imaging technique. In various embodiments, the detecting the decrease in the amount of pericytes present in the retina of the subject comprises using an advanced ophthalmic imaging technique. In various embodiments, the advanced ophthalmic imaging technique is adaptive optics.

In various embodiments, detecting the decrease in the amount of pericytes, PDGFR-β, LRP-1 or combinations thereof present in the retina of the subject comprises using adaptive optics, optical coherence tomography angiography, color fundus photography, fluorescein fundus imaging, fluorescein angiography, indocyanine green angiography, scanning laser ophthalmoscopy, optical coherence tomography, confocal microscopy, retinal hyperspectral imaging or optical coherence tomography angiography (OCTA).

In various embodiments, the detecting the decrease in the amount of PDGFR-β present in the retina of the subject comprises administering a contrast agent to the subject, and using optical imaging to detect the amount of PDGFR-β present in the retina. In various embodiments, the contrast agent is prednisolone acetate (PA), triamcinolone acetonide (TA), lipid-based artificial tears (LBAT), sodium fluorescein, fluorescein, or indocyanine.

In various embodiments, detecting the decrease in the amount of PDGFR-β present in the retina of the subject comprises administering a labelled anti-PDGFR-β antibody and using optical imaging to detect the amount of PDGFR-β present in the retina.

In various embodiments, detecting the decrease in the amount of PDGFR-β present in the retina of the subject comprises administering a labelled anti-PDGFR-β aptimer and using optical imaging to detect the amount of PDGFR-β present in the retina.

In various embodiments, detecting the decrease in the amount of LRP-1 present in the retina of the subject comprises administering a labelled anti-LRP-1 antibody and using optical imaging to detect the amount of anti-LRP-1 present in the retina.

In various embodiments, the method further comprises detecting an increase in vascular Aβ deposition in the retina of the subject.

In various embodiments, detecting an increase in vascular Aβ deposition in the retina of the subject comprises administering an anti-Aβ compound and using optical imaging to detect the amount of Aβ deposition in the retina. In various embodiments, the anti-Aβ compound is anti-Aβ antibody or curcumin. Methods of detecting Aβ deposition using curcumin are described in International Application No. PCT/US2009/057569, entitled Optical Method for the Detection of Alzheimer's Disease, the entirety of which is incorporated herein by reference as though fully set forth.

In various embodiments, the method further comprises detecting an alteration in blood-retinal barrier (BRB) cell tight junction in a subject in need thereof, comprising: assaying a biological sample from the subject and detecting a decrease in claudin-1, in the biological sample wherein the decrease is compared to a control claudin-1 level or compared to the subject's previous claudin-1 level; or assaying a biological sample from the subject and detecting an increase in NF-κB phosphorylation levels, wherein the increase is compared to a control NF-κB phosphorylation level or compared to the subject's previous NF-κB phosphorylation level; or detecting an increase in retinal vascular leakage level compared to a control level, or compared to the subject's previous level.

In various embodiments, the NF-κB phosphorylation is NF-κB p65 phosphorylation.

In various embodiments, detecting the increase retinal vascular leakage level comprises: administering a fluorophore to the subject; imaging a retina; and detecting the level of fluorophore leakage.

In various embodiments, the fluorophore is fluorescein, FITC-dextran (2000 kD), Texas Red-dextran (3 kD), or combinations thereof. In various embodiments, the flurophore is any one of the flurophores as described herein.

In various embodiments, a decrease in claudin-1 indicates an alteration in blood-retinal barrier (BRB) cell tight junction. In various embodiments, an increase in NF-κB phosphorylation levels indicates an alteration in blood-retinal barrier (BRB) cell tight junction. In various embodiments, an increase in retinal vascular leakage level indicates an alteration in blood-retinal barrier (BRB) cell tight junction. An alteration in blood-retinal barrier (BRB) cell tight junction indicates conative impairment and/or cognitive decline in the subject.

In various embodiments, the method further comprises predicting cognitive decline in the subject. In various embodiments, the method further comprises monitoring the subject by repeating the method.

Various embodiments of the present invention provide for a method for treating a cognitive impairment or Alzheimer's disease in a subject, comprising: obtaining results of an analysis of a level of pericytes, PDGFR-β, and/or LRP-1 present in a retina of the subject; and administering a cholinesterase inhibitor to the subject when the level of pericytes, PDGFR-β, and/or LRP-1 is below a reference level or when a decrease in the level of pericytes, PDGFR-β, and/or LRP-1 is detected according to the obtained results.

In various embodiments, the cholinesterase inhibitor comprises at least one of donepezil (Aricept), galantamine (Razadyne), rivastigmine (Exelon), and/or memantine when the level of pericytes and/or PDGFR-β is below a reference level or when a decrease in the level of pericytes and/or PDGFR-β is detected according to the obtained results.

In various embodiments, the analysis of the level of pericytes and/or PDGFR-β is performed by detecting the decrease in the level of pericytes, PDGFR-β, or combinations thereof present in the retina of the subject, using a live retina imaging technique.

In various embodiments, the analysis of the level of pericytes is performed by detecting the decrease in the level of pericytes present in the retina of the subject, using an advanced ophthalmic imaging technique. In various embodiments, the advanced ophthalmic imaging technique is adaptive optics.

In various embodiments, the analysis of the level of pericytes and/or PDGFR-β is performed by detecting the decrease in the level of pericytes, PDGFR-β, or combinations thereof present in the retina of the subject, using adaptive optics, optical coherence tomography angiography, color fundus photography, fluorescein fundus imaging, fluorescein angiography, indocyanine green angiography, scanning laser ophthalmoscopy, optical coherence tomography, confocal microscopy, retinal hyperspectral imaging or optical coherence tomography angiography (OCTA).

In various embodiments, the analysis of the level of PDGFR-β is performed by detecting the decrease in the level of PDGFR-β present in the retina of the subject, the detecting the decreased level of PDGFR-β comprising administering a contrast agent to the subject and using optical imaging to detect the level of PDGFR-f present in the retina. In various embodiments, the contrast agent is prednisolone acetate (PA), triamcinolone acetonide (TA), lipid-based artificial tears (LBAT), sodium fluorescein, fluorescein, or indocyanine.

In various embodiments, the analysis of the level of PDGFR-β is performed by detecting the decrease in the level of PDGFR-β present in the retina of the subject, the detecting the decrease in the level of PDGFR-β comprising administering a labelled anti-PDGFR-β antibody and using optical imaging to detect the level of PDGFR-β present in the retina.

In various embodiments, the analysis of the level of LRP-1 is performed by detecting the decrease in the level of LRP-1 present in the retina of the subject, the detecting the decrease in the level of LRP-1 comprising administering a labelled anti-LRP-1 antibody and using optical imaging to detect the amount of anti-LRP-1 present in the retina.

Various embodiments of the present invention provide for a method for treating a cognitive impairment or Alzheimer's disease in a subject, comprising: administering a cholinesterase inhibitor to the subject who has been determined to have a level of pericytes, PDGFR-β, and/or LRP-1 present in a retina of the subject below a reference level or have a decreased level of pericytes, PDGFR-β, and/or LRP-1 present in the retina of the subject.

In various embodiments, the cholinesterase inhibitor comprises at least one of donepezil (Aricept), galantamine (Razadyne), rivastigmine (Exelon), and/or memantine when the level of pericytes and/or PDGFR-β is below a reference level or when a decrease in the level of pericytes and/or PDGFR-β is detected according to the obtained results.

In various embodiments, the level of pericytes and/or PDGFR-β was determined by detecting the decrease in the level of pericytes, PDGFR-β, or combinations thereof present in the retina of the subject, using a live retina imaging technique.

In various embodiments, the level of pericytes was determined by detecting the decrease in the level of pericytes present in the retina of the subject, using an advanced ophthalmic imaging technique. In various embodiments, the advanced ophthalmic imaging technique is adaptive optics.

In various embodiments, the level of pericytes and/or PDGFR-β was determined by detecting the decrease in the level of pericytes, PDGFR-β, or combinations thereof present in the retina of the subject, using adaptive optics, optical coherence tomography angiography, color fundus photography, fluorescein fundus imaging, fluorescein angiography, indocyanine green angiography, scanning laser ophthalmoscopy, optical coherence tomography, confocal microscopy, retinal hyperspectral imaging or optical coherence tomography angiography (OCTA).

In various embodiments, the level of PDGFR-β was determined by detecting the decrease in the level of PDGFR-β present in the retina of the subject, the detecting the decreased level of PDGFR-β comprising administering a contrast agent to the subject and using optical imaging to the detect the level of PDGFR-β present in the retina. In various embodiments, the contrast agent is prednisolone acetate (PA), triamcinolone acetonide (TA), lipid-based artificial tears (LBAT), sodium fluorescein, fluorescein, or indocyanine.

In various embodiments, the level of PDGFR-β was determined by detecting the decrease in the level of PDGFR-β present in the retina of the subject, the detecting the decrease in the level of PDGFR-β comprising administering a labelled anti-PDGFR-β antibody and using optical imaging to detect the level of PDGFR-β present in the retina.

In various embodiments, the level of LRP-1 was determined by detecting the decrease in the level of LRP-1 present in the retina of the subject, the detecting the decrease in the level of LRP-1 comprising administering a labelled anti-LRP-1 antibody and using optical imaging to detect the amount of anti-LRP-1 present in the retina.

Various embodiments of the present invention provide for a method of treating mild cognitive impairment (MCI), comprising administering an MCI treatment to a subject identified as having a decrease in the amount of pericytes, platelet-derived growth factor receptor-β (PDGFR-β), LDL receptor-related protein-1 (LRP-1), or combinations thereof present in a retina of the subject, wherein the decrease is detected by comparing the obtained retinal image to a control retinal image or the subject's previous retinal image In various embodiments, the MCI treatment comprises a cholinesterase inhibitor.

In various embodiments, the cholinesterase inhibitor comprises at least one of donepezil (Aricept), galantamine (Razadyne), rivastigmine (Exelon), and/or memantine when the level of pericytes and/or PDGFR-β is below a reference level or when a decrease in the level of pericytes and/or PDGFR-β is detected according to the obtained results.

In various embodiments, the decrease in the amount of pericytes, PDGFR-β, or combinations thereof present in the retina of the subject is detected using a live retina imaging technique.

In various embodiments, the decrease in the amount of pericytes present in the retina of the subject is detected using an advanced ophthalmic imaging technique. In various embodiments, the advanced ophthalmic imaging technique is adaptive optics.

In various embodiments, the decrease in the amount of pericytes, PDGFR-β, or combinations thereof present in the retina of the subject is detected using adaptive optics, optical coherence tomography angiography, color fundus photography, fluorescein fundus imaging, fluorescein angiography, indocyanine green angiography, scanning laser ophthalmoscopy, optical coherence tomography, confocal microscopy, retinal hyperspectral imaging or optical coherence tomography angiography (OCTA).

In various embodiments, the decrease in the amount of PDGFR-β present in the retina of the subject is detected by administering a contrast agent to the subject and using optical imaging to detect the amount of PDGFR-β present in the retina. In various embodiments, the contrast agent is prednisolone acetate (PA), triamcinolone acetonide (TA), lipid-based artificial tears (LBAT), sodium fluorescein, fluorescein, or indocyanine.

In various embodiments, the decrease in the amount of PDGFR-β present in the retina of the subject is detected by administering a labelled anti-PDGFR-β antibody and using optical imaging to detect the level of PDGFR-β present in the retina.

In various embodiments, the decrease in the amount of LRP-1 present in the retina of the subject is detected by administering a labelled anti-LRP-1 antibody and using optical imaging to detect the amount of anti-LRP-1 present in the retina.

Various embodiments of the present invention provide for a method of treating Alzheimer's disease, comprising administering an Alzheimer's disease treatment to a subject identified as having a decrease in the amount of pericytes, platelet-derived growth factor receptor-β (PDGFR-β), LDL receptor-related protein-1 (LRP-1), or combinations thereof present in a retina of the subject, wherein the decrease is detected by comparing the obtained retinal image to a control retinal image or the subject's previous retinal image In various embodiments, the Alzheimer's disease treatment comprises a cholinesterase inhibitor.

In various embodiments, the cholinesterase inhibitor comprises at least one of donepezil (Aricept), galantamine (Razadyne), rivastigmine (Exelon), and/or memantine when the level of pericytes and/or PDGFR-β is below a reference level or when a decrease in the level of pericytes and/or PDGFR-β is detected according to the obtained results.

In various embodiments, the decrease in the amount of pericytes, PDGFR-β, or combinations thereof present in the retina of the subject is detected using a live retina imaging technique.

In various embodiments, the decrease in the amount of pericytes present in the retina of the subject is detected using an advanced ophthalmic imaging technique. In various embodiments, the advanced ophthalmic imaging technique is adaptive optics.

In various embodiments, the decrease in the amount of pericytes, PDGFR-β, or combinations thereof present in the retina of the subject is detected using adaptive optics, optical coherence tomography angiography, color fundus photography, fluorescein fundus imaging, fluorescein angiography, indocyanine green angiography, scanning laser ophthalmoscopy, optical coherence tomography, confocal microscopy, retinal hyperspectral imaging or optical coherence tomography angiography (OCTA).

In various embodiments, the decrease in the amount of PDGFR-β present in the retina of the subject is detected by administering a contrast agent to the subject and using optical imaging to detect the amount of PDGFR-β present in the retina. In various embodiments, the contrast agent is prednisolone acetate (PA), triamcinolone acetonide (TA), lipid-based artificial tears (LBAT), sodium fluorescein, fluorescein, or indocyanine.

In various embodiments, the decrease in the amount of PDGFR-β present in the retina of the subject is detected by administering a labelled anti-PDGFR-β antibody and using optical imaging to detect the level of PDGFR-β present in the retina.

In various embodiments, the decrease in the amount of LRP-1 present in the retina of the subject is detected by administering a labelled anti-LRP-1 antibody and using optical imaging to detect the amount of anti-LRP-1 present in the retina.

Administrations of the various compounds, agents and compositions described herein in accordance with various embodiments of the invention can be any administration pathway known in the art, including but not limited to intravenous, intraocular, intraretinal, subcutaneous, aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compounds, agents and compositions may be in the form of solutions or suspensions for infusion or for injection, or as lyophilized powders. Via the enteral route, the compounds, agents and compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compounds, agents and compositions may be in the form of solutions or suspensions for infusion or for injection. Via the topical route, the compounds, agents and compositions may be formulated for administration to the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

As described herein certain antibodies or compounds are labelled. As used herein, the term "label" refers to a composition capable of producing a detectable signal indicative of the presence of a target. Suitable labels, for example, for the anti-LRP-1 antibodies anti-PDGFR-β antibodies, and anti-Aβ compounds, include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means needed for the methods and devices described herein. For example, peptides can be labeled with a detectable tag which can be detected using an antibody specific to the label.

Exemplary fluorophores and fluorescent labeling reagents include, but are not limited to, fluorescein, Hydroxycoumarin, Succinimidyl ester, Aminocoumarin, Methoxycoumarin, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, TruRed (PerCP-Cy5.5 conjugate), FluorX, Fluoresceinisothyocyanate (FITC), FITC-dextran (2000 kD), BODIPY-FL, TRITC, X-Rhodamine (XRITC), Lissamine Rhodamine B, Texas Red, Texas Red-dextran (3 kD), Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5 or Cy7.

An example of an anti-PDGFR-β aptimer that can be used herein is 2' F-Pyrimidines (2'F-Py) RNA anti-PDGFRβ Gint4.T aptamer. (See e.g., Simona Camorani, et al. Targeted imaging and inhibition of triple-negative breast cancer metastases by a PDGFRβ aptamer. Theranostics. 2018; 8(18): 5178-5199.)

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Human Eye and Brain Donors.

Donor eyes were obtained from two sources: 1) Alzheimer's Disease Research Center (ADRC) Neuropathology Core at the Department of Pathology in the University of Southern California (USC, Los Angeles, CA; IRB protocol HS-042071) and 2) National Disease Research Interchange (NDRI, Philadelphia, PA; IRB exempt protocol EX-1055). Both USC-ADRC and NDRI maintain human tissue collection protocols approved by a managerial committee and subject to National Institutes of Health oversight. For a subset of patients and controls we also obtained brain specimens from USC-ADRC. The histological work at Cedars-Sinai Medical Center was performed under IRB protocols Pro00053412 and Pro00019393. Sixty-two post-mortem retinas were collected from 29 clinically- and neuropathologically-confirmed AD patients (age mean±SD: 81.38±13.79; range 40-98 years; 20 females and 9 males with different disease severities), 11 age- and gender-matched MCI patients (age mean±SD: 86.45±6.87; range 80-93 years; 5 females and 6 males with different disease severities), and 22 CN individuals (age mean±SD: 78.18±8.86; range 58-95 years; 13 females and 9 males showing neither clinical cognitive impairment/dementia nor brain pathology). The entire human cohort information is listed in Table 1. The groups had no significant differences in age, sex, or post-mortem interval (PMI) hours. All samples were deidentified and could not be traced back to tissue donors.

(CDR; 0=Normal; 0.5=Very Mild Dementia; 1=Mild Dementia; 2=Moderate Dementia; 3=Severe Dementia) and the Mini Mental State Examination (MMSE; normal cognition=24-30, mild dementia=20-23, moderate dementia=10-19, severe dementia≤9). In this study, the clinical diagnostic groups (AD, MCI, and CN) were determined by the source clinicians, based on a comprehensive battery of tests, including neurological examinations, neuropsychological evaluations, and the above-mentioned cognitive tests. For final diagnosis based on the neuropathological reports, the modified Consortium to Establish a Registry for Alzheimer's Disease was used as outlined in the National Institute on Aging (NIA)/Regan protocols with revision by the NIA and Alzheimer's Association. Aβ burden (diffuse, immature, or mature plaques), amyloid angiopathy, neuritic plaques, NFTs, neuropil threads, granulovacuolar degeneration, Lewy bodies, Hirano bodies, Pick bodies, balloon cells, neuronal loss, microvascular changes and gliosis pathology were assessed in multiple brain areas: hippocampus (CA1 & CA4), entorhinal cortex, frontal cortex, temporal lobe, parietal lobe, occipital lobe (primary visual cortex, area 17; visual association cortex, area 18), basal ganglia, brainstem (pons, midbrain), cerebellum and substantia nigra.

Amyloid plaques and tangles in the brain were evaluated using anti β-amyloid mAb clone 4G8, Thioflavin-S (ThioS), and Gallyas silver stain in formalin-fixed, paraffin-embedded tissues. Two neuropathologists provided scores based on independent observations of β-amyloid, NFT burden, and/or neuropil threads (0=none; 1=sparse 0-5; 3=moderate 6-20; 5=abundant/frequent 21-30 or above; N/A=not applicable), and an average of two readings was assigned to each individual. Final diagnosis included AD neuropathologic change (ADNC). Aβ plaque score was modified from Thal et al. (A0=no Aβ or amyloid plaques; A1=Thal phase 1 or 2; A2=Thal phase 3; A3=Thal phase 4 or 5) (Thal D R, Rub U, Orantes M, Braak H (2002) Phases of A beta-deposition in the human brain and its relevance for the development of

TABLE 1

Demographic data for all human eye donors

| (N = 62) | CN | MCI | AD | F | P |
|---|---|---|---|---|---|
| Subject size | 22 | 11 | 29 | — | — |
| Females (%), Males | 13F (59%), 9M | 5F (45%), 6M | 20F (69%), 9M | | |
| Age ± SD (Years) | 78.18 ± 8.86 | 86.45 ± 4.87 | 81.38 ± 13.79 | 2.075 | 0.1346 |
| Race (%) | 17C (77.3%) | 9C (81.8%) | 18C (62.1%) | — | — |
| | 1B (4.5%) | 1H (9.1%) | 1B (3.4%) | | |
| | 4N/A (18.2%) | 1B (9.1%) | 5A (17.2%) | | |
| | | | 3H (10.3%) | | |
| | | | 2N/A (6.9%) | | |
| PMI (Hours) | 7.1 ± 2.2 | 8.9 ± 5.2 | 7.4 ± 3.7 | 0.8010 | 0.4540 |

CN cognitively normal; MCI, mild cognitive impairment; AD, Alzheimer's disease; F female, M, male; SD, standard deviation; C, Caucasian; B, Black; H, Hispanic; A, Asian, N/A, not available; PMI, post-mortem interval; Values are presented as mean ± SD. F and P values were determined by one-way ANOVA with Sidak's multiple comparison test.

Clinical and Neuropathological Assessments.

The clinical and neuropathological reports provided by the USC ADRC Clinical Core included subjects' neurological examinations, neuropsychological and cognitive tests, family history, and medication list; psychometric test performed by a trained psychometrist under the supervision of a licensed clinical neuropsychologist, that followed standard-of-care cognitive screening evaluations of patients in their respective neurology clinics. NDRI reports provided the medical history of each subject. Most cognitive evaluations were performed annually, and, in most cases, less than one year prior to death. Cognitive testing scores from evaluations obtained closest to subjects' death were used for this analysis. Two global indicators of cognitive status were used for clinical assessment: the Clinical Dementia Rating AD. Neurology 58:1791-1800. doi:10.1212/wnl.58.12.1791). NFT stage was modified from Braak for silver-based histochemistry or p-tau IHC (B0=No NFTs; B1=Braak stage I or II; B2=Braak stage III or IV; B3=Braak stage V or VI). Neuritic plaque score was modified from CERAD (C0=no neuritic plaques; C1=CERAD score sparse; C2=CERAD score moderate; C3=CERAD score frequent). Neuronal loss, gliosis, granulovacuolar degeneration, Hirano bodies, Lewy bodies, Pick bodies and balloon cells were evaluated (0=absent; 1=present) in multiple brain areas using hematoxylin and eosin (H&E) staining. Amyloid angiopathy was graded as follows: Grade I=amyloid restricted to a rim around normal/atrophic SMCs of vessels; Grade 11=media replaced by amyloid and thicker than normal, but no evidence of blood leakage; Grade III=extensive amyloid deposition with focal vessel wall fragmentation and at least one focus of perivascular leakage; Grade IV=extensive amyloid deposition and fibrinoid necrosis, micro aneurysms, mural thrombi, lumen inflammation, and perivascular neuritis. For the correlation analyses against retinal parameters, we used the following CAA scoring system: no amyloid angiopathy was assigned '0'; grade I was assigned as '1', grade I-II as '1.5', grade II as '2', and grade II-III as '2.5'.

Collection and Processing of Eyes and Cortical Tissues.

Donor eyes were collected within 7 hours, on average, from time of death and were either preserved in Optisol-GS media (Bausch & Lomb, 50006-OPT) and stored at 4° C. for less than 24 hours, fresh frozen (snap; stored at −80° C.), or punctured once and fixed in 10% neutral buffered formalin (NBF) or 2.5% Paraformaldehyde (PFA) and stored at 4° C. Brain tissues (hippocampus; occipital lobe—primary visual cortex, area-17, and frontal cortex, area-9) from the same donors were snap frozen and stored at −80° C. Parts from the fresh-frozen brain tissues were fixed in 4% PFA for 16 hours following dehydration in 30% sucrose/PBS. Brain tissues were cryosectioned (30 μm thick) and placed in phosphate buffered saline 1× (PBS) with 0.01% sodium azide (Sigma-Aldrich) at 4° C. Irrespective of the human donor eye source, USC-ADRC or NDRI, the same tissue collection and processing methods were applied.

Preparation of Retinal Flatmounts and Strips.

Fresh-frozen eyes and eyes preserved in Optisol-GS were dissected with anterior chambers removed to create eyecups. Vitreous humor was thoroughly removed manually. Retinas were dissected out, detached from the choroid, and flatmounts were prepared. By identifying the macula, optic disc, and blood vessels, the geometrical regions of the four retinal quadrants were defined with regard to the left and the right eye. Flatmount strips (2-3 mm in width) were dissected along the retinal quadrant margins to create four strips: superior-temporal—ST, inferior-temporal—TI; inferior-nasal—IN, and superior-nasal—NS, and were fixed in 2.5% PFA for cross-sectioning. In a subset of human eye donors, a second set of strips was prepared (5 mm in width) and stored at −80° C. for protein analysis. Each strip was approximately 2-2.5 cm long from the optic disc to the ora serrata and included the central, mid, and far retinal areas. All the above stages were performed in cold PBS with 1× Protease Inhibitor cocktail set I (Calbiochem 539131). Eyes that were initially fixed in 10% NBF or 2.5% PFA were dissected to create eyecups, and the retinas were dissected free. Vitreous humor was thoroughly removed and flatmounts were prepared. As described above, a set of flatmount strips (ST, TI, IN, and NS) was dissected (2-3 mm in width), washed in PBS, and processed for retinal cross-sectioning.

Retinal Cross-Sections.

Flatmount strips were initially embedded in paraffin using standard techniques, then rotated 90° horizontally and embedded in paraffin. The retinal strips were sectioned (7-10 μm thick) and placed on microscope slides that were treated with 3-Aminopropyltriethoxysilane (APES, Sigma A3648). Before immunohistochemistry, the sections were deparaffinized with 100% xylene twice (for 10 min each), rehydrated with decreasing concentrations of ethanol (100% to 70%), and then washed with distilled water followed by PBS.

Retinal Vascular Isolation and Immunofluorescent Staining.

Figure 7:
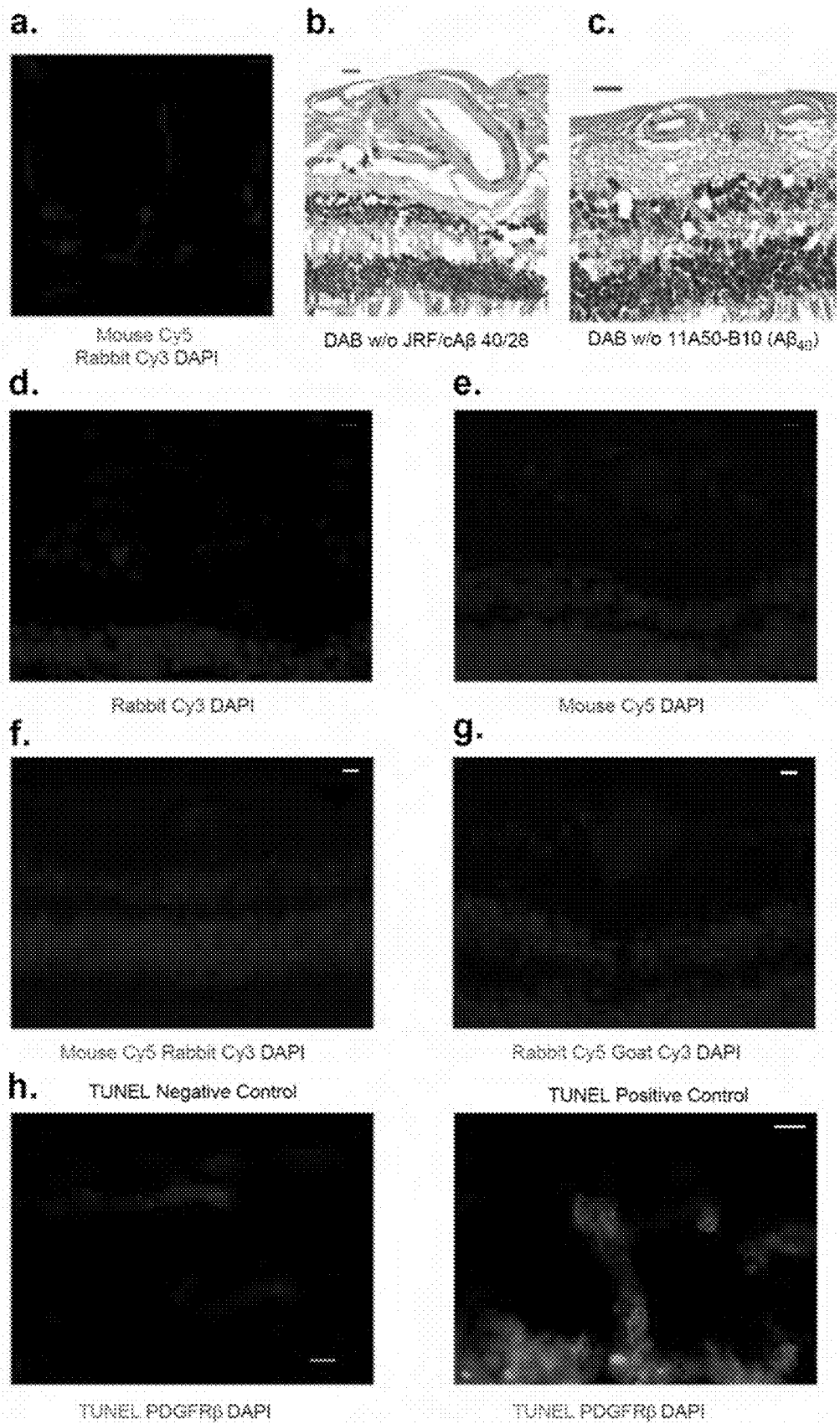
FIG. 7 (panels a-h) shows negative controls for all immunofluorescent staining. a. Representative images of negative controls (primary antibodies omitted) for isolated vascular staining in FIG. 1, with secondary antibodies (donkey anti-rabbit Cy3 and anti-mouse Cy5) and DAPI. Scale bar=10 μm. b-c. Representative images of negative controls (primary antibodies omitted) for DAB staining without (w/o) b. JRF/cAβ 40/28 or c. 11A50-B10 (Aβ40). Scale bars=20 μm. d. Representative image of negative controls (primary antibodies omitted) for retinal cross-section staining in FIG. 2, with secondary antibody (donkey anti-rabbit Cy3) and DAPI. Scale bar=10 μm. e. Representative image of negative controls (primary antibodies omitted) for retinal cross-section staining in FIGS. 3 and 4, with secondary antibody (donkey anti-mouse Cy5) and DAPI. Scale bar=10 μm. f. Representative image of negative controls (primary antibodies omitted) for retinal cross-section staining in FIGS. 3 and 4, with secondary antibodies (donkey anti-rabbit Cy3 and anti-mouse Cy5) and DAPI. Scale bar=10 μm. g. Representative image of negative controls (primary antibodies omitted) for retinal cross-section staining in FIG. 6, with secondary antibodies (donkey anti-goat Cy3 and anti-rabbit Cy5) and DAPI. Scale bar=10 µm. h. Representative images of negative control (without terminal transferase) and positive control (pretreatment with DNaseI) for TUNEL staining experiment in FIG. 6. Scale bars=10 µm.

We modified the retinal vascular isolation method to use on human retinal tissues and immuno-fluorescently label pericytes and amyloidosis [illustrated in FIG. 1a]. This trypsin-induced retinal digestion and vascular network isolation technique was originally developed in 1993 and subsequently modified by replacing trypsin with commercially available elastase. Our modified protocol is as follows: retinal strips from human donors or mouse whole retinas preserved in PFA were first washed in lukewarm running distilled water overnight, then digested in 40 U/mL elastase solution (Merck Millipore, Burlington, MA) for 2 hours at 37° C. After digestion, tissues were incubated in activation solution (Tris buffer at pH 8.5) overnight for extensive digestion. The next day, retinas were transferred to superfrost microscope slides with 1×PBS, then carefully cleaned with rat whisker to remove unwanted tissues under a dissecting microscope. After cleaning non-vascular tissues, 1×PBS was applied 3 times to wash the isolated vascular tissues. When we were able to observe clean vascular tree on slides under dissecting microscope, tissues were mounted on slides carefully without dehydration, then incubated in blocking buffer (Dako #X0909) for 1 hour at room temperature (RT). Primary antibodies were applied to the tissue after blocking, then incubated at 4° C. overnight as listed (antibody information provided in Table 2): 4G8/lectin/PDGFRβ, 6E10/lectin/PDGFRβ, 11A50-B10/lectin/PDGFRβ, 12F4/lectin/PDGFRβ. Tissues were then washed 3 times by PBS and incubated with secondary antibodies against each species (information provided in Table 2) for 2 hours at RT. After rinsing with PBS for 3 times, vascular trees were mounted by Prolog Gold antifade reagent with DAPI (Invitrogen #P36935). For quantification purpose, images were taken on a Carl Zeiss Axio Imager Z1 fluorescence microscope (Carl Zeiss MicroImaging, Inc.) equipped with ApoTome, AxioCam MRm, and AxioCam HRc cameras (for more details see Stereological quantification section below). For representative images, Z-stack images were repeatedly captured at same tissue thickness using a Carl Zeiss 780 Confocal microscope (Carl Zeiss MicroImaging, Inc.). Routine controls were processed using identical protocols while omitting the primary antibody to assess non-specific labeling. Representative images of all negative controls are shown in FIG. 7.

Mice.

The double-transgenic B6.Cg-Tg (APP$_{SWE}$/PS1$_{AE9}$) 85Dbo/Mmjax hemizygous (ADTg) mice strain (MVIRRC stock #34832-JAX|APP/PS1) and their non-Tg littermates (as WT control non-AD) were used for retinal vascular isolation experiments. All mice are on the genetic background of B6. Mice were purchased from MMRRC and later bred and maintained at Cedars-Sinai Medical Center. The mouse experiments were conducted in accordance with Cedars-Sinai Medical Center Institutional Animal Care and Use Committee (IACUC) guidelines under an approved protocol. We used a total of nine 8.5-month-old mice (all males) divided into three groups: perfused WT (n=3), perfused ADTg (n=3), and non-perfused ADTg (n=3) mice. Animals were deeply anesthetized under Ketamine/Xylazine (40-50 mg/kg) before being euthanized either by transcardial perfusion (0.9% ice-cold sodium chloride supplemented with 0.5 mM EDTA) or cervical dislocation (non-perfused group). Eyes were dissected and the retinas were immediately isolated. Using a 25-gauge needle, a hole is poked in the cornea and an incision is made along the ora serrata to remove the lens and cornea-iris. Next, a small incision is made in the sclera-choroid layers toward the optic nerve and using fine forceps, sclera and choroid is gently separated from the retina, which is cleanly snipped at its base from the optic nerve. Care is taken to isolate whole retina undamaged to preserve vasculature network. Following isolation, retinas were fixed in 4% PFA for 7 days. Retinas were then processed for retinal vascular isolation and immunofluorescent staining as described above.

Biochemical Determination of Aβ$_{1-40}$ Levels by Sandwich ELISA.

Frozen human retinal flatmount strips from the temporal hemisphere (ST, TI) were weighed and placed in a tube with cold homogenization buffer [Tris/EDTA buffer pH 9 (DAKO, S2368), 1% Triton X-100 (Sigma, T8787), 0.1% NaN$_3$ (Sigma, 438456) and 1× Protease Inhibitor cocktail set I (Calbiochem 539131)], then homogenized by sonication (Qsonica Sonicator M-Tip, Amplitude 4, 6 W, for 90 s; sonication pulse was stopped every 15 s to allow the cell suspension to cool down for 10 s) and positioned the ultrasonic probe inside the tube that was placed in ice water. Next, retinal strip homogenates were incubated for 1 hr at 98° C. in a water bath. After determination of the protein concentration (Thermo Fisher Scientific), retinal $A\beta_{1-40}$ was determined using an anti-human $A\beta_1 40$ end-specific sandwich ELISA kit (Thermo Fisher, KHB3481).

Immunofluorescent Staining of Retinal Cross-Sections.

After deparaffinization, retinal cross-sections were treated with antigen retrieval solution at 98° C. for 1 hr (PH 6.1; Dako #S1699) and washed in PBS. Retinal sections were then incubated in blocking buffer (Dako #X0909), followed by primary antibody incubation (information provided in Table 2) overnight in 4° C. with the following combinations: PDGFRβ (1:200)/lectin (1:200)/11A50-B10 (1:200), PDGFRβ (1:200)/lectin (1:200)/12F4 (1:200), CD31 (1:50)/ JRF/cAβ 40/28 #8152 (1:2000), LRP-1 (1:200)/PDGFRβ (1:200)/lectin (1:200), cleaved caspase-3 (1:200)/PDGFRβ (1:200)/lectin (1:200). Alexa Fluor 488-conjugated tomato lectin was used to visualize blood vessel cells. Retinal sections were then washed 3 times by PBS and incubated with secondary antibodies against each species (1:200, information provided in Table 2) for 2 hr at RT. After rinsing with PBS for 3 times, sections were mounted with Prolong Gold antifade reagent with DAPI (Thermo Fisher #P36935). Images were repeatedly captured at the same focal planes with the same exposure time using a Carl Zeiss Axio Imager Z1 fluorescence microscope (Carl Zeiss MicroImaging, Inc.) equipped with ApoTome, AxioCam MRm, and AxioCam HRc cameras. Images were captured at 20×, 40×, and 63× objectives for different purposes (for more details see Stereological quantification section below). Routine controls were processed using identical protocols while omitting the primary antibody to assess nonspecific labeling. Representative images of negative controls are shown in FIG. 7.

TABLE 2

List of antibodies used in the study

| Antigen and Clone | Source Species | Dilution | Commercial Source | Catalog. # |
|---|---|---|---|---|
| Primary antibody | | | | |
| PDGFRβ pAb | Goat | 1:200 | R&D Systems | Aβ85 |
| Aβ40 (11A50-B10) mAb | Mouse | 1:250 DAB* 1:200 FL** | Biolegend | 805401 |
| JRF/cAβ40/28 # 8152 mAb | Mouse | 1:2500 DAB* 1:2000 FL** | Janssen Pharmaceutica | N/A |
| CD31 pAb | Rabbit | 1:50 | Abcam | ab28364 |
| Aβ42 (12F4) mAb | Mouse | 1:200 | Biolegend | 805501 |
| 4G8 mAb | Mouse | 1:200 | Biolegend | 800701 |
| 6E10 mAb | Mouse | 1:200 | Biolegend | 803001 |
| Caspase-3 pAb | Rabbit | 1:500 | Abcam | ab13847 |
| Cleaved Caspase-3 pAb | Rabbit | 1:200 | Cell Signaling | 9661 |
| LRP-1 mAb | Rabbit | 1:200 | Abcam | ab92544 |
| Alexa Fluor 488-conjugated tomato lectin | Lycopersicon esculentum | 1:200 | Dylight | DL-1174 |
| Secondary antibody | | | | |
| Cy3 (anti-rabbit, anti-goat) | Donkey | 1:200 | Jackson ImmunoResearch Laboratories | |
| Cy5 (anti-mouse, anti-rabbit) | Donkey | 1:200 | Jackson ImmunoResearch Laboratories | |
| Alexa 647 (anti-goat) | Donkey | 1:200 | Jackson ImmunoResearch Laboratories | |

IHC—immunohistochemistry; ICC—immunocytochemistry; pAb—polyclonal antibody; mAb—monoclonal antibody; *DAB—peroxidase-based immunohistochemistry visualized with DAB substrate; **FL—fluorescence-based immunohistochemistry. If not marked otherwise, antibody dilution is indicated for immunofluorescent essay.

Peroxidase-Based Immunostaining of Aβ.

Fixed brain sections and retinal cross-sections after deparaffinization were treated with target retrieval solution (pH 6.1; S1699, DAKO) at 98° C. for 1 hour and washed with PBS. In addition, treatment with 70% formic acid (ACROS) for 10 min at RT was performed on brain sections and retinal cross-sections before staining for Aβ. Peroxidase-based immunostaining was performed. For antibodies list and dilutions, see Table 2. Prior to peroxidase-based immunostaining, the tissues were treated with 3% $H_2O_2$ for 10 minutes, and two staining protocols were used: (1) Vectastain Elite ABC HRP kit (Vector, PK-6102, Peroxidase Mouse IgG) according to manufacturer's instructions or (2) All Dako reagents protocol. Following the treatment with formic acid, the tissues were washed with wash buffer (Dako S3006) for 1 hour, then treated with $H_2O_2$ and rinsed with wash buffer. Primary antibody (Ab) was diluted with background reducing components (Dako S3022) and incubated with the tissues for 1 hour at 37° C. for JRF/cAβ 40/28 #8152, or overnight at 4° C. for 11A50-B10 ($A\beta_{40}$) mAbs. Tissues were rinsed twice with wash buffer on a shaker and incubated for 30 minutes at 37° C. with secondary Ab (goat anti mouse ab HRP conjugated, DAKO Envision K4000), then were rinsed again with wash buffer. For both protocols, diaminobenzidine (DAB) substrate was used (DAKO K3468). Counterstaining with hematoxylin was performed followed by mounting with Faramount aqueous mounting medium (Dako, S3025). Routine controls were processed using identical protocols while omitting the primary antibodies to assess nonspecific labeling. Representative images of negative controls are shown in FIG. 7.

Transmission Electron Microscopy (TEM) Analysis.

Analyses of a retinal whole mount from an AD donor retina that was pre-stained with anti-$A\beta_{42}$ mAb (12F4), and a high-sensitivity immunoperoxidase-based system with 3,3' Diaminobenzidine (DAB) substrate chromogen were performed using transmission electron microscopy. Stained tissues were processed for electron microscopic imaging; the samples were dehydrated in serially graded ethanol and then infiltrated in Eponate 12 (Ted Pella, Inc. Redding, CA, USA) prior to embedding between two acetate sheets. Ultrathin sections of retina were cut in cross sections at a thickness of 70 nm, examined on a JEOL JEM 2100 (JEOL USA, Peabody, MA, USA), and photographed with the Onus SC1000B digital camera (Gatan, Pleasanton, CA, USA). Images were processed and colorized using Adobe Photoshop CS4 (Adobe Inc., San Jose, CA, USA).

TUNEL Assay for Detection of Apoptotic Retinal Pericytes.

Formalin-fixed paraffin-embedded retinal cross-sections after deparaffinization were washed with PBS, and then incubated with Proteinase-K (Recombinant PCR grade, 15 μg/ml in 10 mM Tris/HCL pH 7.6; Roche Diagnostics GmbH; 03115836001) at 37° C. for 20 minutes. Next, slides were washed with PBS and incubated with TUNEL reaction mixture (50 μl on each slide; Roche Diagnostics GmbH; 11684795910) at 37° C. for 60 minutes, in a humidified chamber in dark (the samples were covered with parafilm to ensure a homogeneous spread of TUNEL reaction and to avoid evaporation loss). Afterward, slides were washed with PBS and fluorescent-based immunostaining was performed using blocking solution (DAKO X0909) for 45 minutes at RT. The tissues were incubated with primary antibody, goat anti PDGFRβ, overnight at 4° C., then the secondary antibody, donkey anti goat Alexa 647, was applied for 1 hour at RT. Then, the samples were washed with PBS and covered with ProLong™ Gold antifade mounting media with DAPI (Molecular Probes; #P36935). Negative and positive controls were included (see FIG. 7) in this experimental setup: for TUNEL negative control the retinal tissues were incubated with only 50 µl of TUNEL label solution (without the TUNEL Enzyme solution—terminal transferase) instead of TUNEL reaction mixture. For TUNEL positive control the retinal tissues were incubated with DNase I (1000 U/ml in 50 mM Tris-HCL, pH 7.5; Worthington Biochemical Corp. Code D) to induce DNA strand breaks, prior to labeling procedure. The retinal tissue sections were then evaluated under fluorescent microscope.

Stereological Quantification.

For FIG. 1 of isolated retinal blood vessels, quantification was performed from 5 AD donors and 5 age- and sex-matched CN controls. The fluorescence of specific signals was captured using the same setting and exposure time for each image and human donor, with a Z-stack of 10 µm thick using Axio Imager Z1 microscope (with motorized Z-drive) with AxioCam MRm monochrome camera ver. 3.0 (at a resolution of 1388×1040 pixels, 6.45 µm×6.45 µm pixel size, dynamic range of >1:2200, that delivers low-noise images due to Peltier-cooled sensor). Images were captured at 40× objective, at respective resolution of 0.25 µm. Fifteen images were taken randomly from each region of central, mid-, and far-peripheral retina (five from each region) per subject. Acquired images were converted to greyscale and standardized to baseline using a histogram-based threshold in the NIH ImageJ software (version 1.52o). For each biomarker, total area of immunoreactivity was determined using the same threshold percentage from the baseline in ImageJ (with same percentage threshold setting for all diagnostic groups). The images were then subjected to particle analysis for lectin and Aβ to determine IR area. Pericyte number was based on fifteen images, averaging the number in each microscopic visual field (covering $1.8 \times 10^4$ µm$^2$ area), per human donor. We used the grid mode in ImageJ to manually count the number of pericytes. The ratio of Aβ to lectin was calculated by dividing Aβ IR area by lectin IR area in each of the fifteen images (described above) and averaging the values per human donor. The sum of Aβ IR area from an identical number of randomly selected pericytes (n=10) from each human donor was used to calculate Aβ in pericytes. An identical region of interest was used for the standardized histogram-based threshold technique and subjected to particle analysis.

For FIGS. 2-6 with analysis of retinal cross-sections and quantifications of PDGFRβ, vascular Aβ$_{42}$, vascular Aβ$_{40}$, Aβ$_{40}$, LRP-1, cleaved caspase-3 and TUNEL, images were also acquired at the same setting and exposure time for each experiment, using the Axio Imager Z1 microscope, as described above. Images were captured at either 20× or 40× objectives, at respective resolutions of 0.5 and 0.25 µm. Three images were taken from central and far-peripheral retina and 4 images were taken from mid-peripheral retina (as shown in FIG. 2a-b). For each biomarker, the total area of immunoreactivity was determined using the same threshold percentage from the baseline in ImageJ (with same percentage threshold setting for all images), then subjected to particle analysis for each biomarker to determine their area or area percentage. For vascular PDGFRβ, vascular Aβ$_{42}$ and Aβ$_{40}$, and vascular LRP-1, area of blood vessels was chosen to acquire positive immunoreactive (IR) area percentage. For total retinal Aβ$_{40}$ and total LRP-1 area, we chose the whole retina and documented total IR area of each biomarkers. Quantification of cleaved caspase-3$^+$ and TUNEL$^+$ pericytes was performed by randomly choosing 10-15 pericytes from each human donor, followed by manually counting using the grid in ImageJ. Then a percentage of cleaved caspase-3$^+$ or TUNEL$^+$ pericytes was calculated.

For vascular markers of Aβ$_{42}$, Aβ$_{40}$, and PDGFRβ, analysis was performed separately for longitudinal blood vessels and vertical blood vessels. Retinal cross-sections in this study were cut sagittally from flatmount strips, hence blood vessels were categorized by the shape of lectin stain: either as vertical blood vessels (≥10 µm in diameter) or longitudinal blood vessels (~10 µm in diameter). Note: for vertical blood vessels, the vascular wall area (determined by lectin) was selected for analysis, while excluding the blood vessel lumen. For longitudinal blood vessels, the total blood vessel including lumen and wall were selected for quantitative analysis. Dotted eclipse or rectangle frames were added to the representative images to highlight the area of quantification for both vertical blood vessels and longitudinal blood vessels.

Statistical Analysis.

GraphPad Prism 8.1.2 (GraphPad Software) was used for analyses. A comparison of three or more groups was performed using one-way ANOVA followed by Sidak's multiple comparison post-hoc test of paired groups. Groups with two independent variables/factors were analyzed by two-way ANOVA followed by Sidak's multiple comparison test to further understand interaction between the two independent variables. Two-group comparisons were analyzed using a two-tailed unpaired Student t-test. The statistical association between two or more variables was determined by Pearson's correlation coefficient (r) test (Gaussian-distributed variables; GraphPad Prism). Pearson's r indicates direction and strength of the linear relationship between two variables. Required sample sizes for two group (differential mean) comparisons were calculated using the nQUERY t-test model, assuming a two-sided a level of 0.05, 80% power, and unequal variances, with the means and common standard deviations for the different parameters. Results are expressed as mean±standard error of the mean (SEM). P value less than 0.05 is considered significant.

Figure 8:
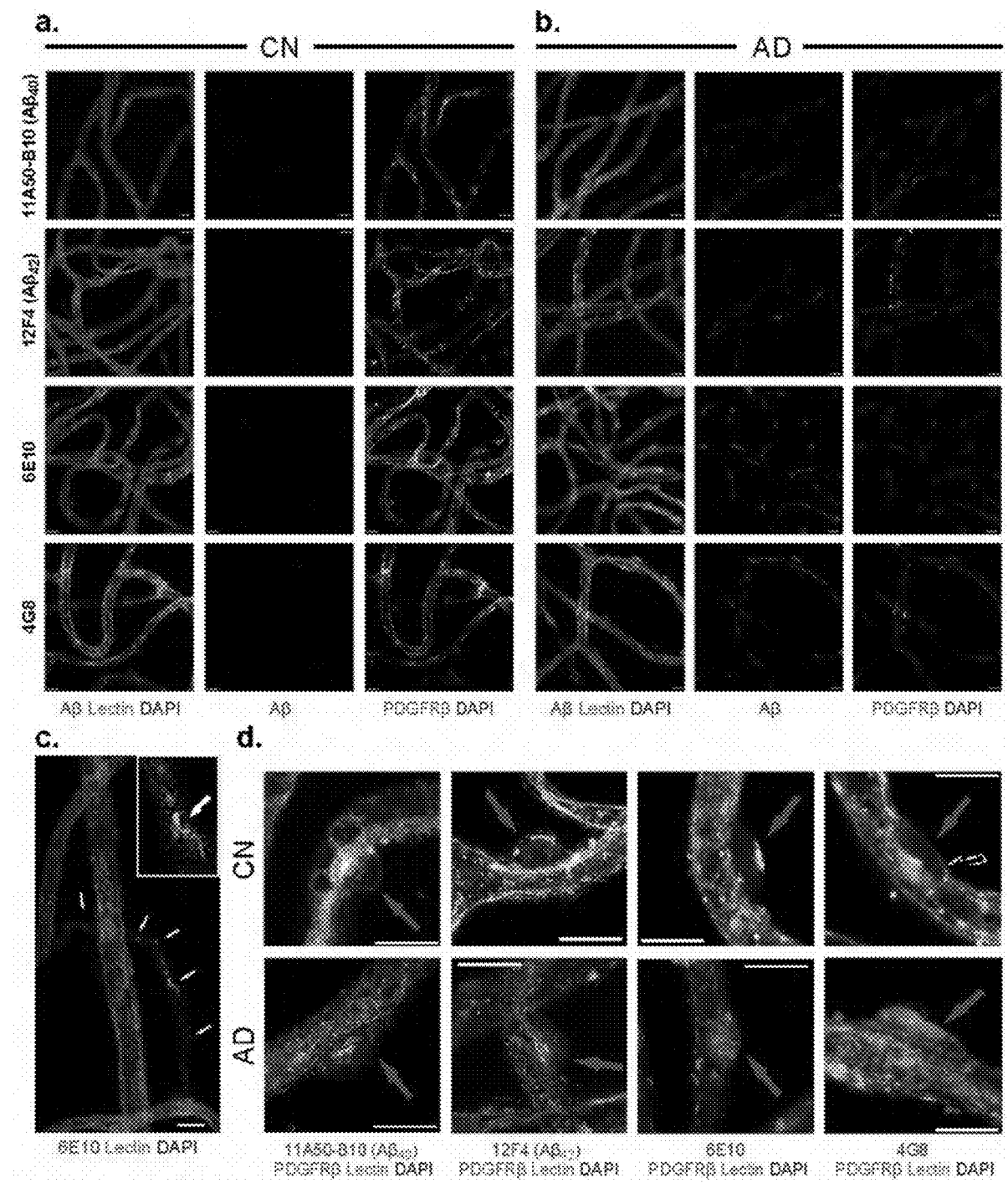
FIG. 8 (panels a-d) shows extended representative images for FIG. 1 on retinal microvascular Aβ and PDGFR/pericytes. a-b. Separate channels of representative fluorescent images for Aβ (11A50-B10, 12F4, 6E10 or 4G8 as indicated, red), PDGFRβ (pericytes, white). lectin (glycoprotein in blood vessel, green) and DAPI (nuclei, blue) on isolated retinal microvasculature from age and sex-matched human donors with AD (n=5) or cognitively normal (CN, n=5). c. Aβ (6E10, red), lectin (green) and DAPI (blue) staining showing Aβ deposits in a degenerated, acellular capillary (indicated by arrows) Upper right image shows zoomed-in image from the original. d. Enlarged confocal images of retinal microvascular pericytes from AD and CN donors (AD-red, PDGFRβ-white, lectin-green, DAPI-blue)_Scale bars=10 µm.

Retinal Pericyte Loss Along with Vascular Aβ Deposits Including within Pericytes in Isolated Microvasculature from Postmortem Retina of AD Patients To exclusively investigate the extent of retinal microvascular amyloidosis and possible pericyte degeneration in AD without interference from other retinal tissues, we enzymatically digested retinas, preserved solely the vascular network, and subsequently conducted fluorescent immunostaining for blood vessels (lectin), PDGFRβ, and different types of Aβ (FIG. 1; extended data in FIG. 8). Our modified method for human retinal vascular isolation and immunofluorescence is illustrated in FIG. 1a. This approach was performed on postmortem retinas isolated from a cohort of age- and sex-matched human subjects with AD diagnosis (avg. age 79.20±10.9 years, 3 females/2 males, CAA score 1.7±0.27) and CN controls (avg. age 75.60±5.63 years, 2 females/3 males, no known CAA). Intense deposits of Aβ$_{42}$ were visible in AD retinal microvasculature including colocalization with lectin, as compared to CN retina (FIG. 1b).

Vascular Aβ$_{42}$ accumulation was also detected inside retinal pericytes in AD but not in CN (FIG. 1c). This is further supported by immunostaining with other antibodies against Aβ, including 11A50-B10 (Aβ$_{40}$), 6E10, and 4G8 (FIG. 1d-e, FIG. 8a-d). In addition, a substantial decrease in PDGFRβ expression was observed in retinal microvasculature from AD as compared to CN controls (FIG. 1f; see lectin/PDGFRβ co-labeling in yellow). A quantitative analysis of retinal microvascular pericyte count per microscopic visual field ($1.8 \times 10^4$ µm$^2$) revealed a significant 37% pericyte loss in AD compared to controls (FIG. 1g). By quantification of Aβ-immunoreactive area normalized for the lectin-positive vascular area, a significant 5.6-fold increase of Aβ deposition in retinal microvasculature was measured in AD vs. CN (FIG. 1h). Moreover, a substantial 8.7-fold increase of Aβ-immunoreactive area within retinal pericytes was detected (FIG. 1i). Further, Aβ deposits were identified inside degenerated, acellular retinal capillaries that appear to lose lectin expression (FIG. 8c).

Figure 9:
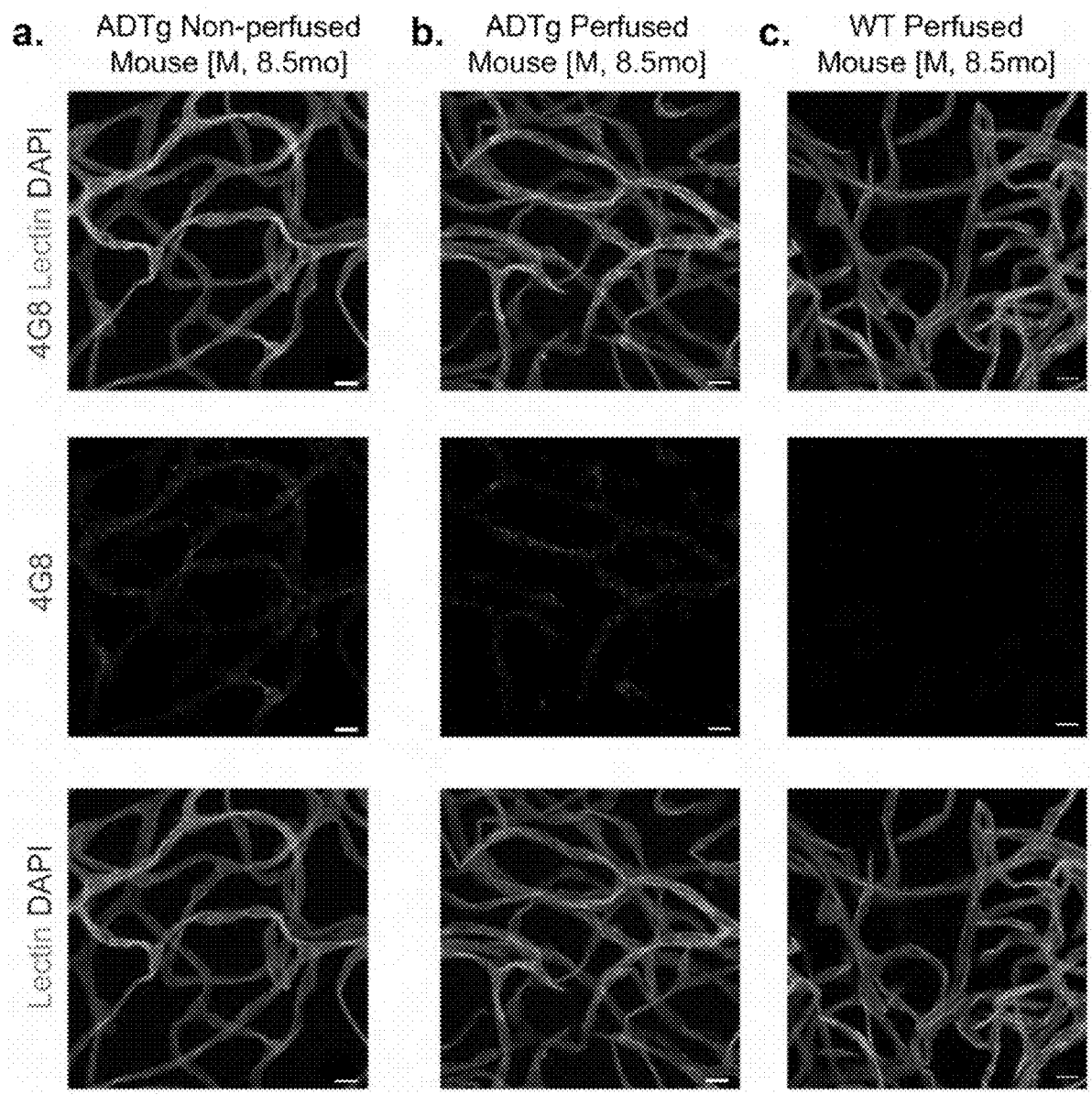
FIG. 9 (panels a-c) shows significant retinal vascular Aβ deposition in perfused transgenic ADTg mice. a-c. Representative fluorescent images for Aβ (4G8, red), lectin (glycoprotein in blood vessel, green) and DAPI (nuclei, blue) on isolated retinal microvasculature from a. non-perfused 8.5 month old male ADTg mice, or b. perfused 8.5 month old male ADTg mice, and c. perfused 8.5 month old male wild type mice. Scale bars=10 µm.
Figure 10:
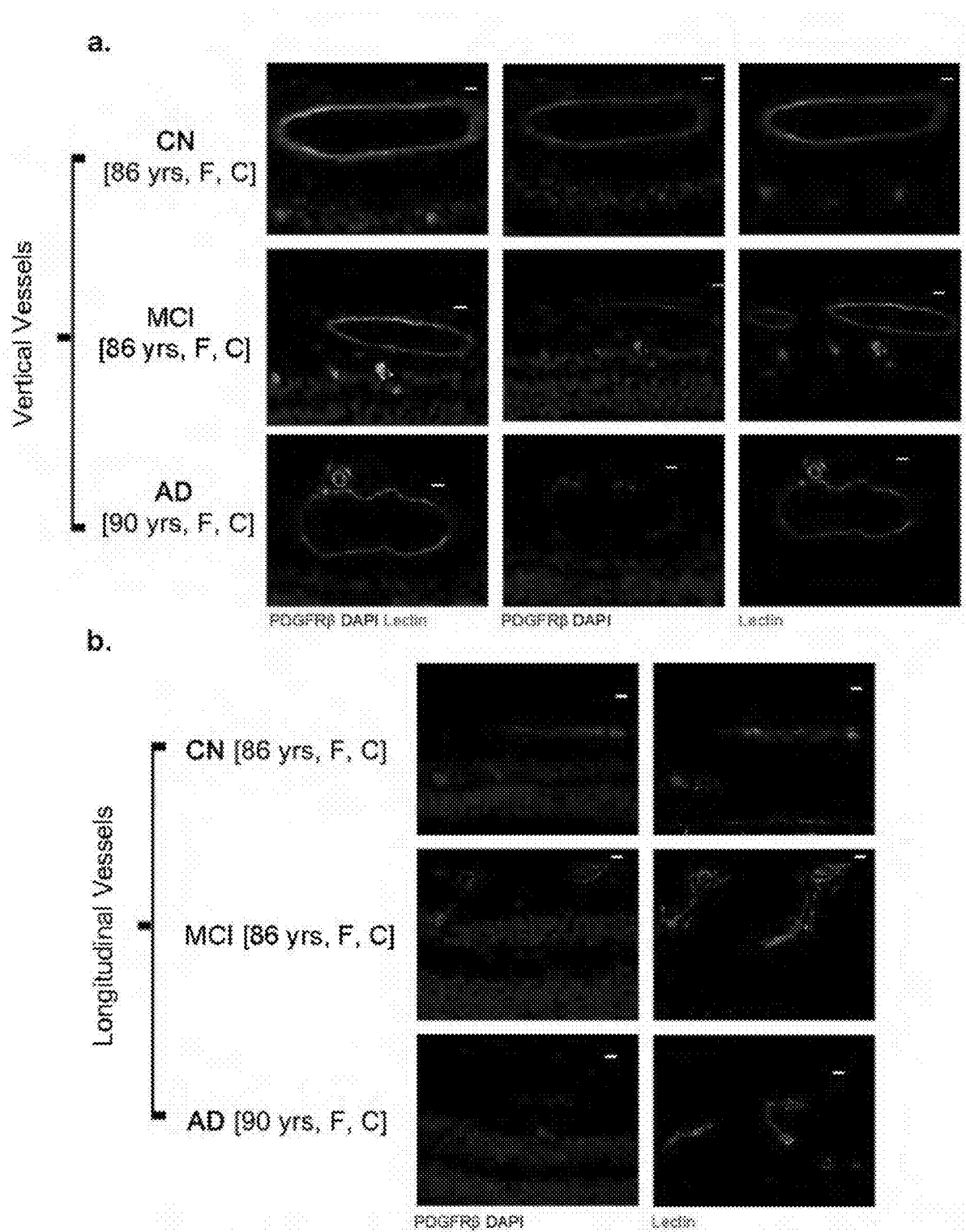
FIG. 10 (panels a-b) shows extended representative images for FIG. 2 on retinal vascular PDGFRβ. a-b. Merged and separate channels of representative fluorescent images for PDGFR~ (red), lectin (glycoprotein in blood vessel, green) and DAPI (nuclei, blue) in paraffin-embedded retinal cross-sections isolated from age and sex-matched human donors with AD, MCI or cognitively normal (CN). a. Vertical (V) and b. Longitudinal (L) blood vessels are shown. Scale bars=10 µm.

Next, we validated the presence of Aβ deposition in isolated retinal blood vessel walls in double-transgenic murine models of AD (ADTg). Performing the blood perfusion procedure prior to retinal vascular extraction allowed us to exclude the contribution of circulating Aβ in the blood. A comparison between perfused and non-perfused ADTg mice and their non-transgenic littermates (WT) revealed that regardless of blood perfusion, there were substantial amounts of retinal vascular Aβ deposits in ADTg mice (FIG. 9).

Early and Progressive Loss of Retinal Vascular PDGFRβ is Associated with CAA and Brain Amyloid Plaque Pathology Retinal vascular pathology was further investigated in cross-sections prepared and analyzed from a larger cohort of 46 human eye donors with pre-mortem diagnosis of AD (n=21), MCI (n=11), or CN (n=14). There were no significant differences in mean age, sex, or PMI between the three diagnostic groups (for more details see Tables 3-4). Histological samples from this cohort were prepared through dissection of retinal strips (2 mm) from four quadrants (superior-temporal—ST, inferior-temporal—TI, inferior-nasal—IN, and superior-nasal—NS) spanning from the optic disc to the ora serrata, processed into paraffin-embedded cross-sections, and immunostained (FIG. 2a-b).

TABLE 3

Demographic data on human eye donors evaluated by retinal cross-section.

| | CN | MCI | AD | F | P |
|---|---|---|---|---|---|
| No. of Subjects (n = 46) | 14 (9F, 5M) | 11 (5F, 6M) | 21 (13F, 8M) | — | — |
| Age ± SD [Years] | 79.14 ± 10.5 F: 79.78 ± 12.3 M: 78.0 ± 7.3 | 87.09 ± 5.4 F, 90.2 ± 3.6 M, 84.5 ± 5.5 | 81.81 ± 14.9 F, 85.61 ± 12.6 M, 67.2 ± 16.7 | 1.404 | 0.2567 |
| Race (%) | 13C (92.9%) 1B (7.1%) | 7C (81.8%) 1H (9.1%) 1B (9.1%) | 16C (76.2%) 1B (4.8%) 4A (19%) | — | — |
| PMI [Hours] | 7.5 ± 2.3 | 9.5 ± 5.0 | 7.6 ± 3.7 | 1.120 | 0.3355 |

CN cognitively normal; MCI, mild cognitive impairment; AD, Alzheimer's disease; F, female, M, male; SD, standard deviation; C, Caucasian; B, Black; H, Hispanic; A, Asian, UK Unknown; PMI, post-mortem interval; Values are presented as mean ± SD. F and P values were determined by one-way ANOVA with Sidak'smultiple comparison test.

TABLE 4

Neuropathological evaluation in a subset of human donors evaluated by retinal cross-section.

| Brain Scores | CN* (n = 1) | MCI (n = 7) | AD (n = 17) |
|---|---|---|---|
| CAA | 1 | 0.7 ± 0.97 | 1.3 ± 0.75 |
| Aβ Plaque | 0.545 | 2.11 ± 0.77 | 2.8 ± 0.93 |
| Neurofibrillary Tangle | 0.98 | 1.46 ± 0.99 | 2.5 ± 1.3 |
| Neuropil Thread | 0.86 | 1.1 ± 0.93 | 1.13 ± 1.2 |
| Atrophy | 0.8 | 1.09 ± 1.08 | 2.05 ± 1.2 |

CN cognitively normal; MCI, mild cognitive impairment; AD, Alzheimer's disease; A neuropathological score from one CN donor. CAA, cerebral amyloid angiopathy.

Initially, we assessed retinal vascular PDGFRβ expression by fluorescent immunostaining in lectin+ blood vessels. We classified and analyzed two types of blood vessels by shape and size: longitudinal (~10 μm in diameter) and vertical (≥10 μm in diameter). The examination of small-size longitudinal vessels allowed for analysis of PDGFRβ+ pericytes that exist in capillaries and pericytic venules, while excluding vSMCs in larger-size vessels. The separate analysis of vertical vessels covered both PDGFRβ-expressing pericytes and vSMCs. We observed a notable decrease of PDGFRβ signal in both retinal longitudinal and vertical blood vessels in MCI, which was further exacerbated in AD (FIG. 2c-d, FIG. 10a-b). Stereological analysis of percent retinal PDGFRβ area in retinal cross-sections is shown in a subset of age- and sex-matched AD, MCI, and CN subjects (n=38, avg. age SD: AD=81.2±15.3, MCI=86.3±6.2 and CN=78.1±10.4). Data indicate a significant (38%) early loss of retinal PDGFRβ in vertical vessels of MCI as compared to CN controls, whereas a more profound reduction (72%) of vertical vascular PDGFRβ was detected in AD retina (FIG. 2e). To evaluate the relationship between retinal PDGFRβ and CAA scores, we applied Pearson's correlation coefficient (r) analysis between the two parameters in a cohort of cognitively impaired individuals. We found a significant inverse relationship between retinal PDGFRβ levels and brain CAA score in MCI and AD (FIG. 2f), suggesting that retinal vascular changes in the form of PDGFRβ loss may predict amyloid angiopathy severity in the brains of these patients.

Figure 11:
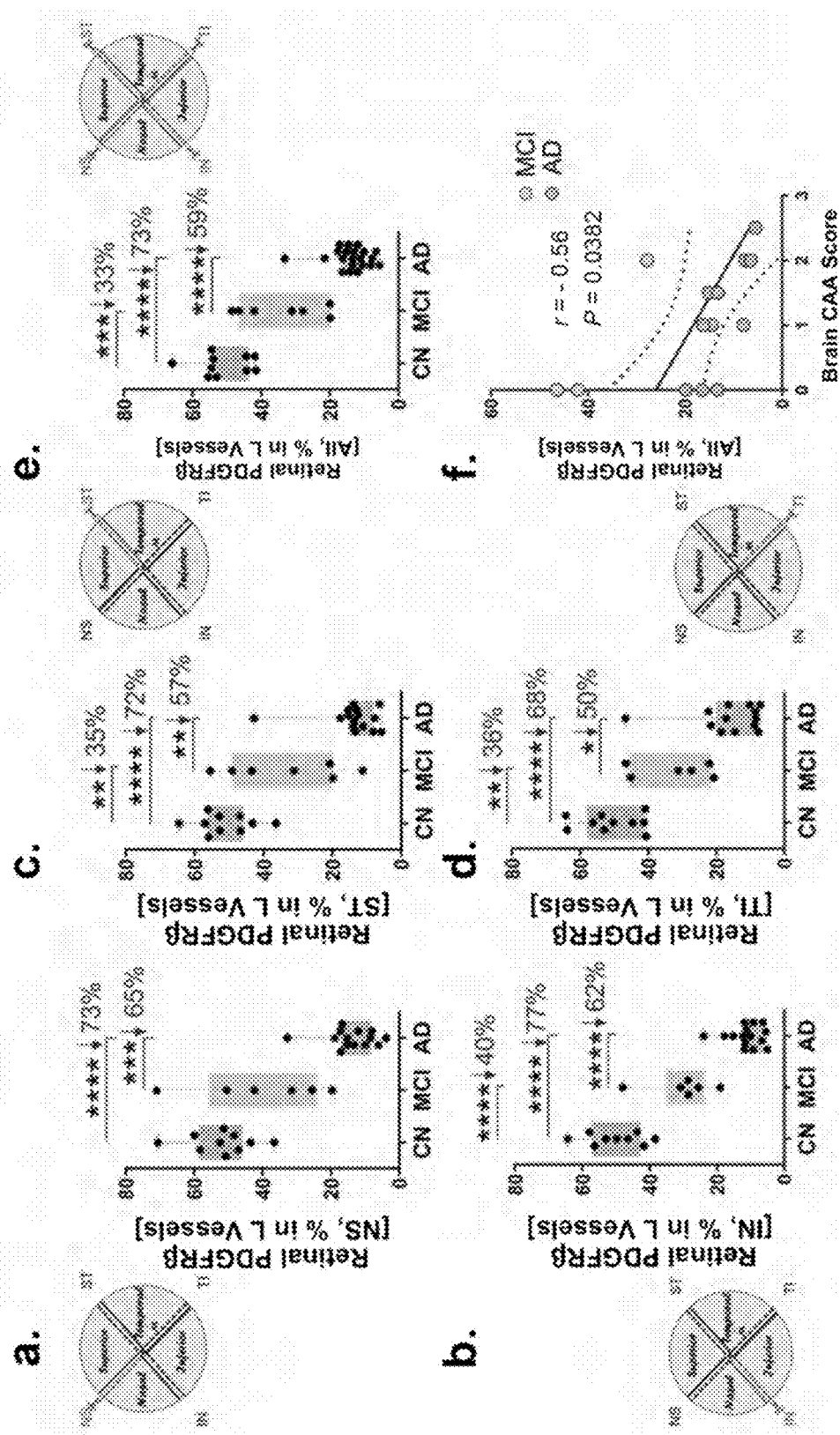
FIG. 11 (panels a-g) shows extended data on retinal PDGFRβ in longitudinal vasculature from all retinal quadrant regions in AD, MCI and CN human donors and mapping of PDGFRβ. a-d. Quantitative analysis of % PDGFRβ-immunoreactive area in longitudinal (L) vessels from each retinal quadrant separately: a. NS, b. IN, c. ST, d. TI in total cohort of AD (n=21), MCI (n=7) and cognitively normal (CN) (n=10) human donors. e-f. Quantitative analysis of retinal % PDGFRβ immunoreactivity in L vasculature (average of all four quadrants): e. subjects stratified by clinical diagnosis (n=38) and f. Pearson's correlations against brain CAA scores in a subset of this cohort (n=14). g. Mapping of vertical (V) vascular PDGFRβ in four retinal quadrants. (* indicates AD vs. CN, * indicates AD vs. MCI) Data from individuals as well as group means and SEMs are shown. *p<0.05, p<0.01, *p<0.001, ****p<0.0001, by one-way ANOVA test with Sidak's post-hoc multiple comparison test. Percent change are shown in red.
Figure 11:
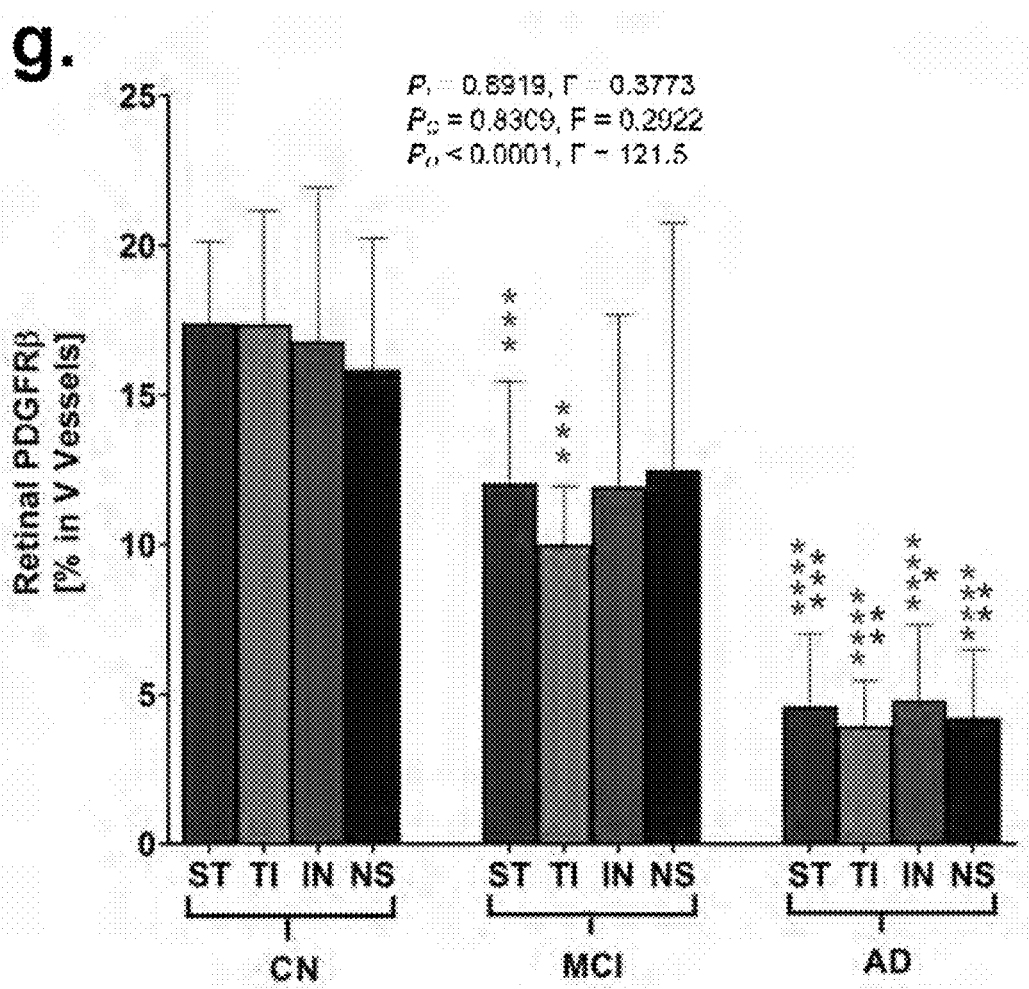

To measure changes in retinal PDGFRβ distribution across the four retinal quadrants, we analyzed PDGFRβ area coverage in human subjects that were stratified by their clinical diagnosis and for each quadrant separately (vertical vessels in FIG. 2g-j, longitudinal vessels in FIG. 11a-e; for comparisons between the four quadrants see FIG. 11g). Our analysis indicated that the temporal hemiretina (ST and TI) had early substantial decreases in vertical vascular PDGFRβ in MCI (FIG. 2i-j), whereas the percentage of PDGFRβ area loss was only significant at later disease stages in the nasal hemiretinal quadrants (NS and IN), as seen in AD (FIG. 2g-h). Consistent with the vascular impairment seen in vertical vessels, early and progressive loss of PDGFRβ+ pericytes residing along longitudinal capillaries and post-capillary venules was detected in MCI and AD (FIG. 11a-e). A significant inverse association with neuropathological CAA scores was also identified among individuals with MCI and AD (FIG. 11f).

Moreover, in subjects with neuropathological reports (n=20), retinal PDGFRβ loss inversely correlated with brain Aβ plaques (NP, DP, IP) and NTs, as summarized in FIG. 2k-1 heat-map (extended data on Pearson's r correlations for pre-defined brain regions in Table 5). In particular, significant correlations between retinal vascular PDGFRβ and brain neuritic plaques were detected for overall brain severity score, as well as separately for the hippocampus, entorhinal cortex, and visual association cortex (FIG. 2k-1). In a subset of subjects where MMSE scores were available, we identified a significant correlation between retinal PDGFRβ loss and cognitive impairment (FIG. 2m). While PDGFRβ in most of retinal quadrants significantly correlated with MMSE scores, the most significant correlation was found with the superior retina (FIG. 2m; extended data on Pearson's r correlations between MMSE scores against retinal PDGFRβ, per each retinal subregion, are provided in Table 6).

TABLE 5

Multiple correlation analysis between % retinal PDGFβ area in vessels and neuropathological

|  |  | Neuritic Plaques | Immature Plaques | Diffuse Plaque | NFTs (Silver) | Neuropil Threads |
|---|---|---|---|---|---|---|
| All Brain | r | −0.50 | −0.36 | −0.45 | −0.07 | −0.03 |
|  | P | *0.0264* | 0.1224 | 0.0443 | 0.7801 | 0.9022 |
| Hippocampus | r | −0.61 | −0.40 | −0.38 | −0.17 | 0.12 |
|  | P | *0.0046* | 0.0802 | 0.0986 | 0.4622 | 0.6184 |
| Entorhinal Cortex | r | 0.26 | −0.01 | 0.35 | 0.15 | −0.23 |
|  | P | *0.0433* | 0.2598 | 0.3403 | 0.4902 | 0.5154 |
| Frontal Cortex | r | −0.01 | −0.30 | −0.04 | −0.38 | −0.34 |
|  | P | 0.9543 | 0.1990 | 0.8586 | 0.1027 | 0.1396 |
| Temporal Cortex | r | −0.06 | −0.33 | −0.35 | −0.09 | −0.18 |
|  | P | 0.8066 | 0.1551 | 0.1265 | 0.7234 | 0.4504 |
| Parietal Cortex | r | 0.05 | 0.01 | −0.28 | −0.33 | −0.39 |
|  | P | 0.8431 | 0.9769 | 0.2280 | 0.1511 | 0.0938 |
| PV. Ctx. A-17 | r | −0.32 | −0.35 | −0.46 | −0.25 | −0.55 |
|  | P | 0.2134 | 0.1540 | 0.0568 | 0.3412 | *0.0175* |
| VA. Ctx. A-18 | r | −0.74 | −0.30 | −0.58 | −0.39 | −0.46 |
|  | P | *0.0015* | 0.2598 | *0.0192* | 0.1457 | 0.0872 |

Correlations between retinal % area of PDGFβ in vessels and the corresponding neuropathological measurements: neuritic plaques, immature plaques, diffuse plaques, neurofibrillary tangles (NFTs; by Gallyas Silver stain), neuropil threads by sliver stain. Scores are given as: 0 = None, 1 = Sparse (−5), 3 = Moderate (6-20), 5 = Frequent (21-30 or above) based on pathological reports. Analysis was performed for mean of all brain regions and separated for each brain region. Sample size: n = 14 for AD, n = 5 for MCI, n = 1 for CN. Statistical significance P is <0.05 indicated in bold. Pearson's r correlations analysis was applied to deteimine relationships; PV—primary visual; VA—visual association; Ctx—cortex.

TABLE 6

Correlation between % PDGFRβ immunoreactive area per retinal subregions and MMSE scores.

| Retinal Regions | Total | ST | TI | IN | NS | Superior | Inferior | Nasal | Temporal |
|---|---|---|---|---|---|---|---|---|---|
| r | 0.77 | 0.89 | 0.82 | 0.71 | 0.92 | 0.92 | 0.71 | 0.73 | 0.89 |
| P | 0.0156 | 0.016 | 0.1825 | 0.0499 | 0.0271 | 0.0036 | 0.0486 | 0.0411 | 0.0171 |
| N | 9 | 6 | 4 | 8 | 5 | 7 | 8 | 8 | 6 |

Total; total retinal average; ST, superiortemporal; TI, temporalinferior; IN, inferioimasal; NS, nasalsuperior; Superior, mean of ST and NS values; Inferior, mean of TI and IN values; Nasal, mean of IN and NS values; Temporal, mean of ST and TI values. N, number of pairs. Statistical significance P is <0.05. Pearson's r correlations analysis was applied to determine relationships Accumulation of Retinal $A\beta_{42}$ in Blood Vessels and Pericytes in MCI and AD Our group and others have demonstrated the existence of retinal Aβ deposits in AD patients, our next question was whether vascular PDGFRβ loss is associated with increased vascular Aβ deposition in postmortem retinas from MCI and AD patients. To this end, we studied retinal vascular $A\beta_{42}$ pathology in a cohort of age- and sex-matched human eye donors (n=31, avg.±SD age: AD=82.8±18.4, MCI=87.8±5.5, CN=78.8±10.3; FIG. 3). We analyzed percent 12F4+$A\beta_{42}$-IR area separately for vertical and longitudinal retinal vessels (FIG. 3a-d); the two types of blood vessels were classified as detailed above. The AD retina displays substantially more vascular $A\beta_{42}$ as compared to both MCI and CN retinas (FIG. 3a-b; additional image panels in FIG. 12a-b). In our quantitative IHC analyses, to avoid signal from circulating blood Aβ, in the vertical vessel analyses we quantify the immunoreactive area by selecting the vascular wall region and excluding the lumen area (see example of dotted eclipse frames in FIG. 3a). Analysis of vertical vascular $A\beta_{42}$ confirmed a significant increase in the retina of MCI and AD compared to CN controls (FIG. 3c). Analysis of retinal longitudinal vessels also indicated a significant increase in $A\beta_{42}$ burden in AD compared to MCI and CN controls (FIG. 3d), representing accumulation of both circulating and vascular $A\beta_{42}$.

Figure 12:
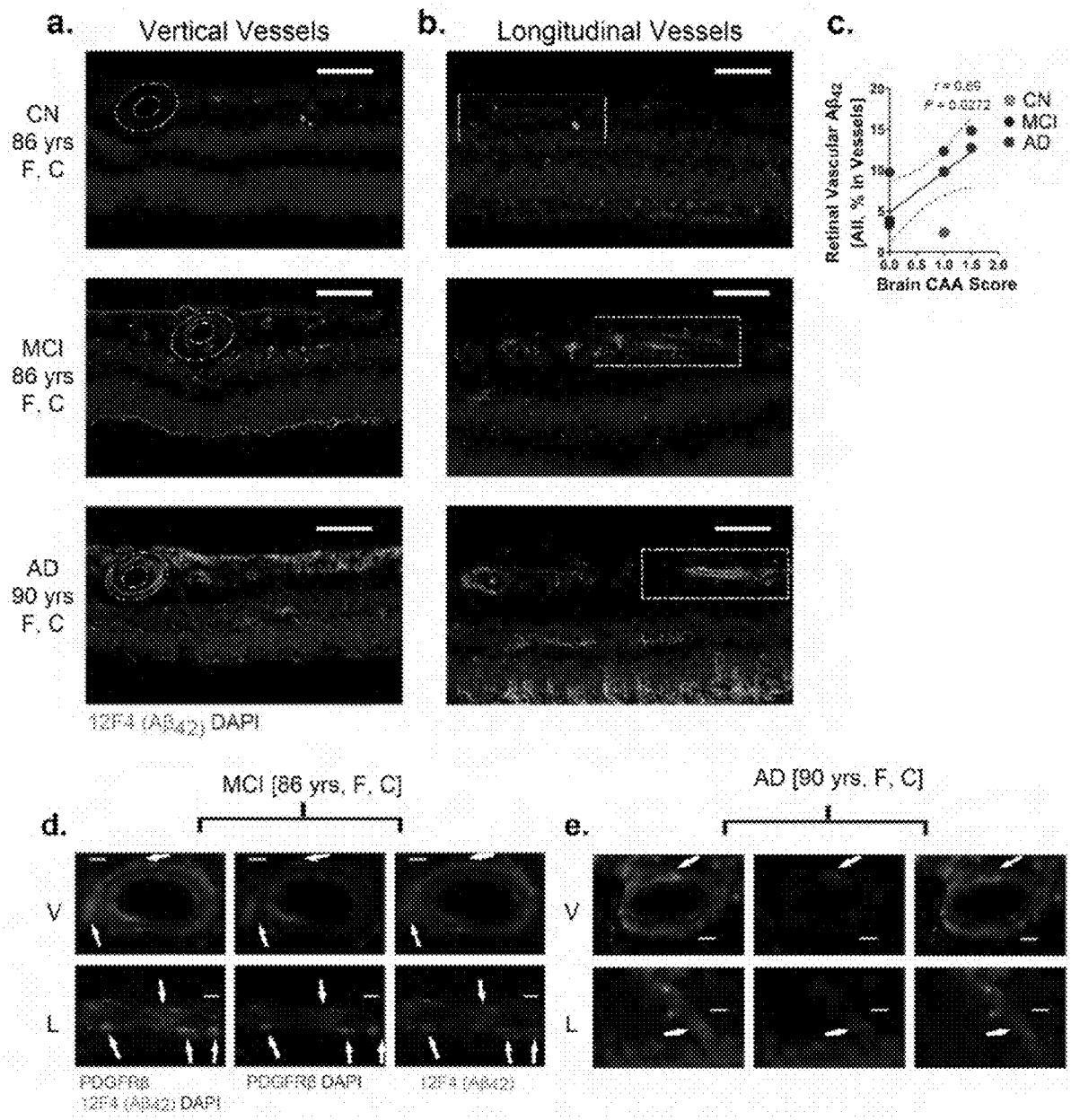
FIG. 12 (panels a-e) shows extended representative images for FIG. 3. a-b. Representative fluorescent images of paraffin-embedded retinal cross-sections isolated from age and sex-matched human donors with AD, MCI, or cognitively normal (CN) stained for Aβ 42 (12F4, green) and DAPI (nuclei, blue). a. Vertical (V) and b. longitudinal (L) blood vessels are shown. Dashed geometric shapes (white) indicate pre-defined areas of analysis. Scale bars=50 µm. c. Pearson's coefficient (r) correlation between retinal 12F4+ Aβ 42 burden in both V and L (All) blood vessels against brain CAA score. d-e. Merged and separate channels of representative fluorescent images for 12F4 (Aβ42, green), PDGFRβ (red) and DAPI (nuclei, blue) in paraffin embedded retinal cross-sections isolated from age and sex-matched human subjects with AD and MCI. Arrows point at Aβ 42 in PDGFRβ+cells. Both retinal V and L blood vessels in d. MCI and e. AD patients are shown (yrs=years old; F=female; C=Caucasian). Scale bars=10 µm.
Figure 13:
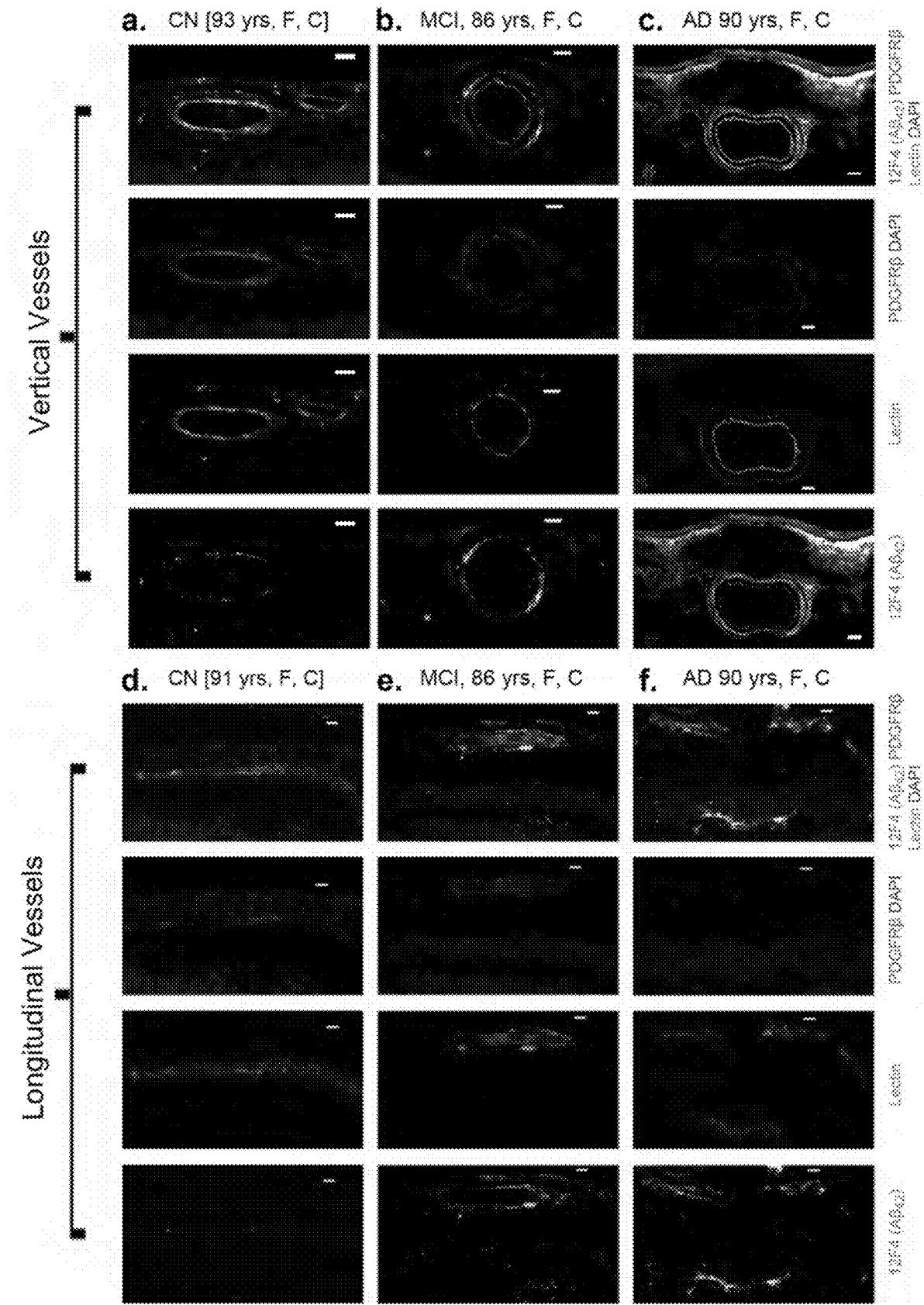
FIG. 13 (panels a-f) shows expanded representative images for Aβ 42, PDGFRβ, lectin and DAPI. a-f. Merged and separate channels of representative fluorescent images for 12F4 (Aβ42, white), PDGFRβ (red), lectin (glycoprotein in blood vessel, green) and DAPI (nuclei, blue) in paraffin-embedded retinal cross-sections isolated from age and sex-matched human donors with AD, MCI or cognitively normal (CN). a-c. Vertical and d-f. Longitudinal vessels are shown (yrs=years old; F-female; C=Caucasian). Scale bars=10 µm.

Next, investigation of the potential association between retinal vascular $A\beta_{42}$ burden and respective CAA scores suggested a significant correlation, albeit in a limited cohort (FIG. 12c). Additionally, retinal vascular $A\beta_{42}$ load had a significant correlation with cerebral Aβ plaque burden (FIG. 3e), and moreover, a strong, inverse correlation with retinal PDGFRβ(FIG. 3f). FIG. 3g demonstrates the gradual PDGFRβ loss concomitant with increased $A\beta_{42}$ burden in retinas isolated from MCI and AD patients relative to CN controls (for extended representative images see FIG. 13a-f). Higher magnification fluorescent images show $A\beta_{42}$ deposits inside residual retinal vascular PDGFRβ+ cells, with increased co-localization in MCI vs. AD (FIG. 3h; extended representative images in FIG. 12d-e). TEM analysis in retinal vertical sections from AD patients reveals $A\beta_{42}$ deposits in multiple locations near blood vessels and within pericytes (FIG. 3i-j). Retinal $A\beta_{42}$ deposits were found perivascular in close proximity to pericytes (FIG. 3i, left), in the lumen adjacent to an endothelial cell (FIG. 3i, right), and inside pericytes (FIG. 3j).

Substantial Accumulation of Vascular $A\beta_{40}$ in AD Retina

Figure 14:
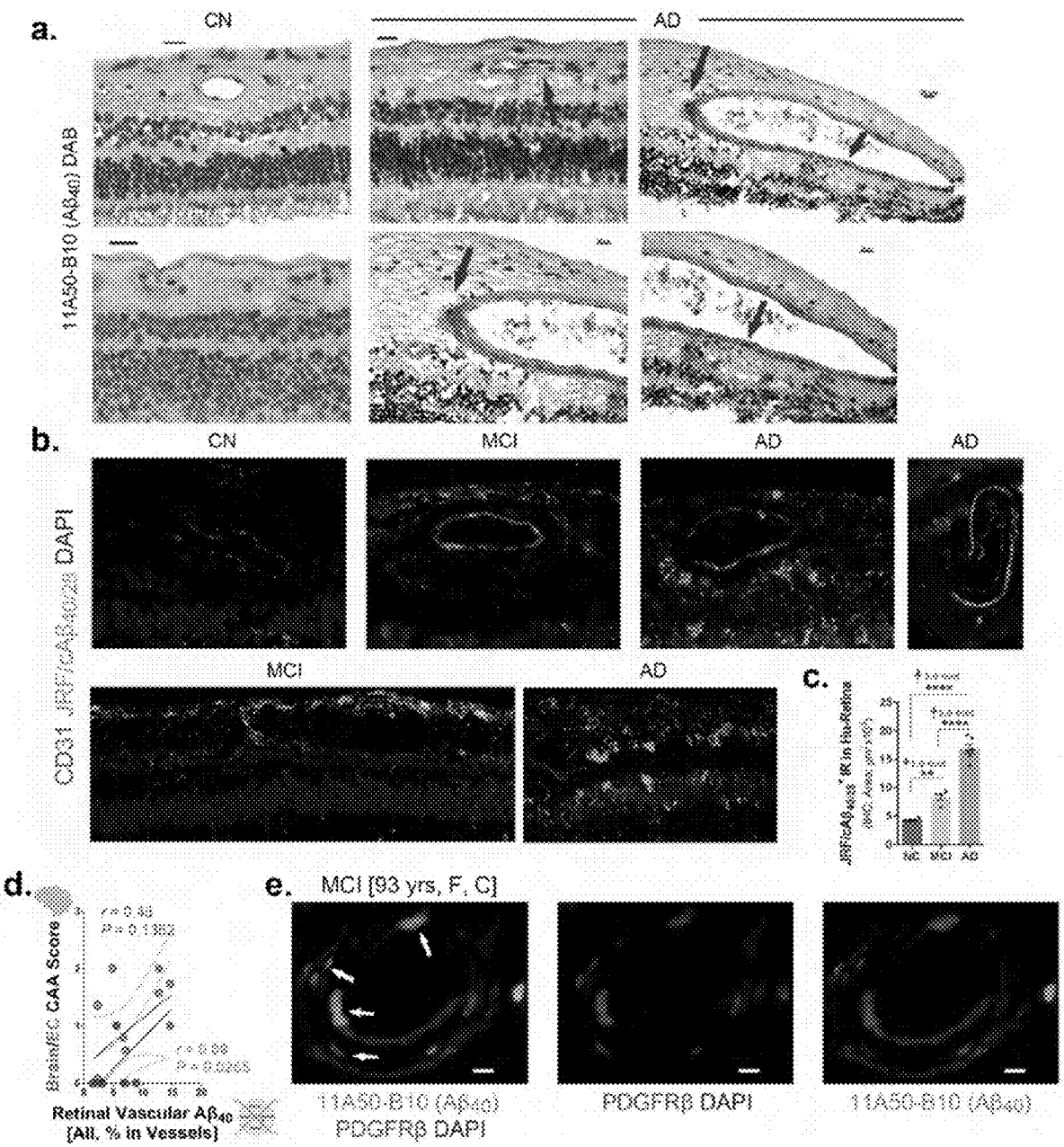
FIG. 14 (panels a-e) shows extended data on retinal vascular Aβ40 deposits from MCI and AD human donors compared to cognitively normal controls. a. Representative horseradish peroxidase and 3,3'-Diaminobenzidine (DAB) staining of images for 11A50-B10-Aβ40 in retinas from AD and cognitively normal (CN) subjects. Arrows indicate vascular Aβ40 staining in tunica intima and media. Scale bars=20 µm. b. Representative fluorescent microscope images of paraffin-embedded retinal cross-sections from AD, MCI and CN stained against Aβ40 (JRF/cAβ 40/28 antibody; green), endothelial cells (CD31; red) and nuclei (DAPI, blue). c. Quantitative analysis of retinal vascular Aβ40-IR area in a subset of MCI (n=4), AD (n=6) and CN (n=4) human donors. Data from individual human donors as well as group means and SEMs are shown. p<0.01, **p<0.0001, by one-way ANOVA test with Sidak's post-hoc multiple comparison test. Fold change are shown in red. d. Pearson's coefficient (r) correlation between retinal Aβ40 burden (11A50-B10-IR area) in both vertical and longitudinal vasculature (average) against CAA score in parenchymal brain average (grey) and entorhinal cortex (EC, red), within a subset of subjects with AD, MCI and CN (n=10). e. High-magnification images showing co-localization of vascular Aβ40 (green) and PDGFRβ (red; co-localization indicated by arrows) in a MCI subject (yrs=years old; F=female; C=Caucasian). Scale bars=10 µm.
Figure 15:
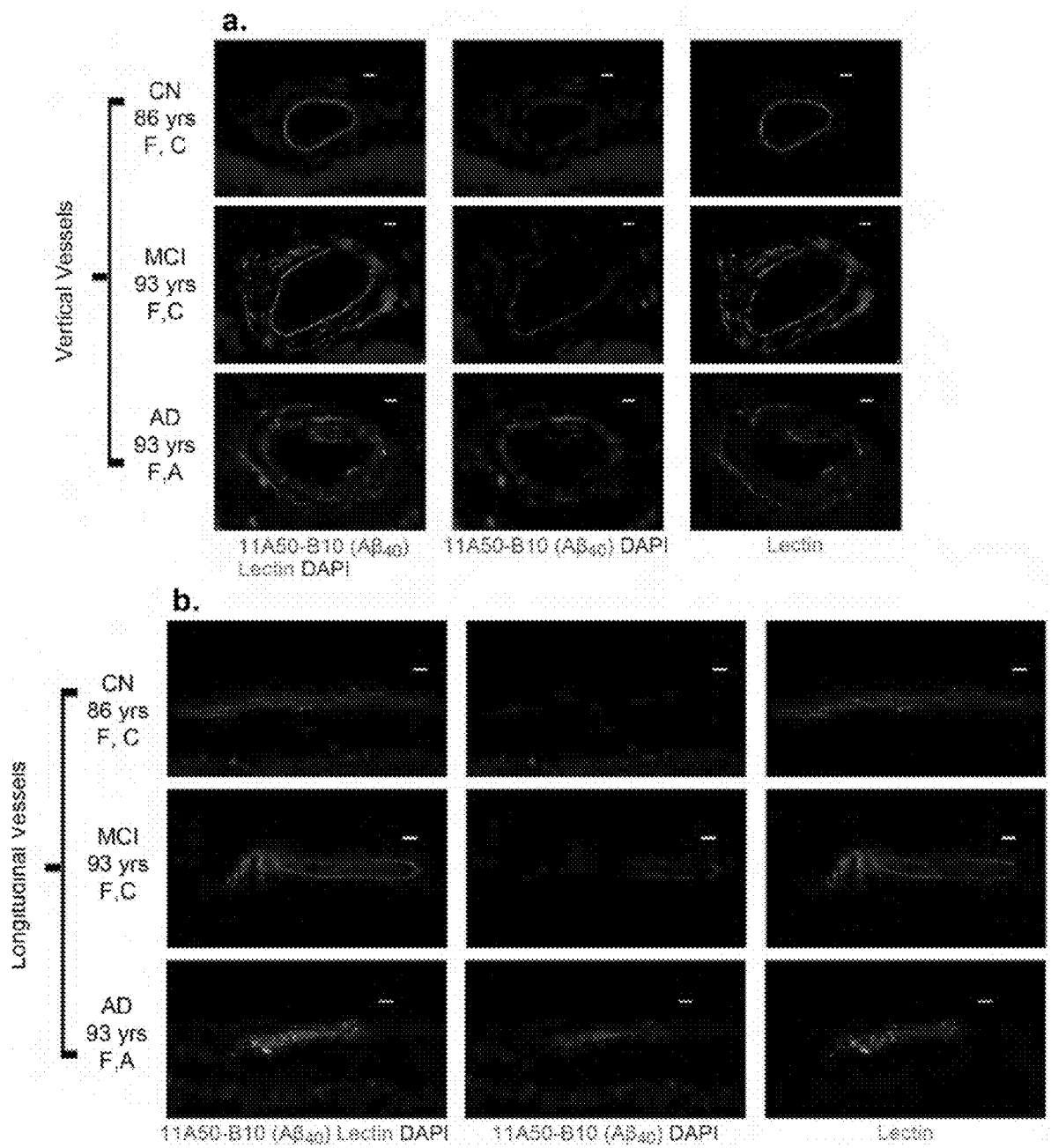
FIG. 15 (panels a-b) shows extended representative images for retinal Aβ 40. a-b. Merged and separate channels of representative fluorescent images for 11A50-B10 (Aβ40, red), lectin (glycoprotein in blood vessel, green) and DAPI (nuclei, blue) in paraffin-embedded retinal cross-sections isolated from age and sex-matched human donors with AD, MCI or cognitively normal (CN). a. Vertical and b. Longitudinal vessels are shown (yrs=years old; F=female; C=Caucasian; A=Asian). Scale bars=10 µm.

Since $A\beta_{40}$ is known to be the major alloform type deposited in cerebral blood vessels, we further studied its distribution in retinal blood vessels in a cohort of eye donors from age- and gender-matched individuals with diagnosis of AD, MCI, or CN (n=36, avg. age±SD: AD=81.8±14.8, MCI=86.3±6.2 and CN=78.1±10.4; see FIG. 4 and extended data in FIG. 14-15). Initial analysis of vascular $A\beta_{40}$ burden in paired retinas and brains utilizing peroxidase-based DAB staining with a specific antibody recognizing the C-terminal amino acid sequence of Aβ$_{40}$ (JRF/cAβ40/28; courtesy of Janssen Pharmaceutica) revealed an increase in retinal vascular Aβ$_{40}$ deposition in MCI and AD compared to CN controls (FIG. 4a-c). This was in agreement with our findings following application of a commercially available antibody (11A50-B10) recognizing the C-terminal sequence of human subjects based on clinical AD/MCI vs. CN diagnosis revealed a significantly lower PDGFRβ and significantly higher Aβ$_{40}$ and Aβ$_{42}$ levels in AD/MCI retinal vessels (FIG. 4m-o). These findings highlight the potential to distinguish between the diagnostic groups using retinal vascular parameters, and especially vascular PDGFRβ and Aβ$_{40}$ (FIG. 4n).

TABLE 7

Multiple correlation analysis between % retinal Aβ40 area in vessels and neuropathological parameters

|  |  | Neuritic Plaques | Immature Plaques | Diffuse Plaques | NFTs (Silver) | Neuropil Threads |
|---|---|---|---|---|---|---|
| All Brain | r | 0.55 | 0.44 | 0.16 | 0.24 | 0.58 |
|  | P | *0.0492* | 0.1292 | 0.6122 | 0.4278 | *0.0375* |
| Hippocampus | r | 0.41 | 0.22 | 0.08 | 0.37 | 0.48 |
|  | P | 0.1649 | 0.4702 | 0.7984 | 0.211 | 0.0967 |
| Entorhinal Cortex | r | 0.77 | 0.47 | 0.2 | 0.33 | 0.31 |
|  | P | *0.0023* | 0.1012 | 0.505 | 0.2755 | 0.3018 |
| Frontal Cortex | r | 0.05 | 0.53 | −0.06 | 0.40 | 0.53 |
|  | P | 0.8747 | 0.0638 | 0.8475 | 0.1777 | 0.0616 |
| Temporal Cortex | r | 0.00 | 0.23 | 0.02 | 0.06 | 0.57 |
|  | P | 0.9878 | 0.4551 | 0.9574 | 0.8534 | 0.0507 |
| Parietal Cortex | r | 0.02 | −0.09 | 0.15 | 0.14 | 0.38 |
|  | P | 0.941 | 0.7627 | 0.6274 | 0.6522 | 0.2022 |
| PV. Ctx. A-17 | r | 0.18 | 0.6 | 0.21 | −0.19 | 0.64 |
|  | P | 0.5929 | *0.0373* | 0.5179 | 0.5798 | *0.0347* |
| VA. Ctx. A-18 | r | 0.54 | 0.53 | −0.09 | −0.03 | 0.84 |
|  | P | 0.1377 | 0.1137 | 0.8081 | 0.93 | *0.0042* |

Correlations between retinal % area of Aβ40 in vessels and the corresponding neuropathological measurements: neuritic plaques, immature plaques, diffuse plaques, neurofibrillary tangles (NFTs; by Gallyas Silver stain), neuropil threads by sliver stain. Scores are given as: 0 = None, 1 = Sparse (–5), 3 = Moderate (6-20), 5 = Frequent (21-30 or above) based on pathological reports. Analysis was performed for mean of all brain regions and separated for each brain region. Sample size: n = 8 for AD, n = 3 for MCI, n = 1 for CN patients. Statistical significance P is < 0.05 indicated in bold. Pearson's r correlations analysis was applied to determine relationships; PV—primary visual; VA—visual association; Ctx—cortex.

Aβ$_{40}$ (FIG. 14a). Intriguingly, strong signal of Aβ$_{40}$ was observed in the tunica media (FIG. 4c and FIG. 14a), although deposits were also detected in tunica adventitia and intima (FIG. 4b-c and FIG. 14a, see arrows).

Immunofluorescent staining using 11A50-B10 and JRF/cAβ40/28 antibodies demonstrated an extensive retinal vascular Aβ$_{40}$ burden in both vertical and longitudinal vessels in AD (FIG. 4d-f; extended representative images in FIGS. 14b and 15a-b). Quantitative analysis of vascular 11A50-B10Aβ$_{40}$ immunoreactivity indicated substantial 7-12-fold increases in retinal vertical (vessel wall with lumen area excluded) and longitudinal vessels (representing both Aβ in circulating blood and vessel walls) in AD compared to CN (FIG. 4g-h). A non-significant trend was noted in MCI vs. CN controls and between MCI and AD groups. In an additional subset of human donors, analysis of retinal vascular Aβ$_{40}$ using JRF/cAβ40/28 antibody verified significant increases in retinas from MCI and AD compared to CN controls (n=14; FIG. 12c).

Figure 16:
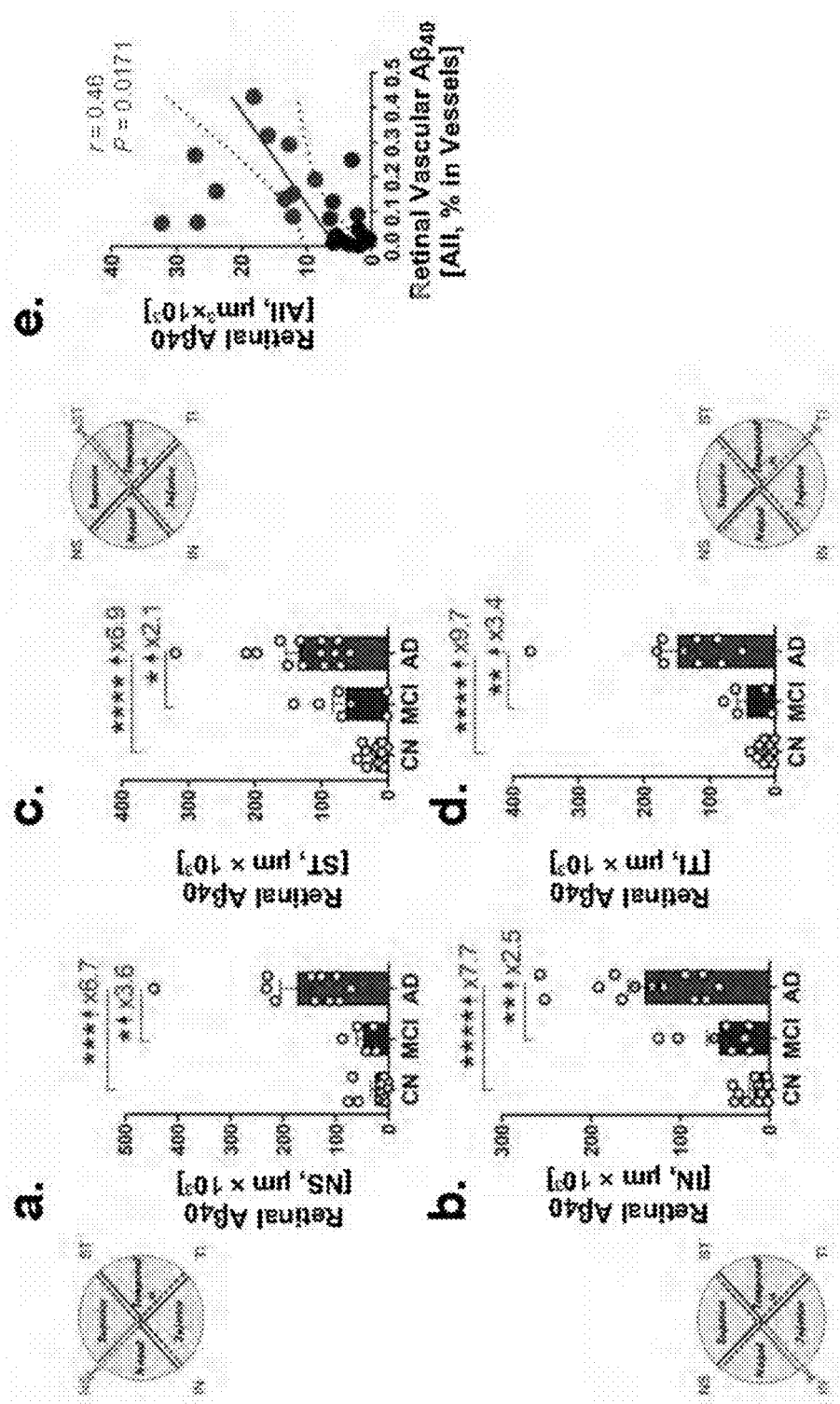
FIG. 16 (panels a-j) shows supplementary information for quantification of Aβ40 in human retina. a-d. Quantitative analysis of 11A50-810 (Aβ40) immunoreactive (IR) area (normalized by retinal thickness) in retinal layers (from inner to outer limiting membrane) from each retinal quadrant separately: a. NS, b. IN, c. ST, d. TI in AD (n=17). MCI (n=8), and CN (n=11) human donors. e. Pearson's coefficient (r) correlation between Aβ40 IR area and retinal Aβ40 burden in blood vessels (n=26). f-j. Quantitative analysis of raw data of 11A50-B10 (Aβ40)-IR area in retinal layers from each retinal quadrant separately and all quadrants together: f. all retinal quadrants, g. NS, h. IN, i. ST and j. TI in AD (n=17), MCI (n===8) and CN (n=11) human donors. *p<0.05, p<0.01, <0.001, **p<0.0001, by one-way ANOVA test with Sidak's post-hoc multiple comparison test. Fold changes are shown in red.
Figure 16:
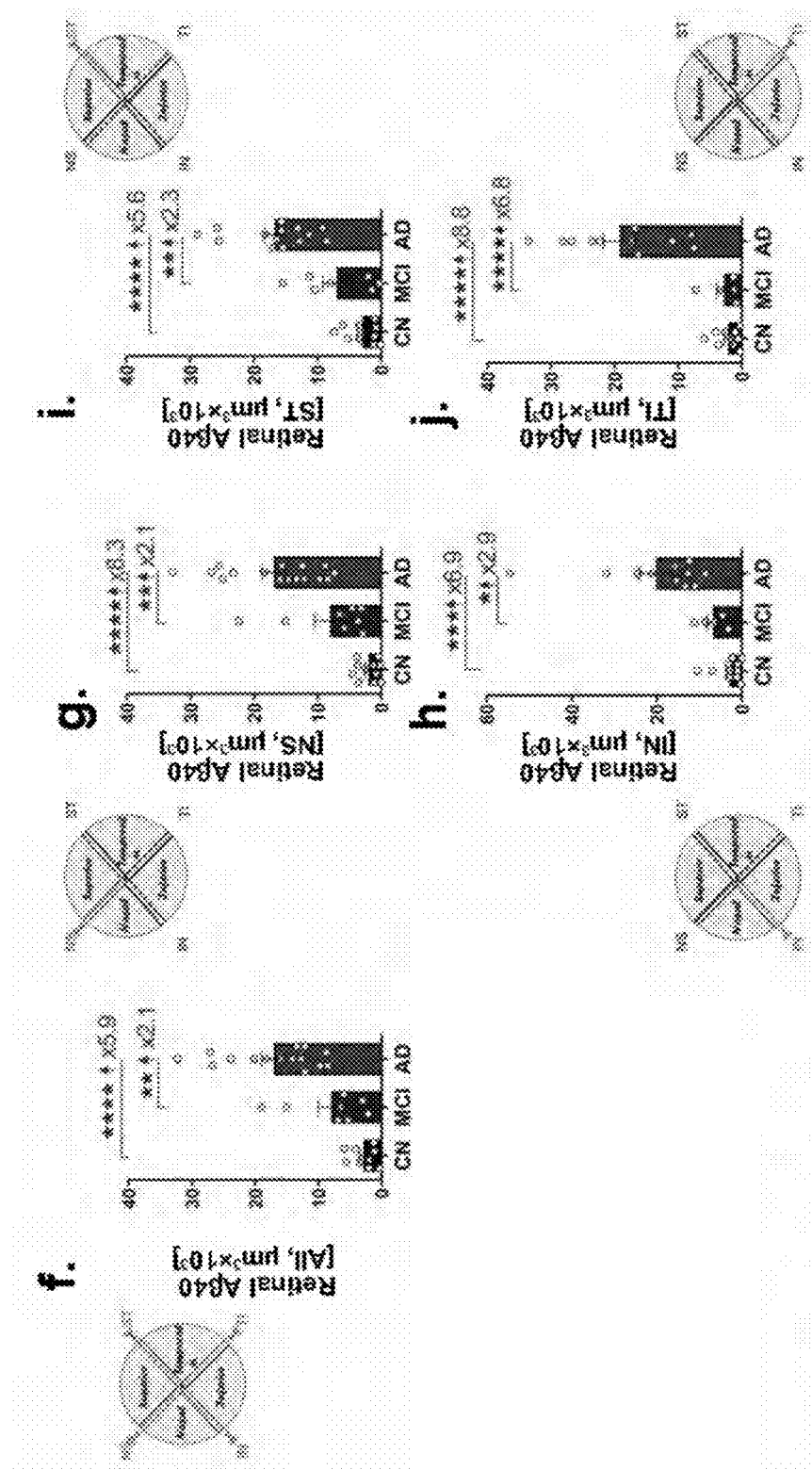

Similar to retinal vascular Aβ$_{42}$, retinal vascular Aβ$_{40}$ burden significantly and inversely correlated with retinal PDGFRβ (FIG. 4i), and also tightly and directly correlated with retinal vascular Aβ$_{42}$ burden (FIG. 4j). Moreover, retinal vascular Aβ$_{40}$ was associated with entorhinal cortex parenchymal CAA in a subset of human donors where CAA scores are available (FIG. 14d). Notably, increased retinal vascular Aβ$_{40}$ burden positively correlated with elevated brain NPs, especially in the entorhinal cortex (FIG. 4k-1; for more details see Table 7). The strongest correlation was observed with NTs in the visual association cortex (A-18). In addition, immature plaques in the primary visual cortex significantly associated with retinal vascular Aβ$_{40}$ (FIG. 4k-1; Table 7). Similar to vascular Aβ$_{42}$, vascular Aβ$_{40}$ was also detected in PDGFRβ$^+$ cells (FIG. 14e). Stratification of Mapping Retinal A/so Spatial and Layer Distribution in AD Shows High Burden in Inner Retinal Layers from Central Regions To evaluate the overall retinal Aβ$_{40}$ burden, including abluminal deposits outside blood vessels, we quantified Aβ$_{40}$ levels and mapped Aβ40-IR area in all four quadrants (ST, TI, IN, NS), central/mid/far (C/M/F) geometrical sub-regions, and inner vs. outer cellular layers of the neurosensory retina (FIG. 5). We initially measured retinal Aβ$_{1-40}$ peptide levels in protein homogenates isolated from fresh-frozen donor eyes in an additional cohort of age- and gender-matched subjects (n=11; 6 AD human eye donors: avg.±SD age=79.33±17.6 years, 4 females and 2 males, and 5 CN controls: avg. age 75.4±4.93 years, 3 females and 2 males). Quantitative ELISA revealed a significant increase in retinal Aβ$_{1-40}$ concentrations in AD compared to CN (FIG. 5a). Immunofluorescence staining in a larger cohort (n=36) using 11A50-B10 antibody confirmed a substantial elevation of retinal Aβ$_{40}$ load in AD compared to MCI and CN (FIG. 5b, data was normalized per retinal thickness; for raw data see FIG. 16f). Separate analyses of retinal Aβ$_{40}$ burden per quadrant indicated consistently higher Aβ$_{40}$ load in AD compared to MCI and CN, especially in TI quadrant (FIG. 16a-d, for normalized data per retinal thickness; FIG. 16g-j, for raw data). As expected, a significant positive correlation was noted between total Aβ$_{40}$ and vascular Aβ$_{40}$ in the human retina (FIG. 16e).

Our current observation of Aβ$_{40}$ distribution predominantly in the inner retina and in previous studies describing inner retinal pathology in AD, including thinning or RGC degeneration, prompt our analysis of Aβ$_{40}$ burden in inner vs. outer retinal layers. To this end, we separated the inner retina (from inner limiting membrane to inner nuclear layer) and the outer retina (from outer plexiform layer to outer limiting membrane), as illustrated in FIG. 5c. This analysis revealed that the vast majority of retinal Aβ$_{40}$ deposition (>90%) is found in the inner as compared to the outer layers across all diagnostic groups (FIG. 5d), with evidence for propagation to the outer retina (~5%) in AD (for extended data on Aβ$_{40}$ mapping in inner vs. outer retina with a separate analysis for each retinal quadrant see FIG. 17a-j). Further evaluation of Aβ$_{40}$ immunoreactivity in retinal C/M/F subregions indicated a significantly elevated burden in the central- vs. far-peripheral retina of AD, with similar but non-significant trends of increase in MCI (FIG. 5e; see comparative analysis of the four quadrants in FIG. 17k). A summary of retinal Aβ$_{40}$ burden analyzed in four quadrants, three geometrical subregions, and inner vs. outer layers is illustrated by a color-coded pie graph (FIG. 5f).

Figure 17:
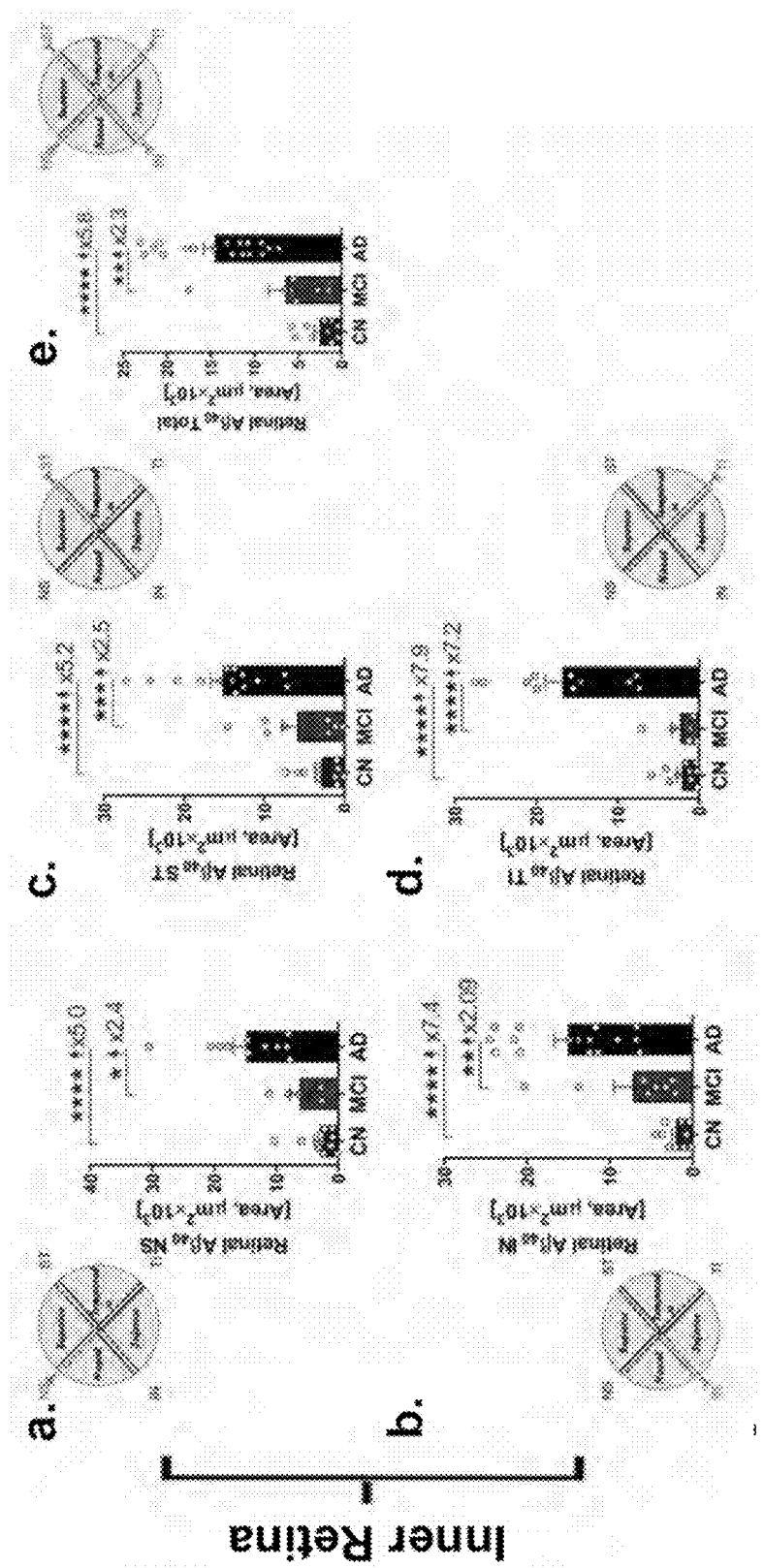
FIG. 17 (panels a-l) shows extended data of inner vs. outer retinal Aβ40 and mapping for all four retinal quadrants. a-e. Quantitative analysis of raw data of Aβ40-immunoreactive (IR) area in inner retinal layers from each retinal quadrant separately and all quadrants together: a. NS, b. IN, c. ST, d. TI, e. all, in AD (n=17), MCI (n=8) and CN (n=11) human donors. f-j. Quantitative analysis of raw data of Aβ40-IR area in outer retinal layers from each retinal quadrant separately and all quadrants together: f. NS, g. IN, h. ST, i. TI, j. all, in AD (n=17), MCI (n=8) and CN (n=11) human donors. k. Mapping of Aβ40 in four retinal quadrants (* indicates AD vs. CN, * indicates AD vs. MCI). l. Pearson's coefficient (r) correlation between Aβ40 IR area against % PDGFRβ-IR area in vessels (n=28). Data from individual human donor as well as group means and SEMs are shown. *p<0.05, p<0.01, *p<0.001, ****p<0.0001, by one-way or two-way ANOVA test with Sidak's post-hoc multiple comparison test. Fold changes are shown in red.
Figure 17:
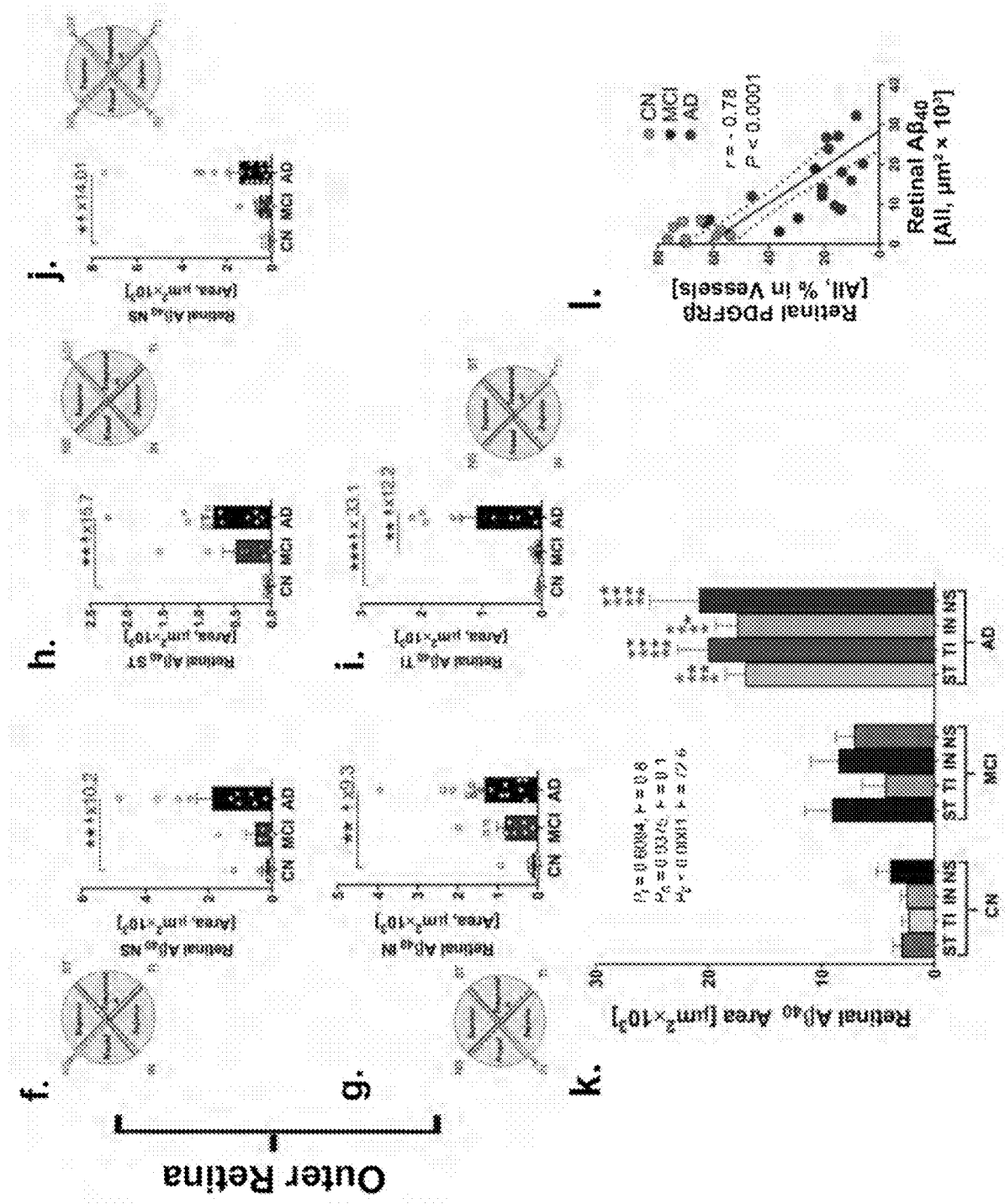

The feasibility to separate between the MCI/AD and CN clinical groups by total retinal Aβ$_{40}$ burden was further assessed. This analysis showed some overlap between the populations but indicated a significantly greater than 5-fold increase in the retina of AD/MCI vs. CN controls (FIG. 5g). Finally, to examine possible associations between total retinal Aβ$_{40}$ burden and other retinal and brain parameters, Pearson's (r) correlations were calculated (FIG. 5h-j; FIG. 17l). These analyses demonstrated a significant inverse correlation with retinal vascular PDGFRβ and non-significant correlations with brain NP (FIG. 5h), CAA scores (FIG. 5i), and cognitive status by MMSE (FIG. 5j; for correlations with different retinal quadrants see Table 8). Nonetheless, a significant association was detected between retinal Aβ$_{40}$ burden and NP in the entorhinal cortex (FIG. 5h).

To investigate whether the findings of retinal PDGFRβ and pericyte loss in MCI and AD are due to apoptotic cell death, we evaluated two markers of apoptotic cells in this cohort. First, we immunolabelled cleaved caspase-3 and investigated apoptosis of pericytes in small blood vessels (FIG. 6i-o). Representative microscopic images show a frequent occurrence of cleaved caspase-3$^+$ in pericyte nuclei in postmortem retinas from MCI and AD patients as compared to CN controls (FIG. 6j-1 vs. FIG. 6i; extended images for separate channels in FIG. 19a-d). Quantification of cleaved caspase-3$^+$ pericyte number confirmed an early retinal pericyte apoptosis in MCI, which was on average higher in AD (FIG. 6m). Cleaved caspase-3 in retinal pericytes inversely and strongly correlated with retinal PDGFRβ and positively with retinal Aβ$_{40}$ burden (FIG. 6n-o). To further validate apoptosis of retinal pericytes during AD progression, fluorescent TUNEL assay was utilized on the same cohort (representative microscopic images in FIG. 6p-t; extended images for separate channels in FIG. 20a-d). Analysis of TUNEL$^+$ pericyte count indicated increased apoptosis of retinal pericytes in MCI and more significantly in AD (FIG. 6u), and a significant inverse correlation with retinal PDGFRβ (FIG. 6v).

Example 2

Materials and Methods

Mice

Double-transgenic B6.Cg-Tg (APP$_{SWE}$/PS1$_{ΔE9}$)85Dbo/Mmjax hemizygous (ADtg) mice (MMRRC stock #34832-

TABLE 8

Correlation between Aβ40 burden per retinal subregions and MMSE cognitive scores.

| Retinal Regions | Total | ST | TI | IN | NS | Superior | Inferior | Nasal | Temporal |
|---|---|---|---|---|---|---|---|---|---|
| r | −0.57 | −0.71 | N/A | −0.65 | N/A | −0.73 | −0.67 | −0.66 | −0.75 |
| P | 0.0827 | 0.0737 | N/A | 0.1107 | N/A | 0.0625 | 0.099 | 0.1062 | 0.0539 |
| n | 10 | 7 | N/A | 7 | N/A | 7 | 7 | 7 | 7 |

Total; total retinal average; ST, superiortemporal; TI, temporalinferior; IN, inferioimasal; NS, nasalsuperior; Superior, mean of ST and NS values; Inferior, mean of TI and IN values; Nasal, mean of IN and NS values; Temporal, mean of ST and TI values. N, number of pairs. N/A, not applicable. Statistical significance P is <0.05. Pearson's r correlations analysis was applied to deteimine relationships.

Figure 18:
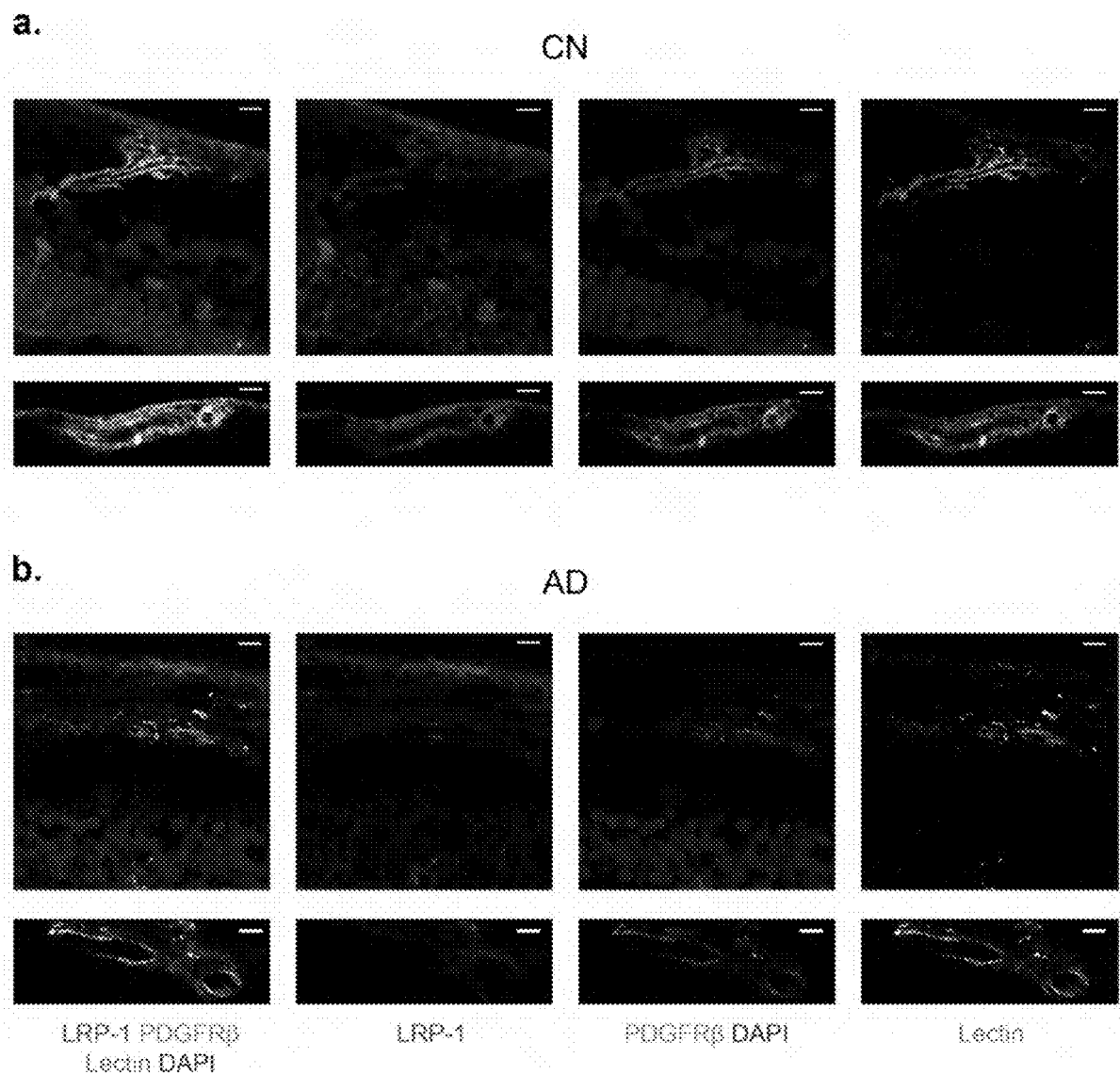
FIG. 18 (panels a-b) shows extended representative images for LRP-1 in FIG. 6. a-b. Merged and separate channels of representative fluorescent images for LRP-1 (red), PDGFRβ (green), lectin (glycoprotein in blood vessel, white) and DAPI (nuclei, blue) in paraffin-embedded retinal cross-sections isolated from age and sex-matched human donors with AD or cognitively normal (CN). a. CN and b. AD are shown. Scale bars=10 μm.
Figure 19:
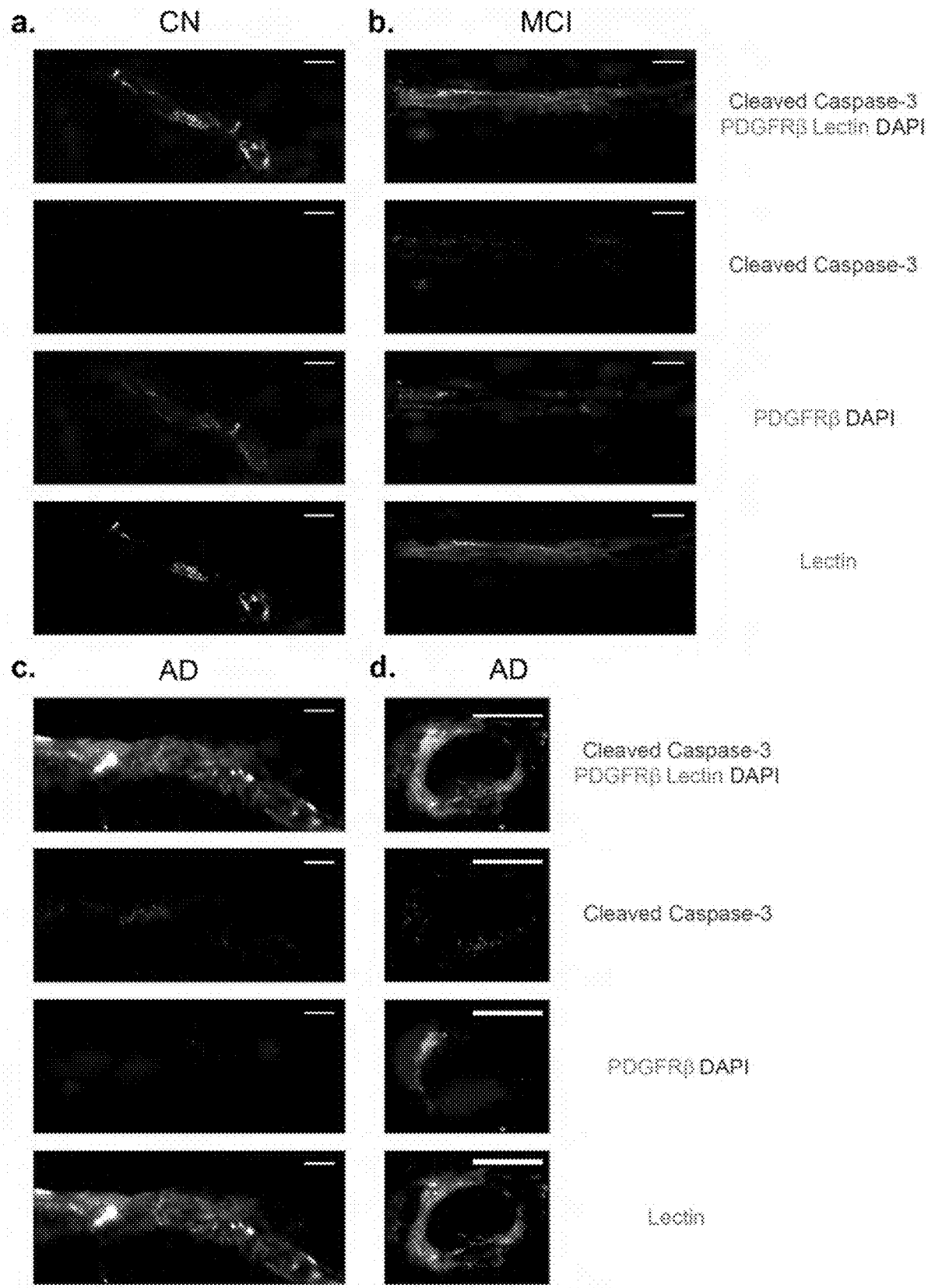
FIG. 19 (panels a-d) shows extended representative images for cleaved caspase-3 in FIG. 6. a-d. Merged and separate channels of fluorescent images for cleaved caspase-3 (red), PDGFRβ (green), lectin (glycoprotein in blood vessel, white) and DAPI (nuclei, blue) in paraffin-embedded retinal cross-sections isolated from age and sex-matched human donors with AD, MCI or cognitively normal (CN). a. CN, b. MCI and c-d. AD are shown. Scale bars=10 μm.
Figure 20:
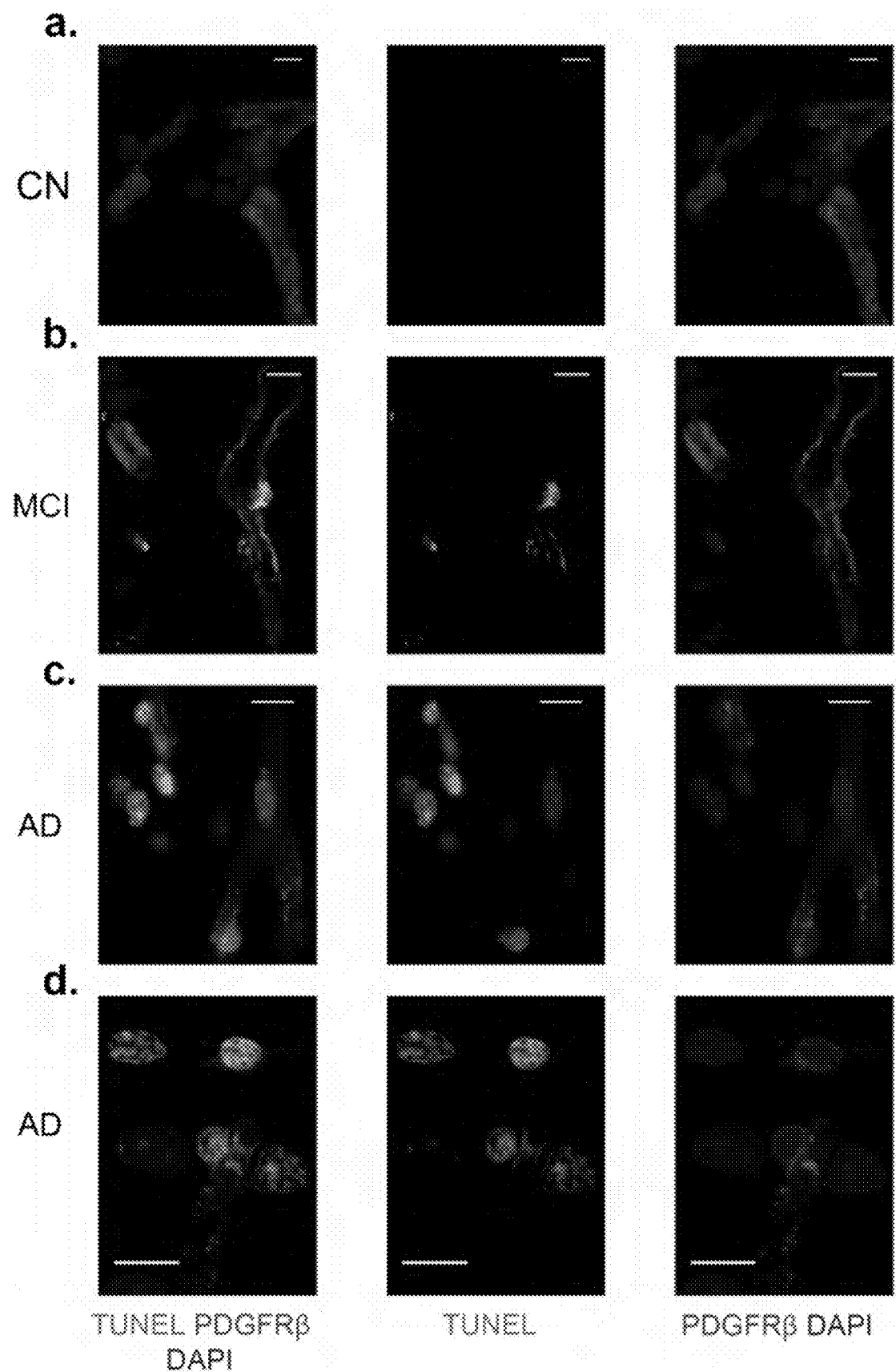
FIG. 20 (panels a-d) shows extended representative images for TUNEL staining in FIG. 6. a-d. Merged and separate channels of fluorescent images for TUNEL (green), PDGFRβ (red), and DAPI (nuclei, blue) in paraffin-embedded retinal cross-sections isolated from age and sex-matched human donors with AD, MCI or cognitively normal (CN). a. CN, b. MCI and c-d. AD are shown. Scale bars=10 μm.

Vascular LRP-1 Downregulation in AD Retina and Retinal Pericyte Apoptosis in MCI and AD In murine models of AD, vascular LRP-1 was shown to be expressed by pericytes, mediate the clearance of brain-parenchymal Aβ via blood vessels, and affect cerebral amyloid deposition. To evaluate LRP-1 and vascular LRP-1 expression in the human retina, we analyzed retinal cross-sections from a cohort of eighteen subjects with AD, MCI, and CN (n=6 subjects per each diagnostic group). Representative microscopic images demonstrated reduced vascular LRP-1 expression along with marked vascular PDGFRβ loss in postmortem retinas from an AD as compared with CN control (FIG. 6a-d; extended images for separate channels in FIG. 18a-b). A quantitative IHC analysis indicated a non-significant trend of decreased total retinal LRP-1 immunoreactivity in AD compared to CN controls (FIG. 6e), with no difference between levels of LRP-1 in MCI vs. CN controls. Evaluation of vascular LRP-1 expression revealed a significant 32% decrease in AD compared to CN (FIG. 6f). Retinal vascular LRP-1 significantly correlated with retinal vascular PDGFRβ in this cohort (FIG. 6g), yet showed a non-significant trend of association with retinal Aβ$_{40}$ burden (FIG. 6h).

JAX|APP/PS1) and their non-tg littermates (WT control non-AD groups) were used for this experiment. All mice had the genetic background of B6. The animals were purchased from MMRRC and later bred and maintained at Cedars-Sinai Medical Center. The mouse experiments were conducted in accordance with Cedars-Sinai Medical Center Institutional Animal Care and Use Committee (IACUC) guidelines under an approved protocol. The first cohort of 51 mice, age- and sex-matched, were divided into several groups: 4-month-old perfused WT (n=8), 4-month-old perfused ADtg (n=8), 8-month-old perfused WT (n=8), 8-month-old perfused ADtg (n=8), 8-month-old non-perfused ADtg (n=3), 12-month-old perfused WT (n=8), and 12-month-old perfused ADtg (n=8). The animals were deeply anesthetized with ketamine/xylazine (40-50 mg/kg) before being euthanized by either transcardial perfusion (0.9% ice-cold sodium chloride supplemented with 0.5 mM EDTA) or cervical dislocation (non-perfused group). The animals' eyes were dissected, and the retinas immediately isolated as previously described. Following isolation, the retinas were processed differently for various purposes. For vascular isolation, retinas were fixed in 4% paraformaldehyde (PFA) solution for 7 days before proceeding to isolation and staining; for protein isolation, retinas were immediately sonicated in RIPA lysis buffer (Thermofisher Scientific, #89900) with proteinase inhibitor and phosphatase inhibitor (Thermofisher Scientific, #78440); for retinal cross-section, whole eyes were fixed in 4% PFA for 30 minutes in PBS, then transferred to 4% PFA containing 30% sucrose for cryoprotection at 4° C.

A second cohort of mice (n=10; average age of 6 months old) was used to assess BBB permeability by tracer infusion: 5 WT and 5 ADtg age- and sex-matched mice received 50 µL of Texas Red-dextran 3 kD (0.25%) and fluorescein isothiocyanate (FITC)-dextran 2000 kD (0.25%) via tail vein before being euthanized by perfusion 30 min later (procedure and tissue collection as described above). Retinas were isolated immediately after mice were euthanized, and then were mounted to microscopic slides with ProLong Gold antifade reagent with 4',6-diamidino-2-phenylindole (DAPI; Invitrogen #P36935). For purposes of quantification, images were obtained using an Axio Imager Z1 fluorescence microscope (Carl Zeiss MicroImaging, Inc.) equipped with ApoTome, AxioCam MRm, and AxioCam HRc cameras (for more details see Stereological quantification below).

Another set of mice (n=8; at the age of 8, 12 and 16 months) underwent non-invasive retinal imaging after intra peritoneal (IP) injection of Fluorescein (2%; 15 µl; Ak-Fluor #17478-253-10) to assess retinal microvascular leakage. Representative live images were taken during ten to thirty minutes post-injection.

Retinal Vascular Isolation and Immunofluorescence Staining

The trypsin-induced retinal digestion and vascular network isolation technique was originally developed in 1993 and subsequently modified by replacing trypsin with commercially available elastase. Briefly, retinal strips fixed in PFA were first washed in running distilled water overnight, then digested in 40 U/mL elastase solution (Merck Millipore, #324682) for 2 hours at 37° C. After initial digestion, the tissues were incubated in activation solution (Tris buffer at pH 8.5) overnight for extensive digestion. The next day, the retinas were transferred to Superfrost microscope slides with 1×PBS, then carefully cleaned with a rat whisker tool under a dissecting microscope to remove unwanted tissue. After the nonvascular tissues had been cleaned, 1×PBS was applied three times to wash the isolated vascular tissues. Samples of isolated retinal vasculature were then mounted differently for immunofluorescence staining or periodic acid-Schiff (PAS) and hematoxylin staining. For immunofluorescence staining, the tissues were mounted on slides carefully without prior dehydration, then incubated in blocking buffer (Dako #X0909) for 1 hour at room temperature (RT). Tissues were then incubated overnight at 4° C. with the following primary antibody combinations: 4G8/lectin/PDGFRβ and 11A50-B10/lectin/PDGFRβ; for a complete list of primary and secondary antibodies as well as other labeling compounds used in this study see Table 9. Tissues were then washed three times with PBS and incubated with secondary antibodies for 2 hours at RT. Tissues were further washed with PBS three times, and then vascular trees were mounted using ProLong Gold antifade reagent with DAPI (Invitrogen #P36935). For quantification, images were obtained using an Axio Imager Z1 fluorescence microscope (Carl Zeiss MicroImaging, Inc.) equipped with ApoTome, AxioCam MRm, and AxioCam HRc cameras (for more details see Stereological quantification below). For representative images, Z-stack images were repeatedly captured at the same tissue thickness by using a Carl Zeiss 780 confocal microscope (Carl Zeiss MicroImaging, Inc.) or a Leica SP 5 WLL confocal microscope (Leica Microsystems). Routine controls were processed using identical protocols while omitting the primary antibody to assess non-specific labeling.

TABLE 9

List of antibodies and reagents for imaging

| Antibodies or Reagents | Source Species | Dilution | Application | Commercial Source | Catalog. # |
| --- | --- | --- | --- | --- | --- |
| Primary antibody | | | | | |
| PDGFRβ pAb | Goat | 1:200 | IF | R&D Systems | AF385 |
| 4G8 mAb | Mouse | 1:200 | IF | Biolegend | 800701 |
| Alexa Fluor 488-conjugated tomato lectin | *Lycopersicon esculentum* | 1:200 | IF | Dylight | DL-1174 |
| Aβ$_{40}$ (11A50-B10) mAb | Mouse | 1:200 | IF | Biolegend | 805401 |
| CD31 pAb | Rabbit | 1:100 | IF | Abcam | ab28364 |
| Zonula Occluden-1 pAb | Rabbit | 1:50 | WB | Thermofisher | 61-7300 |
| Claudin-1 pAb | Rabbit | 1:75 | WB | Thermofisher | 51-9000 |
| phospho-NF-κB p65 Ser536 mAb | Rabbit | 1:1000 | WB | Cell Signaling Technology | 3033S |
| NF-κB p65 mAb | Rabbit | 1:1000 | WB | Cell Signaling Technology | 8242S |
| β-actin | mouse | 1:1000 | WB | Santa-Cruz Biotechnology | Sc-47778 |
| Secondary antibody | | | | | |
| Cy3 (anti-rabbit, anti-goat) | Donkey | 1:200 | IF | Jackson ImmunoResearch Laboratories | |
| Cy5 (anti-mouse, anti-rabbit) | Donkey | 1:200 | IF | Jackson ImmunoResearch Laboratories | |
| Peroxidase Goat Anti-Rabbit IgG (H + L) | Goat | 1:10000 | WB | Jackson ImmunoResearch Laboratories | |
| Peroxidase Goat Anti-Mouse IgG (H + L) | Goat | 1:10000 | WB | Jackson ImmunoResearch Laboratories | |

TABLE 9-continued

List of antibodies and reagents for imaging

| Antibodies or Reagents | Source Species | Dilution | Application | Commercial Source | Catalog. # |
|---|---|---|---|---|---|
| In vivo retinal live imaging | | | | | |
| Fluorescein (322.31 Da) | N/A | 2% | IVRLI | Dailymed | 17478-250-20 |
| Ex vivo retinal imaging | | | | | |
| FITC-dextran (2000 kD) | N/A | 0.25% | EVRI | Sigma Aldrich | FD2000s-5G |
| Texas Red-dextran (3 kD) | N/A | 0.25% | EVRI | Thermofisher | D1829 |
| Thioflavin-S | N/A | 1% | IF | Sigma-Aldrich | T1892 |
| Degenerated capillary quantification (PAS) | | | | | |
| Periodic Acid | N/A | 35 mM | DCQ | Milliporesigma | P7875 |
| Schiff | N/A | 100% | DCQ | Sigma Aldrich | 3952016 |

IF—immunofluorescence; WB—western blot; pAb—polyclonal antibody; mAb—monoclonal antibody; IVRLI—in vivo retinal live imaging; EVRI—ex vivo retinal imaging; DCQ—degenerated capillary quantification; N/A—not applicable; If not marked otherwise, antibody dilution is indicated for immunofluorescent essay.

Periodic Acid Schiff Staining of Isolated Retinal Microvasculature

For PAS staining, samples of isolated retinal microvasculature were mounted differently after elastase digestion and clearing. Specifically, the isolated retinal microvasculature was dried overnight after being mounted on glass Superfrost Plus microscope slides (Fisher Scientific, #12-550-15). On the following day, the samples were first rehydrated in distilled water for 15 minutes. The rehydrated samples were then incubated with periodic acid (MilliporeSigma, #P7875) solution at a concentration of 35 mM at RT for 8 minutes, followed by a brief dipping in distilled water. Afterward, the tissues were stained with Schiff (Sigma-Aldrich, #3952016) for 15 minutes, followed by three separate extensive washes in running distilled water lasting 5 minutes each time. The tissues were then stained with hematoxylin (Richard-Allan Scientific, #7231) for 2 minutes, followed by three 5-minute distilled water washes. After staining, the slides were dehydrated in 70%, 85%, 90%, and 100% ethanol, and finally xylene, 2 minutes for each reagent. Following this, the slides were mounted with Permount mounting medium (Fisher Scientific, #SP15-100). For purposes of quantification, the images were obtained using an Axio Imager Z1 fluorescence microscope (Carl Zeiss MicroImaging, Inc.) equipped with ApoTome, AxioCam MRm, and AxioCam HRc cameras (for more details see Stereological quantification below).

Retinal Cross-Section, Fluorescence and Immunofluorescent Staining

Eyes preserved in 4% PFA with 30% sucrose were first embedded in OCT compounds on dry ice. Then the retinal cross-sections (10 mm thick) were cut using a cryostat machine (Leica Biosystems) and stored at −80° C. until use. For immunostaining, retinal cross-sections were incubated in blocking buffer (Dako #X0909) for one hour at RT, followed by incubation with primary antibodies of rabbit anti-mouse CD31 (1:100; Abcam) and mouse anti-human 11A50-B10 (1:200, Biolegend). Sections were then washed three times in PBS and incubated with secondary antibodies (see Table 9 for details) for two hours at RT. The sections were then briefly washed twice in PBS for five minutes, then incubated in thioflavin-S (1%, Sigma-Aldrich) for 10 minutes at RT. Finally, sections were washed with 70% ethanol three times followed by PBS, and then mounted using ProLong Glass antifade reagent (Invitrogen #P36980).

Images were obtained using an Axio Imager Z1 fluorescence microscope (Carl Zeiss MicroImaging, Inc.) equipped with ApoTome, AxioCam MRm, and AxioCam HRc cameras. Routine controls included staining of non-Tg mouse retina and ADtg mouse sections that were processed using identical protocols while omitting the primary antibody to assess nonspecific labeling.

Protein Extraction and Western Blot Analysis

Sonicated retinal lysates in RIPA buffer were first centrifuged at 13600 rpm at 4° C. Afterward, the supernatant was transferred to fresh new tubes. Protein concentration was determined by using the BCA kit (Thermofisher, #23227) and following the standard protocol. Equal amounts of total proteins were then separated onto 4% to 20% Tris-glycine gels (Invitrogen, #XP04205BOX) and transferred to nitrocellulose membranes. Then, after blocking the membranes in TBST (10 mmol/L Tris-HCl buffer, pH 8.0, 150 mmol/L NaCl, and 0.1% Tween 20) with 5% (w/v) bovine serum albumin (BSA) at RT for 60 minutes, the membranes were incubated overnight at 4° C. with antigen-specific primary antibodies. The following primary antibodies were used: anti-ZO-1 (1:50; Thermofisher, #61-7300), anti-claudin-1 (1:75; Thermofisher, #51-9000), anti-phospho-NF-κB p65 Ser536 (1:1000, Cell Signaling Technology, #3033S), anti-NF-κB p65 (1:1000, Cell Signaling Technology, #8242S), and anti-R-actin (1:1000; Santa Cruz Biotechnology, #sc-47778). The blots were then incubated with species-specific horseradish peroxidase-conjugated secondary antibodies for 2 hours at RT. Proteins were visualized by incubation with a chemiluminescence substrate kit (Thermofisher, #34580). Western blot images were collected (iBright imaging system; Thermofisher), and the targeted protein expression was quantified using Image Studio Lite software version 5.2 (LI-COR Biosciences, Lincoln, NE) after normalizing to R-actin. One representative blot is shown for each molecule.

Stereological Quantification

Degenerate capillaries were identified as acellular capillary-sized tubes and were manually counted in an average of eight microscopic fields (covering $1.8 \times 10^4$-$\mu m^2$ area) per retina (see FIG. 1). Degenerate capillaries were excluded if their average diameter was <20% the size of surrounding healthy capillaries.

Figure 22:
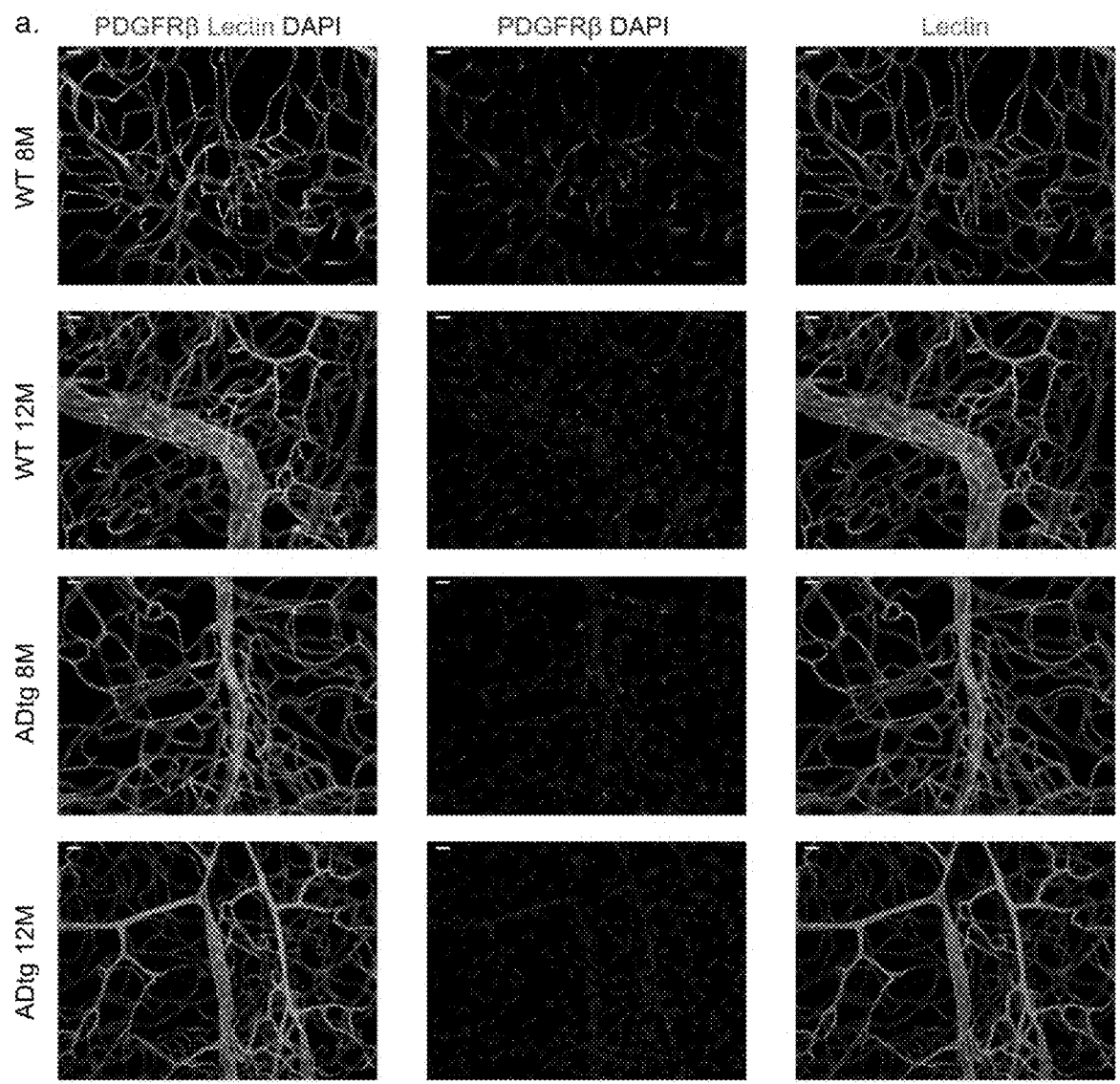
FIG. 22 (panels a-e) shows retinal vascular PDGFRβ deficiency in $APP_{SWE}/PS1_{\Delta E9}$ (ADtg) mice. A subset of the mouse cohort described in FIG. 1 of age- and sex-matched ADtg and wild type (WT) mice were analyzed at the age of 8 (n=6; ADtg=3 and WT=3) and 12 (n=6; ADtg=3 and WT=3) months. a. Representative fluorescence images of isolated retinal microvasculature stained for pericytes (PDGFRβ, red), blood vessels (lectin, green), and nuclei (DAPI, blue) in ADtg and WT littermates. Scale bars=20 μm. b. A quantitative analysis of ratio between PDGFRβ-immunoreactive (IR) area and lectin-IR area in each microscopic field of isolated retinal microvasculature when mice are stratified by genotype of ADtg and WT. c-d. Ratio of PDGFRβ-IR area to lectin-IR area in each microscopic field in the same mouse cohort when mice are stratified by genotypes of WT vs. ADtg and c. age of mice by 8 month and 12 month or d. sex of mice. e. Pearson's coefficient (r) correlation between retinal PDGFR-IR area and degenerated capillary count in the same mice cohort (n=12). Data from individual mice (circles) as well as group means±SEMs are shown. Black-filled circles represent males and clear circles represent females; blue-filled circles represent WT mice and pink-filled circles represent ADtg mice. Percentage decreases are shown in red. *p<0.05, p<0.01, *p<0.001, by two-way ANOVA with Tukey's post-hoc multiple comparison test. Two group statistical analysis was performed using an unpaired 2-tailed Student t-test. P and F values of two-way ANOVA refer to comparisons of age groups ($P_A$, $F_A$), ADtg vs WT genotype groups ($P_G$, $F_G$), gender groups ($P_{Ge}$, $F_{Ge}$), and overall interactions ($P_1$, $F_1$).
Figure 22:
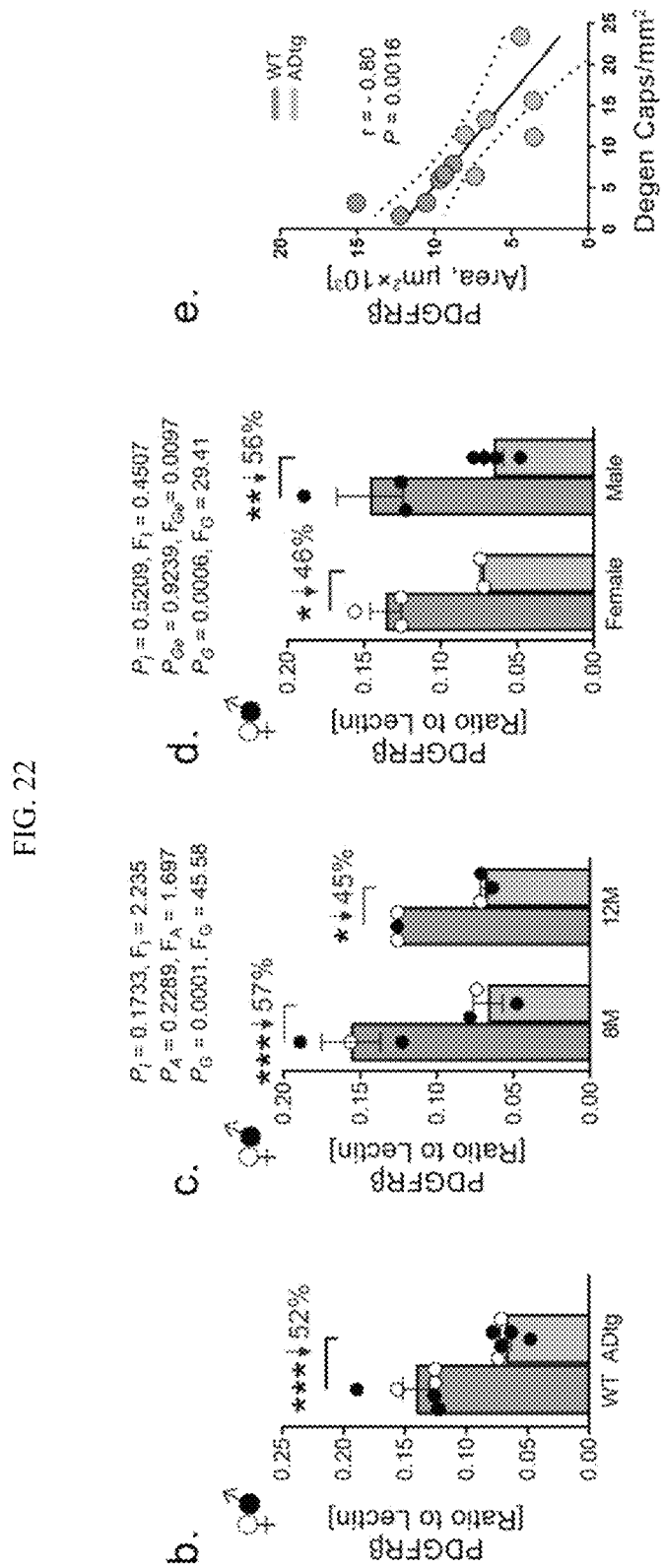
Figure 23:
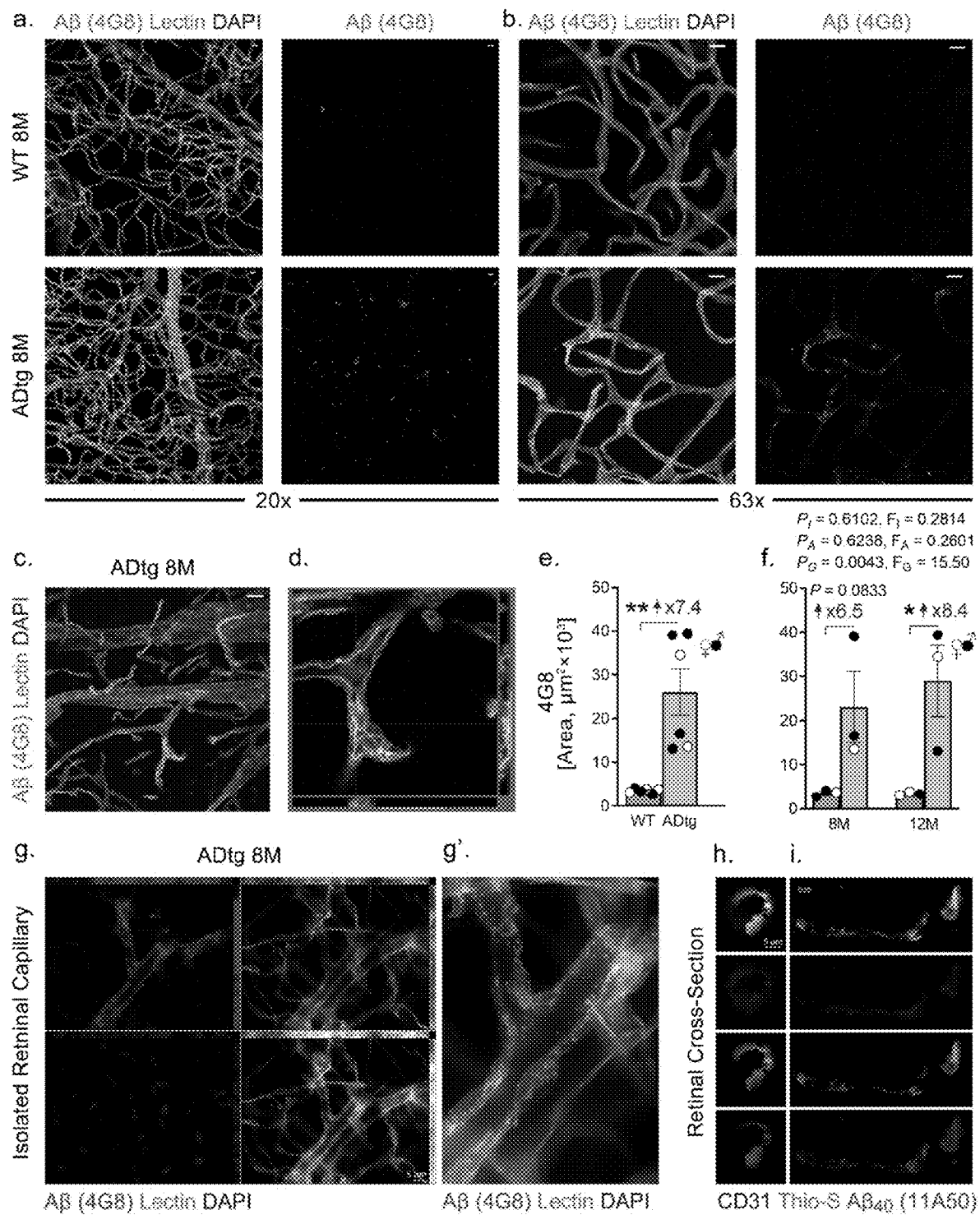
FIG. 23 (panels a-i) shows retinal amyloidosis in blood vessel walls of $APP_{SWE}/PS1_{\Delta E9}$ (ADtg) mice. a-b. Representative fluorescence images acquired using a. 20× or b. 63× microscope objectives, of isolated retinal microvasculature stained for Aβ (4G8, magenta), blood vessels (lectin, green), and nuclei (DAPI, blue) in age- and sex-matched perfused ADtg mice (n=6) and wild-type littermates (WT; n=6). Scale bars=20 μm. c-d. Representative fluorescence virtual cross-section images acquired using the Leica confocal microscope 63× objective of the isolated retinal microvasculature stained for Aβ (4G8, magenta), blood vessels (lectin, green) and nuclei (DAPI, blue) in an 8-month-old male ADtg mouse. Scale bar=20 μm. Arrows indicate vascular Aβ. e. Quantitative analysis of Aβ (4G8)-immunoreactive (IR) area in each microscopic field of isolated retinal microvasculature from WT vs. ADtg mice. f. Quantitative analysis of the Aβ (4G8)-IR area stratified by mice age group (8 months vs. 12 months) and genotype (WT vs. ADtg) in the same cohort. g-g'. Representative fluorescence images of the isolated retinal microvasculature stained for Aβ (4G8, red), blood vessels (lectin, green) and nuclei (DAPI, blue) in an 8-month-old male ADtg mouse; Aβ signals occur in retinal vessel walls and vascular cells. h-i. Representative fluorescence images of fixed retinal cross-section stained for thioflavin-S (Thio-S, green), $Aβ_{40}$ (11A50-B10, red) and blood vessels (CD31, blue) in an 8-month-old male ADtg mouse showing h. vertical blood vessel and i. longitudinal blood vessel. Data from individual mice (circles) as well as group means±SEMs are shown. Black-filled circles represent males and clear circles represent females. Fold changes are shown in red. *p<0.05.

For FIGS. 22 and 23, which display isolated retinal blood vessels, quantification was performed using samples from six ADtg mice and six age- and sex-matched littermates. The fluorescence of specific signals was captured using the same setting and exposure time for each image and mouse, with a 10-μm-thick Z-stack by using an Axio Imager Z1 microscope (with motorized Z-drive) with AxioCam MRm monochrome camera version 3.0 (at a resolution of 1388×1040 pixels, 6.45 μm×6.45 μm pixel size, and a dynamic range of >1:2200, which delivers low-noise images due to a Peltier-cooled sensor). Images were captured at 40× objective, at a respective resolution of 0.25 μm. Fifteen images were obtained randomly from each region of central-, mid-, and far-peripheral retina (five from each region) per subject. Acquired images were converted to gray scale and standardized to baseline using a histogram-based threshold in the NIH ImageJ software program (version 1.52o). For each biomarker, the total area of immunoreactivity was determined using the same threshold percentage from the baseline in ImageJ (with the same percentage threshold setting for all diagnostic groups). The images were then subjected to particle analysis for lectin, Aβ, and PDGFRβ to determine the immunoreactive (IR) area. The ratio of Aβ or PDGFRβ to lectin was calculated by dividing the Aβ-IR or PDGFR-IR area by the lectin-IR area in each of the 15 images (described above) and averaging the values per mouse.

For FIG. 25, quantitative analysis of FITC or Texas Red area in each microscopic field of retinal flat-mount was performed based on five ADtg mice and five age- and sex-matched littermates. The fluorescence of specific signals was captured using the same setting and exposure time for each image and mouse by using an Axio Imager Z1 microscope as described above. Images were captured at 40× objective, at a respective resolution of 0.25 μm. Ten images were randomly taken throughout the whole retina, then the images were converted to gray scale and subjected to ImageJ analysis as described above. Particle analyses were performed on FITC and Texas Red signal. Finally, the IR areas were calculated by averaging the ten images per mouse.

Statistical Analysis

GraphPad Prism version 8.3.0 (GraphPad Software) was used for the analyses. A comparison of three or more groups was performed using one-way ANOVA followed by Tukey's multiple comparison post-hoc test of paired groups. Groups with two independent variables/factors were analyzed by using two-way ANOVA followed by Tukey's multiple comparison test to further understand the interaction between the two independent variables. Two group comparisons were analyzed using a two-tailed unpaired Student t-test. The statistical association between two or more variables was determined by Pearson's correlation coefficient (r) test (Gaussian-distributed variables; GraphPad Prism). Pearson's r indicates the direction and strength of the linear relationship between two variables. Required sample sizes for two group (differential mean) comparisons were calculated using the nQUERY t-test model, assuming a two-sided α level of 0.05, 80% power, and unequal variances, with the means and common standard deviations for the different parameters. Results are expressed as means±standard errors of the means (SEMs). A P value less than 0.05 is considered significant.

Results

Figure 21:
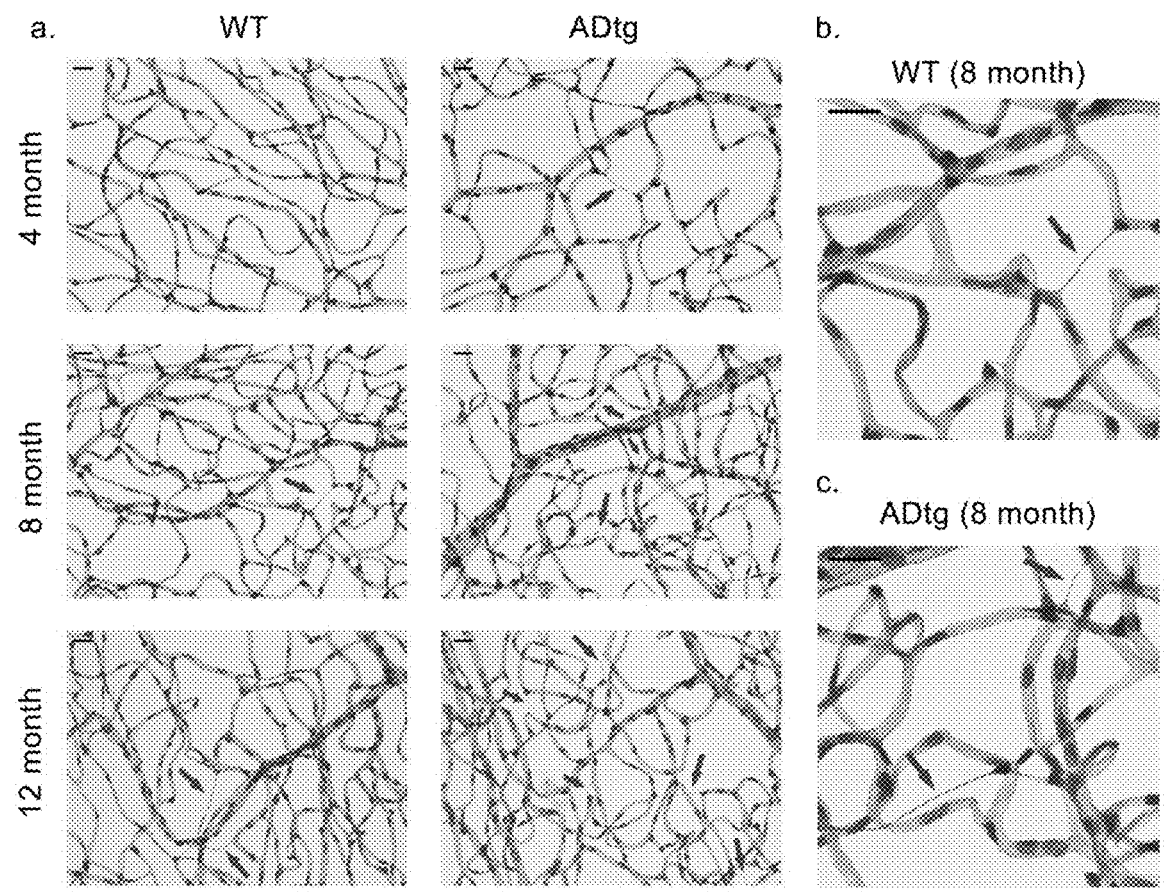
FIG. 21 (panels a-f) shows identification of retinal capillary degeneration in $APP_{SWE}/PS1_{\Delta E9}$ (ADtg) mice that intensified during disease progression. ADtg mice and their age- and sex-matched wild-type (WT) littermates, males and females in equal number, were used in this study at the age of 4 (n=16; ADtg=8 and WT=8), 8 (n=16; ADtg=8 and WT=8) and 12 (n=16; ADtg=8 and WT=8) months. a. Representative images of periodic acid-Schiff (PAS)-stained, hematoxylin-counterstained isolated retinal microvasculature from ADtg and matched WT littermates. Acellular degenerated retinal capillaries are indicated by red arrows. b-c. Higher magnification representative images of acellular, degenerated retinal capillaries from 8-month-old b. WT mouse and c. ADtg mouse (red arrows indicate degenerated capillaries). Scale bars=20 μm. d. Count of acellular degenerated retinal capillaries (Degen Caps) in 1 mm² microscopic fields as manually determined in ADtg and WT control mice (mean age: 8 months, 50% females for both WT and ADtg groups). e-f. Numbers of degenerated retinal capillaries when mice are stratified by mouse genotypes, WT or ADtg, by either e. age groups of 4, 8, and 12 months or f. sex. Data from individual mice (circles) as well as group means±SEMs are shown. Black-filled circles represent males and clear circles represent females. Fold changes are shown in red. *p<0.05, p<0.01, *p<0.001, ****p<0.0001, by two-way ANOVA with Tukey's post-hoc multiple comparison test or by unpaired 2-tailed Student t-test. P and F values of two-way ANOVA refer to comparisons of age groups ($P_A$, $F_A$), ADtg vs WT genotype groups ($P_G$, $F_G$), gender groups ($P_{Ge}$, $F_{Ge}$), and overall interactions ($P_1$, $F_1$).
Figure 21:
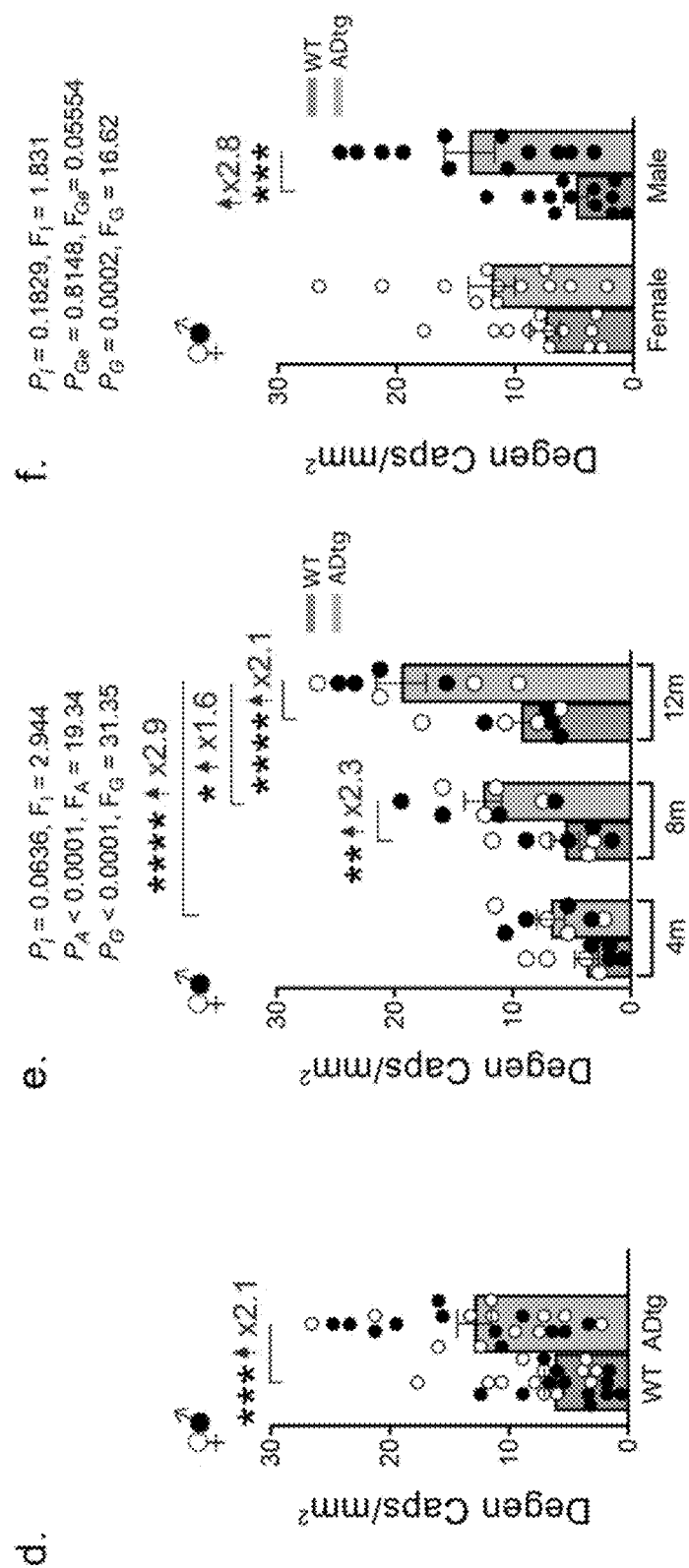

Age-Dependent Progressive Degeneration of Retinal Microvessels in Healthy and ADtg Mice To explore retinal microvascular degeneration in AD-model mice at ascending ages, we used an elastase-based enzymatic digestion method to isolate the retinal vascular network in 4-, 8- and 12-month-old ADtg mice as compared to their age- and sex-matched non-transgenic littermates. Specifically, PAS staining was applied to detect polysaccharides, thereby enabling visualization of the vascular network in isolated retinal blood vessels from ADtg mice and WT controls; hematoxylin counterstaining was utilized to highlight the nuclei. We first qualitatively observed more degenerated retinal capillaries in ADtg mice than in the WT control mice, including as early as in 4-month-old mice (FIG. 21a). We determined degenerated retinal microvessels as acellular, basement membrane-only PAS staining-positive structures, which are illustrated at higher magnification microscopic images from mice at the age of 8 months (FIG. 21b-c) and 12 months (FIG. 26a-b). While both genotypes displayed increasing numbers of degenerated retinal vasculature as the animals grew older, the ADtg mice exhibited an intensified vascular pathology (FIG. 21a-c and FIG. 21a-b, red arrows).

To quantify retinal vascular degeneration in different mouse genotypes, ages and sex, we manually counted the degenerated retinal microvessels in pre-defined 1 mm$^2$ area of each microscopic field (FIG. 21d-f and FIG. 26c-d). We first analyzed the pooled mice groups to measure the overall AD-associated genotype effect. Regardless of animal age and sex, there was a significant 2.1-fold increase in retinal acellular capillaries in ADtg versus WT mice (FIG. 21d). Using two-way ANOVA analysis and Tukey's post-test, we detected a highly significant increase in amounts of degenerated retinal microvasculature in ADtg mice when compared to WT mice at 12 months of age (FIG. 21e). Furthermore, there was significantly more vascular degeneration in 12-month than in 4-month-old ADtg mice. We also revealed an earlier significant difference in degenerated microvessels between ADtg and WT retinas in mice 8 months of age (FIG. 21e). Although both sexes showed increases in acellular capillaries, only the male mice reached a statistical significance between the genotypes (FIG. 21f). Further age comparison analysis per each genotype separately, uncovered progressive increases of retinal microvascular degeneration with aging in both the WT and ADtg mice (FIGS. 26c and 26d, respectively).

Downregulation of Retinal Vascular PDGFRβ in ADtg Mice

Since pericyte loss generally precedes microvascular degeneration in retinal vascular degenerative diseases, we sought to further evaluate whether pericytes undergo degeneration in the retina of ADtg mice. To this end, we immunostained isolated retinal vasculature with PDGFRβ as a pericyte marker in capillaries, together with lectin for blood vessels and DAPI counterstaining for nuclei (FIG. 22a). We found a dramatic loss of PDGFRβ signal in retinal vasculature from ADtg mice compared to WT controls at 8 months of age. A further loss of PDGFRβ expression was evident in older, 12-month-old ADtg mice. Stereological quantification of PDGFRβ immunoreactive (IR) area and PDGFRβ-IR area normalized to lectin-IR area confirmed significant 49% and 52% decreases in vascular PDGFRβ signal, respectively, in ADtg compared to WT control mice (FIG. 27a and FIG. 27b, respectively). When we separated mice per age group, either 8 or 12 months, a more significant decrease in vascular PDGFRβ signal was detected at the earlier age of 8 months in ADtg mice as compared to matched WT mice (FIG. 22c and FIG. 22b). We did not notice any sex-related differences in vascular PDGFRβ expression, and significant reductions in PDGFRβ were detected in both female and male ADtg mice versus WT controls (FIG. 22d and FIG. 27c). Importantly, Pearson's (r) correlation analysis revealed that retinal vascular PDGFRβ deficiency significantly correlated with retinal microvascular degeneration (FIG. 22e). This may suggest that PDGFRβ downregulation is indeed accompanied by capillary degeneration, similar to what is known in other retinal vascular degenerative diseases such as DR.

Vascular Aβ Deposition in ADtg Mice

Next, we investigated whether Aβ accumulates in retinal blood vessels of this double-transgenic ADtg mice. To achieve this, we first immunostained isolated retinal vasculature with 4G8 to visualize Aβ, together with lectin staining for retinal blood vessels and DAPI nuclei staining (FIG. 23 and FIG. 28). While 4G8$^+$-Aβ signal is absent in perfused WT mice, in perfused ADtg mice, strong Aβ signal is present in retinal blood vessels (FIG. 23a-b). Aβ is found to accumulate in blood vessel walls, vascular cells, or attached to endothelial cells from the lumen side (FIG. 23a-d, 23g-g' and FIG. 28a-b, 28i-j). Stereological quantification of Aβ confirmed a significant increase in Aβ in ADtg mice when we analyzed all mice together (FIG. 23e; see FIG. 28c for data normalized per lectin-IR area) and when we separated the animals into 8-month-old and 12-month-old groups (FIG. 23f; see FIG. 28f for data normalized to lectin-IR area). However, there was no statistically significant difference between the different age groups. Similar to PDGFRβ, both 12-month-old ADtg sexes showed significant increases in vascular 4G8-Aβ burden (FIG. 28d-e), with males reaching statistical significance probably due to larger sample size. No significant correlation was observed between retinal vascular 4G8-Aβ burden and capillary degeneration (FIG. 28g) or vascular PDGFRβ expression (FIG. 28h). Importantly, we revealed that Aβ signal in isolated retinal blood vessels often accumulated in vessel walls and colocalized with lectin (FIG. 23g-g' and FIG. 28b). Furthermore, by using 11A50-B10 staining in isolated vasculature, we demonstrated the specific accumulation of Aβ$_{40}$ alloforms in retinal blood vessels of perfused ADtg mice (FIG. 28i-j). On another occasion, by confocal virtual cross-section, Aβ$_{40}$ deposition in retinal vascular was detected as encored to Lectin$^+$-vessel wall from the lumen side (FIG. 28j). The localization of Aβ$_{40}$ deposits in retinal blood vessels of ADtg mice is further demonstrated in two 3D-movies (S1 and S2 Movies). Finally, we prepared retinal cross-sections from the same mice cohort and validated abundant retinal vascular Aβ accumulation based on double-positive fluorescent staining of thioflavin-S$^+$ fibrillar Aβ and 11A50-B10$^+$ Aβ$_{40}$ colocalized with CD31$^+$ endothelial cells in ADtg mice as compared to WT mice (FIG. 23h-i and FIG. 28k-n).

Differential Expression of BRB Tight Junction Components and Increased Retinal NF-κB p65 Phosphorylation in ADtg Mice The discovery of exacerbated PDGFRβ loss and capillary degeneration together with vascular Aβ deposition in the retinas of ADtg mice raises the question of whether these small-vessel pathologies are related to cell-to-cell molecular BRB junction disruptions. To address this, we extracted protein homogenates from retinas obtained from ADtg mice and WT controls at 4-, 8-, and 12-months of age. We measured the protein levels of key tight junction components of the blood-tissue barrier, claudin-1 and zonula occludens-1 (ZO-1), by western blot (WB) analyses (FIG. 24a-b). We also assessed phosphorylation of NF-κB p65 at Ser-536 for potential activation of the relevant inflammatory cascades (FIG. 24c). Densitometric analysis of WB images showed that as compared to matched WT littermates, there were early and significant decreases of retinal claudin-1 and ZO-1 in 8- and 4-month-old ADtg mice, respectively (FIG. 24d-e). Unexpectedly, a significant increase in retinal ZO-1 was detected in 12-month-old ADtg mice. Further, in the 12-month-old ADtg mice, a substantial increase in retinal NF-κB p65 phosphorylation was observed (FIG. 24f), suggesting a heightened inflammatory response. Next, we evaluated if aging played a role in the alteration of these vascular junction molecules. In WT mice, we noticed a 37% decrease in retinal claudin-1 at 12 months of age when compared to animals 8 months old (FIG. 29a). As for retinal ZO-1, we found 47%-510% decreased levels in WT mice at both 8 and 12 months of age as compared with the 4-month-old WT group (FIG. 29b). The opposite patterns were detected in ADtg mice, where retinal ZO-1 was increased at 12 months (FIG. 29b). Phosphorylation of NF-κB p65 did not appear to be affected by age (FIG. 29c). When we regrouped mice by sex and genotype, no significant differences in any of the three molecules were found (FIG. 29d-f). Pearson's (r) correlation analyses revealed a moderate, positive correlation between retinal claudin-1 levels and retinal capillary PDGFRβ expression (FIG. 24g), but no correlation with retinal ZO-1 (FIG. 24h), suggesting claudin-1 is associated with retinal capillary degeneration in this mouse model. A trend of correlation was also found between NF-κB p65 phosphorylation levels and vascular PDGFRβ expression (FIG. 24i), suggesting that activation of inflammation could play a role in pericyte loss in the ADtg mice retina. Finally, we detected a highly significant inverse correlation between retinal claudin-1 levels and the extent of retinal capillary degeneration (FIG. 24j; see extended correlation analyses in FIG. 29g-k).

Retinal Microvascular Leakage in ADtg Mice

So far, we have demonstrated increased degenerated capillaries, vascular amyloidosis, and altered cell-cell junctions in the retina of ADtg mice, in comparison with their age- and sex-matched WT littermates. The next question is whether such changes lead to impaired BRB permeability and retinal vascular leakage in ADtg mice. To determine this, we first injected fluorescein (~0.3 kD) intraperitoneally in ADtg and WT mice. Using the noninvasive Micron-III retinal imaging microscope, we detected no fluorescein leakage in any of the WT mice at 8, 12 or 16 months of age (FIG. 25a; a representative image from a 12-month-old WT mouse shown). However, we were able to identify fluorescein leakage in one out of three 12-month-old ADtg mice (FIG. 25c-d, dotted lines or arrows indicating spots of leakage). A representative image from a 12-month-old ADtg mouse with no clear retinal vascular leakage phenotype is shown in FIG. 5b; representative images from 8- and 16-month-old ADtg mice are included in FIG. 30a-b. We further investigated BRB permeability in AD by co-injecting two compounds with larger predefined molecular weights, FITC-dextran (2000 kD) and Texas Red-dextran (3 kD), into the tail veins of ADtg mice and age- and sex-matched WT mice. Thirty minutes following i.v. injection, the perfused mice were sacrificed, eyes were extracted and whole retinas were isolated. Ex vivo retinal flat-mount imaging revealed intense FITC and Texas Red signals in retinal blood vessel walls and retinal parenchyma of ADtg mice relative to the WT littermates (FIG. 25e-f). Our stereological quantification confirmed substantial 30- to 90-fold increases in both retinal FITC and Texas Red signals, respectively, in ADtg mice (FIG. 25g-h).

Live Retinal Imaging Technique—In Vivo Retinal Vascular Imaging for Pericytes

Referring to FIG. 31, NEUROTRACE™ 500/525 (Thermofisher #N21480), Green Fluorescent Nissl Stain—Solution in DMSO, was retro-orbitally injected into a wild type mouse for imaging vascular pericytes. A previous study found this dye specifically stained cerebral microvascular pericytes when administrated topically. Images were taken 5 minutes after following injection by using a noninvasive Micron-III retinal rodent imaging microscope.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of"

What is claimed is:

1. A method of detecting pericytes, platelet-derived growth factor receptor-β (PDGFR-β), low-density lipoprotein (LDL) receptor-related protein-1 (LRP-1), or combinations thereof in a subject in need thereof, the method comprising:
obtaining a live retinal image of a retina of the subject with an imaging device including a microscope and/or a camera; and
detecting a decrease in the amount of pericytes, platelet-derived growth factor receptor-β (PDGFR-β), LDL receptor-related protein-1 (LRP-1), or combinations thereof present in the retina of the subject using a live retinal imaging technique and/or an advanced ophthalmic imaging technique,
wherein the decrease in the amount of pericytes is detected by comparing the obtained retinal image to a control retinal image or the subject's previous retinal image.

2. The method of claim 1, wherein:
the subject exhibits one or more symptoms of cognitive impairment;
the subject has or is suspected of having mild cognitive impairment (MCI) and/or Alzheimer's disease; and/or
the subject desires a screening regarding mild cognitive impairment (MCI) or Alzheimer's disease.

3. The method of claim 1, wherein the detecting the decrease in the amount of pericytes, PDGFR-β, LRP-1 or combinations thereof present in the retina of the subject comprises using adaptive optics, optical coherence tomography angiography, color fundus photography, fluorescein fundus imaging, fluorescein angiography, indocyanine green angiography, scanning laser ophthalmoscopy, optical coherence tomography, confocal microscopy, retinal hyperspectral imaging, and/or optical coherence tomography angiography (OCTA).

4. The method of claim 1, wherein detecting the decrease in the amount of PDGFR-β present in the retina of the subject comprises:
administering a contrast agent to the subject; and
using optical imaging to detect the amount of PDGFR-β present in the retina.

5. The method of claim 1, wherein the detecting the decrease in the amount of PDGFR-β present in the retina of the subject comprises:
administering a labelled anti-PDGFR-β antibody; and
using optical imaging to detect the amount of PDGFR-β present in the retina.

6. The method of claim 1, wherein the detecting the decrease in the amount of LRP-1 present in the retina of the subject comprises:
administering a labelled anti-LRP-1 antibody; and
using optical imaging to detect the amount of LRP-1 present in the retina.

7. The method of claim 1, further comprising detecting an increase in vascular Aβ deposition in the retina of the subject.

8. The method of claim 7, wherein the detecting an increase in vascular Aβ deposition in the retina of the subject comprises:
administering an anti-Aβ compound; and
using optical imaging to detect the amount of Aβ deposition in the retina.

9. The method of claim 1, further comprising predicting cognitive decline in the subject based on the detection of the decrease in the amount of pericytes, PDGFR-β, LRP-1, or combinations thereof present in the retina.

10. The method of claim 1, further comprising monitoring the subject by repeating the method.

11. A method of monitoring cognitive status of a subject in need thereof, the method comprising:
obtaining first retinal image of a retina of the subject with an imaging device including a microscope and/or a camera;
detecting, in the first retinal image, an amount of pericytes, platelet-derived growth factor receptor-β

(PDGFR-β), LDL receptor-related protein-1 (LRP-1), or combinations thereof present in the retina of the subject using a live retinal imaging technique and/or an advanced ophthalmic imaging technique;
obtaining a second retinal image of the retina of the subject with the imaging device, subsequent to the first retinal image;
detecting, in the second retinal image, an amount of pericytes, PDGFR-β, LRP-1, or combinations thereof present in the retina of the subject using a live retinal imaging technique and/or an advanced ophthalmic imaging technique;
comparing the amount of pericytes, PDGFR-β, LRP-1, or combinations thereof present in the first retinal image and the second retinal image; and
detecting whether there is a change in the amount of pericytes, PDGFR-β, LRP-1, or combinations thereof present in the retina.

12. The method of claim 11, further comprising:
detecting a decrease in the amount of pericytes, PDGFR-β, LRP-1, or combinations thereof present in the retina; and
administering a mild cognitive impairment (MCI) or Alzheimer's disease therapy.

13. The method of claim 11, wherein:
the subject exhibits one or more symptoms of cognitive impairment and/or the subject has or is suspected of having mild cognitive impairment (MCI) and/or Alzheimer's disease; and/or
the subject desires a screening regarding mild cognitive impairment (MCI) or Alzheimer's disease.

14. The method of claim 11, wherein the detecting the amount of pericytes, PDGFR-β, LRP-1, or combinations thereof present in the retina of the subject comprises using adaptive optics, optical coherence tomography angiography, color fundus photography, fluorescein fundus imaging, fluorescein angiography, indocyanine green angiography, scanning laser ophthalmoscopy, optical coherence tomography, confocal microscopy, retinal hyperspectral imaging, and/or optical coherence tomography angiography (OCTA).

15. A method of detecting an alteration in blood-retinal barrier (BRB) cell tight junction in a subject in need thereof, the method comprising:
assaying a biological sample from the subject by contacting the biological sample with an anti-claudin-1 antibody and detecting a decrease in claudin-1, in the biological sample, wherein the decrease in claudin-1 is compared to a control claudin-1 level or compared to the subject's previous claudin-1 level; or
assaying a biological sample from the subject by contacting the biological sample with an anti-phospho-NF-κB antibody and detecting an increase in NF-κB phosphorylation levels, in the biological sample, wherein the increase in NF-κB phosphorylation levels is compared to a control NF-κB phosphorylation level or compared to the subject's previous NF-κB phosphorylation level; or
detecting an increase in retinal vascular leakage level compared to a control level, or compared to the subject's previous retinal vascular leakage level, by administering a fluorophore to the subject; imaging a retina of the subject; and detecting a level of fluorophore leakage from an image of the retina.

16. The method of claim 15, wherein the subject in need thereof exhibits one or more symptoms of cognitive impairment, is a subject having or suspected of having mild cognitive impairment (MCI), or a subject having or suspected of having Alzheimer's disease.

17. The method of claim 15, wherein NF-κB phosphorylation is NF-κB p65 phosphorylation.

18. The method of claim 15, wherein at least one of the decrease in claudin-1, the increase in NF-κB phosphorylation levels, or the increase in retinal vascular leakage level indicates an alteration in BRB cell tight junction.

19. The method of claim 15, wherein the detected alteration in BRB cell tight junction indicates cognitive impairment and/or cognitive decline in the subject.

* * * * *